(12) United States Patent
Siegel et al.

(10) Patent No.: US 12,245,942 B2
(45) Date of Patent: Mar. 11, 2025

(54) DEPLOYMENT TOOLS AND METHODS FOR DELIVERING A DEVICE TO A NATIVE HEART VALVE

(71) Applicant: Edwards Lifesciences Corporation, Irvine, CA (US)

(72) Inventors: Alexander J Siegel, Irvine, CA (US); Nicolas Schleiger, Costa Mesa, CA (US); Gregory Scott Tyler, II, Winston-Salem, NC (US)

(73) Assignee: EDWARDS LIFESCIENCES CORPORATION, Irvine, CA (US)

( * ) Notice: Subject to any disclaimer, the term of this patent is extended or adjusted under 35 U.S.C. 154(b) by 926 days.

(21) Appl. No.: 17/246,539

(22) Filed: Apr. 30, 2021

(65) Prior Publication Data

US 2021/0251757 A1    Aug. 19, 2021

Related U.S. Application Data

(63) Continuation of application No. PCT/US2019/062194, filed on Nov. 19, 2019.
(Continued)

(51) Int. Cl.
*A61F 2/24* (2006.01)
*A61M 25/00* (2006.01)
*A61M 25/01* (2006.01)

(52) U.S. Cl.
CPC ....... *A61F 2/2466* (2013.01); *A61M 25/0054* (2013.01); *A61F 2/2454* (2013.01);
(Continued)

(58) Field of Classification Search
CPC ...... A61F 2/2427; A61F 2/243; A61F 2/2451; A61F 2/2454; A61F 2/2466; A61M 25/0054; A61M 25/0013; A61M 25/0015; A61M 25/0026; A61M 25/0029; A61M 25/0138; A61M 25/0141; A61M 25/0147; A61M 25/0105; A61M 2025/015;
(Continued)

(56) References Cited

U.S. PATENT DOCUMENTS

| 3,874,388 A | 4/1975 | King et al. |
| 4,340,091 A | 7/1982 | Skelton et al. |

(Continued)

FOREIGN PATENT DOCUMENTS

| CN | 1142351 A | 2/1997 |
| CN | 106175845 A | 12/2016 |

(Continued)

OTHER PUBLICATIONS

Al Zaibag et al., "Percutaneous Balloon Valvotomy in Tricuspid Stenosis", British Heart Journal, vol. 57, No. 1, Jan. 1987.
(Continued)

*Primary Examiner* — Robert A Lynch
(74) *Attorney, Agent, or Firm* — Anya Adams

(57) ABSTRACT

A flexible delivery catheter can be used to deploy valve repair and replacement devices at an implant site for the repair or replacement of poorly functioning native heart valves. Such a catheter can include a flexible tube having a plurality of links. A control wire can be connected to the plurality of links, such that applying tension to the control wire causes the flexible tube to bend.

21 Claims, 34 Drawing Sheets

Related U.S. Application Data

(60) Provisional application No. 62/770,071, filed on Nov. 20, 2018.

(52) U.S. Cl.
CPC ..... *A61M 25/0013* (2013.01); *A61M 25/0015* (2013.01); *A61M 25/0029* (2013.01); *A61M 25/0138* (2013.01); *A61M 25/0141* (2013.01); *A61M 25/0147* (2013.01)

(58) Field of Classification Search
CPC ......... A61M 2025/0161; A61B 1/0055; A61B 1/0056; A61B 1/0057; A61B 1/008; A61B 2017/003; A61B 2017/0035; A61B 2017/0039; A61B 2017/00314; A61B 2017/00318; A61B 2017/00323
See application file for complete search history.

(56) References Cited

U.S. PATENT DOCUMENTS

| | | |
|---|---|---|
| 4,506,669 A | 3/1985 | Blake, III |
| 4,590,937 A | 5/1986 | Deniega |
| 4,693,248 A | 9/1987 | Failla |
| 4,803,983 A | 2/1989 | Siegel |
| 5,125,895 A | 6/1992 | Buchbinder et al. |
| 5,171,252 A | 12/1992 | Friedland |
| 5,195,962 A | 3/1993 | Martin et al. |
| 5,292,326 A | 3/1994 | Green et al. |
| 5,327,905 A | 7/1994 | Avitall |
| 5,363,861 A | 11/1994 | Edwards et al. |
| 5,370,685 A | 12/1994 | Stevens |
| 5,389,077 A | 2/1995 | Melinyshyn et al. |
| 5,411,552 A | 5/1995 | Andersen et al. |
| 5,450,860 A | 9/1995 | O'Connor |
| 5,456,674 A | 10/1995 | Bos et al. |
| 5,474,057 A | 12/1995 | Makower et al. |
| 5,478,353 A | 12/1995 | Yoon |
| 5,487,746 A | 1/1996 | Yu et al. |
| 5,565,004 A | 10/1996 | Christoudias |
| 5,607,462 A | 3/1997 | Imran |
| 5,609,598 A | 3/1997 | Laufer et al. |
| 5,611,794 A | 3/1997 | Sauer et al. |
| 5,626,607 A | 5/1997 | Malecki et al. |
| 5,695,504 A | 12/1997 | Gifford, III et al. |
| 5,716,417 A | 2/1998 | Girard et al. |
| 5,727,569 A | 3/1998 | Benetti et al. |
| 5,741,297 A | 4/1998 | Simon |
| 5,782,746 A | 7/1998 | Wright |
| 5,797,960 A | 8/1998 | Stevens et al. |
| 5,836,311 A | 11/1998 | Borst et al. |
| 5,843,076 A | 12/1998 | Webster, Jr. et al. |
| 5,855,590 A | 1/1999 | Malecki et al. |
| 5,885,271 A | 3/1999 | Hamilton et al. |
| 5,888,247 A | 3/1999 | Benetti |
| 5,891,017 A | 4/1999 | Swindle et al. |
| 5,891,112 A | 4/1999 | Samson |
| 5,894,843 A | 4/1999 | Benetti et al. |
| 5,921,979 A | 7/1999 | Kovac et al. |
| 5,944,738 A | 8/1999 | Amplatz et al. |
| 5,957,835 A | 9/1999 | Anderson et al. |
| 5,972,020 A | 10/1999 | Carpentier et al. |
| 5,980,534 A | 11/1999 | Gimpelson |
| 6,004,329 A | 12/1999 | Myers et al. |
| 6,010,531 A | 1/2000 | Donlon et al. |
| 6,017,358 A | 1/2000 | Yoon et al. |
| 6,086,600 A | 7/2000 | Kortenbach |
| 6,120,496 A | 9/2000 | Whayne et al. |
| 6,132,370 A | 10/2000 | Furnish et al. |
| 6,162,239 A | 12/2000 | Manhes |
| 6,165,183 A | 12/2000 | Kuehn et al. |
| 6,182,664 B1 | 2/2001 | Cosgrove |
| 6,193,732 B1 | 2/2001 | Frantzen et al. |
| 6,193,734 B1 | 2/2001 | Bolduc et al. |
| 6,200,315 B1 | 3/2001 | Galser et al. |
| 6,228,032 B1 | 5/2001 | Eaton et al. |
| 6,241,743 B1 | 6/2001 | Levin et al. |
| 6,269,819 B1 | 8/2001 | Oz et al. |
| 6,269,829 B1 | 8/2001 | Chen et al. |
| 6,312,447 B1 | 11/2001 | Grimes |
| 6,461,366 B1 | 10/2002 | Seguin |
| 6,468,285 B1 | 10/2002 | Hsu et al. |
| 6,508,806 B1 | 1/2003 | Hoste |
| 6,508,825 B1 | 1/2003 | Selmon et al. |
| 6,530,933 B1 | 3/2003 | Yeung et al. |
| 6,537,290 B2 | 3/2003 | Adams et al. |
| 6,544,215 B1 | 4/2003 | Bencini et al. |
| 6,626,930 B1 | 9/2003 | Allen et al. |
| 6,629,534 B1 | 10/2003 | St. Goar et al. |
| 6,719,767 B1 | 4/2004 | Kimblad |
| 6,764,510 B2 | 7/2004 | Vidlund et al. |
| 6,770,083 B2 | 8/2004 | Seguin |
| 6,837,867 B2 | 1/2005 | Kortelling |
| 6,855,137 B2 | 2/2005 | Bon |
| 6,913,614 B2 | 7/2005 | Marino et al. |
| 6,939,337 B2 | 9/2005 | Parker et al. |
| 6,945,956 B2 | 9/2005 | Waldhauser et al. |
| 7,048,754 B2 | 5/2006 | Martin et al. |
| 7,101,395 B2 | 9/2006 | Tremulis et al. |
| 7,125,421 B2 | 10/2006 | Tremulis et al. |
| 7,276,062 B2 * | 10/2007 | McDaniel ........... A61M 25/005 606/49 |
| 7,288,097 B2 | 10/2007 | Seguin |
| 7,371,210 B2 | 5/2008 | Brock et al. |
| 7,464,712 B2 | 12/2008 | Oz et al. |
| 7,509,959 B2 | 3/2009 | Oz et al. |
| 7,569,062 B1 | 8/2009 | Kuehn et al. |
| 7,618,449 B2 | 11/2009 | Tremulis et al. |
| 7,682,369 B2 | 3/2010 | Seguin |
| 7,731,706 B2 | 6/2010 | Potter |
| 7,744,609 B2 | 6/2010 | Allen et al. |
| 7,748,389 B2 | 7/2010 | Salahieh et al. |
| 7,753,932 B2 | 7/2010 | Gingrich et al. |
| 7,758,596 B2 | 7/2010 | Oz et al. |
| 7,780,723 B2 | 8/2010 | Taylor |
| 7,803,185 B2 | 9/2010 | Gabbay |
| 7,824,443 B2 | 11/2010 | Salahieh et al. |
| 7,981,123 B2 | 7/2011 | Seguin |
| 7,988,724 B2 | 8/2011 | Salahieh et al. |
| 8,052,750 B2 | 11/2011 | Tuval et al. |
| 8,070,805 B2 | 12/2011 | Vidlund et al. |
| 8,096,985 B2 | 1/2012 | Legaspi et al. |
| 8,104,149 B1 | 1/2012 | McGarity |
| 8,133,239 B2 | 3/2012 | Oz et al. |
| 8,147,542 B2 | 4/2012 | Maisano et al. |
| 8,172,856 B2 | 5/2012 | Eigler et al. |
| 8,206,437 B2 | 6/2012 | Bonhoeffer et al. |
| 8,216,301 B2 | 7/2012 | Bonhoeffer et al. |
| 8,303,653 B2 | 11/2012 | Bonhoeffer et al. |
| 8,313,525 B2 | 11/2012 | Tuval et al. |
| 8,348,995 B2 | 1/2013 | Tuval et al. |
| 8,348,996 B2 | 1/2013 | Tuval et al. |
| 8,414,643 B2 | 4/2013 | Tuval et al. |
| 8,425,404 B2 | 4/2013 | Wilson et al. |
| 8,449,599 B2 | 5/2013 | Chau et al. |
| 8,449,606 B2 | 5/2013 | Eliasen et al. |
| 8,460,368 B2 | 6/2013 | Taylor et al. |
| 8,470,028 B2 | 6/2013 | Thornton et al. |
| 8,480,730 B2 | 7/2013 | Maurer et al. |
| 8,540,767 B2 | 9/2013 | Zhang |
| 8,579,965 B2 | 11/2013 | Bonhoeffer et al. |
| 8,585,756 B2 | 11/2013 | Bonhoeffer et al. |
| 8,652,202 B2 | 2/2014 | Alon et al. |
| 8,668,733 B2 | 3/2014 | Haug et al. |
| 8,721,665 B2 | 5/2014 | Oz et al. |
| 8,740,918 B2 | 6/2014 | Seguin |
| 8,771,347 B2 | 7/2014 | DeBoer et al. |
| 8,778,017 B2 | 7/2014 | Ellasen et al. |
| 8,834,564 B2 | 9/2014 | Tuval et al. |
| 8,840,663 B2 | 9/2014 | Salahieh et al. |
| 8,876,894 B2 | 11/2014 | Tuval et al. |
| 8,876,895 B2 | 11/2014 | Tuval et al. |
| 8,945,177 B2 | 2/2015 | Dell et al. |
| 9,034,032 B2 | 5/2015 | McLean et al. |

(56) References Cited

U.S. PATENT DOCUMENTS

| | | |
|---|---|---|
| 9,198,757 B2 | 12/2015 | Schroeder et al. |
| 9,220,507 B1 | 12/2015 | Patel et al. |
| 9,259,317 B2 | 2/2016 | Wilson et al. |
| 9,282,972 B1 | 3/2016 | Patel et al. |
| 9,301,834 B2 | 4/2016 | Tuval et al. |
| 9,308,360 B2 | 4/2016 | Bishop et al. |
| 9,387,071 B2 | 7/2016 | Tuval et al. |
| 9,427,327 B2 | 8/2016 | Parrish |
| 9,439,763 B2 | 9/2016 | Geist et al. |
| 9,510,837 B2 | 12/2016 | Seguin |
| 9,510,946 B2 | 12/2016 | Chau et al. |
| 9,572,660 B2 | 2/2017 | Braido et al. |
| 9,642,704 B2 | 5/2017 | Tuval et al. |
| 9,700,445 B2 | 7/2017 | Martin et al. |
| 9,775,963 B2 | 10/2017 | Miller |
| D809,139 S | 1/2018 | Marsot et al. |
| 9,889,002 B2 | 2/2018 | Bonhoeffer et al. |
| 9,949,824 B2 | 4/2018 | Bonhoeffer et al. |
| 10,076,327 B2 | 9/2018 | Ellis et al. |
| 10,076,415 B1 | 9/2018 | Metchik et al. |
| 10,099,050 B2 | 10/2018 | Chen et al. |
| 10,105,221 B2 | 10/2018 | Siegel |
| 10,105,222 B1 | 10/2018 | Metchik et al. |
| 10,111,751 B1 | 10/2018 | Metchik et al. |
| 10,123,873 B1 | 11/2018 | Metchik et al. |
| 10,130,475 B1 | 11/2018 | Metchik et al. |
| 10,136,993 B1 | 11/2018 | Metchik et al. |
| 10,159,570 B1 | 12/2018 | Metchik et al. |
| 10,226,309 B2 | 3/2019 | Ho et al. |
| 10,231,837 B1 | 3/2019 | Metchik et al. |
| 10,238,493 B1 | 3/2019 | Metchik et al. |
| 10,238,494 B2 | 3/2019 | McNiven et al. |
| 10,238,495 B2 | 3/2019 | Marsot et al. |
| 10,299,924 B2 | 5/2019 | Kizuka |
| 10,376,673 B2 | 8/2019 | Van Hoven et al. |
| 10,575,841 B1 | 3/2020 | Paulos |
| 2001/0005787 A1 | 6/2001 | Oz et al. |
| 2002/0013571 A1 | 1/2002 | Goldfarb et al. |
| 2002/0107531 A1 | 8/2002 | Schreck et al. |
| 2002/0173811 A1 | 11/2002 | Tu et al. |
| 2002/0183787 A1 | 12/2002 | Wahr et al. |
| 2003/0144573 A1 | 7/2003 | Heilman et al. |
| 2003/0187467 A1 | 10/2003 | Schreck |
| 2003/0208231 A1 | 11/2003 | Williamson et al. |
| 2004/0003819 A1 | 1/2004 | St. Goar et al. |
| 2004/0030382 A1 | 2/2004 | St. Goar et al. |
| 2004/0034365 A1 | 2/2004 | Lentz et al. |
| 2004/0044350 A1 | 3/2004 | Martin et al. |
| 2004/0044365 A1 | 3/2004 | Bachman |
| 2004/0049207 A1 | 3/2004 | Goldfarb et al. |
| 2004/0122448 A1 | 6/2004 | Levine |
| 2004/0127981 A1 | 7/2004 | Rahdert et al. |
| 2004/0127982 A1 | 7/2004 | Machold et al. |
| 2004/0147943 A1 | 7/2004 | Kobayashi |
| 2004/0181135 A1 | 9/2004 | Drysen |
| 2004/0181206 A1 | 9/2004 | Chiu et al. |
| 2004/0181238 A1 | 9/2004 | Zarbatany et al. |
| 2004/0210307 A1 | 10/2004 | Khairkhahan |
| 2004/0220593 A1 | 11/2004 | Greenhalgh |
| 2005/0010287 A1 | 1/2005 | Macoviak et al. |
| 2005/0049618 A1 | 3/2005 | Masuda et al. |
| 2005/0070926 A1 | 3/2005 | Ortiz |
| 2005/0137690 A1 | 6/2005 | Salahieh et al. |
| 2005/0143767 A1 | 6/2005 | Kimura et al. |
| 2005/0165429 A1 | 7/2005 | Douglas et al. |
| 2005/0216039 A1 | 9/2005 | Lederman |
| 2005/0251177 A1 | 11/2005 | Saadat et al. |
| 2005/0251183 A1 | 11/2005 | Buckman et al. |
| 2005/0288786 A1 | 12/2005 | Chanduszko |
| 2006/0020275 A1 | 1/2006 | Goldfarb et al. |
| 2006/0089671 A1 | 4/2006 | Goldfarb et al. |
| 2006/0100649 A1 | 5/2006 | Hart |
| 2006/0122647 A1 | 6/2006 | Callaghan et al. |
| 2006/0142694 A1 | 6/2006 | Bednarek et al. |
| 2006/0173251 A1 | 8/2006 | Govari et al. |
| 2006/0178700 A1 | 8/2006 | Quinn |
| 2006/0224169 A1 | 10/2006 | Weisenburgh et al. |
| 2007/0010800 A1 | 1/2007 | Weitzner et al. |
| 2007/0010877 A1 | 1/2007 | Salahieh et al. |
| 2007/0016286 A1 | 1/2007 | Herrmann et al. |
| 2007/0021779 A1 | 1/2007 | Garvin et al. |
| 2007/0032807 A1 | 2/2007 | Ortiz et al. |
| 2007/0093857 A1 | 4/2007 | Rogers et al. |
| 2007/0093890 A1 | 4/2007 | Ellasen et al. |
| 2007/0156197 A1 | 7/2007 | Root et al. |
| 2007/0191154 A1 | 8/2007 | Genereux et al. |
| 2007/0197858 A1 | 8/2007 | Goldfarb et al. |
| 2007/0198038 A1 | 8/2007 | Cohen et al. |
| 2007/0265700 A1 | 11/2007 | Ellasen et al. |
| 2007/0282414 A1 | 12/2007 | Soltis et al. |
| 2007/0293943 A1 | 12/2007 | Quinn |
| 2007/0299387 A1 | 12/2007 | Williams et al. |
| 2007/0299424 A1 | 12/2007 | Cumming et al. |
| 2008/0039743 A1 | 2/2008 | Fox et al. |
| 2008/0039953 A1 | 2/2008 | Davis et al. |
| 2008/0065149 A1 | 3/2008 | Thielen et al. |
| 2008/0077144 A1 | 3/2008 | Crofford |
| 2008/0091169 A1 | 4/2008 | Heideman et al. |
| 2008/0140089 A1 | 6/2008 | Kogiso et al. |
| 2008/0147093 A1 | 6/2008 | Roskopf et al. |
| 2008/0147112 A1 | 6/2008 | Sheets et al. |
| 2008/0149685 A1 | 6/2008 | Smith et al. |
| 2008/0167713 A1 | 7/2008 | Bolling |
| 2008/0177300 A1 | 7/2008 | Mas et al. |
| 2008/0208332 A1 | 8/2008 | Lamphere et al. |
| 2008/0221672 A1 | 9/2008 | Lamphere et al. |
| 2008/0255427 A1 | 10/2008 | Satake et al. |
| 2008/0281411 A1 | 11/2008 | Berreklouw |
| 2008/0287862 A1 | 11/2008 | Weitzner et al. |
| 2008/0294247 A1 | 11/2008 | Yang et al. |
| 2008/0312506 A1 | 12/2008 | Spivey et al. |
| 2008/0319455 A1 | 12/2008 | Harris et al. |
| 2009/0005863 A1 | 1/2009 | Goetz et al. |
| 2009/0024110 A1 | 1/2009 | Heideman et al. |
| 2009/0099554 A1 | 4/2009 | Forster et al. |
| 2009/0131880 A1 | 5/2009 | Speziali et al. |
| 2009/0156995 A1 | 6/2009 | Martin et al. |
| 2009/0163934 A1 | 6/2009 | Raschdorf, Jr. et al. |
| 2009/0166913 A1 | 7/2009 | Guo et al. |
| 2009/0177266 A1 | 7/2009 | Powell et al. |
| 2009/0234280 A1 | 9/2009 | Tah et al. |
| 2009/0275902 A1 | 11/2009 | Heeps et al. |
| 2009/0287304 A1 | 11/2009 | Dahlgren et al. |
| 2010/0022823 A1 | 1/2010 | Goldfarb et al. |
| 2010/0057192 A1 | 3/2010 | Celermajer |
| 2010/0069834 A1 | 3/2010 | Schultz |
| 2010/0094317 A1 | 4/2010 | Goldfarb et al. |
| 2010/0106141 A1 | 4/2010 | Osypka et al. |
| 2010/0121434 A1 | 5/2010 | Paul et al. |
| 2010/0249497 A1 | 9/2010 | Peine et al. |
| 2010/0298929 A1 | 11/2010 | Thornton et al. |
| 2010/0324595 A1 | 12/2010 | Linder et al. |
| 2011/0082538 A1 | 4/2011 | Dahlgren et al. |
| 2011/0137410 A1 | 6/2011 | Hacohen |
| 2011/0245855 A1 | 10/2011 | Matsuoka et al. |
| 2011/0257723 A1 | 10/2011 | McNamara |
| 2011/0295281 A1 | 12/2011 | Mizumoto et al. |
| 2012/0022633 A1 | 1/2012 | Olson et al. |
| 2012/0089125 A1 | 4/2012 | Scheibe et al. |
| 2012/0109160 A1 | 5/2012 | Martinez et al. |
| 2012/0116419 A1 | 5/2012 | Sigmon, Jr. |
| 2012/0209318 A1 | 8/2012 | Qadeer |
| 2012/0239142 A1 | 9/2012 | Liu et al. |
| 2012/0277853 A1 | 11/2012 | Rothstein |
| 2013/0035759 A1 | 2/2013 | Gross et al. |
| 2013/0041314 A1 | 2/2013 | Dillon |
| 2013/0046152 A1 | 2/2013 | Najafi et al. |
| 2013/0066341 A1 | 3/2013 | Ketai et al. |
| 2013/0066342 A1 | 3/2013 | Dell et al. |
| 2013/0072945 A1 | 3/2013 | Terada |
| 2013/0073034 A1 | 3/2013 | Wilson et al. |
| 2013/0110254 A1 | 5/2013 | Osborne |
| 2013/0190798 A1 | 7/2013 | Kapadia |
| 2013/0190861 A1 | 7/2013 | Chau et al. |

(56) References Cited

U.S. PATENT DOCUMENTS

| | | |
|---|---|---|
| 2013/0268069 A1 | 10/2013 | Zakai et al. |
| 2013/0282059 A1 | 10/2013 | Ketai et al. |
| 2013/0304197 A1 | 11/2013 | Buchbinder et al. |
| 2013/0325110 A1 | 12/2013 | Khalil et al. |
| 2014/0031928 A1 | 1/2014 | Murphy et al. |
| 2014/0046433 A1 | 2/2014 | Kovalsky |
| 2014/0046434 A1 | 2/2014 | Rolando et al. |
| 2014/0052237 A1 | 2/2014 | Lane et al. |
| 2014/0058411 A1 | 2/2014 | Soutorine et al. |
| 2014/0067048 A1 | 3/2014 | Chau et al. |
| 2014/0067052 A1 | 3/2014 | Chau et al. |
| 2014/0094903 A1 | 4/2014 | Miller et al. |
| 2014/0135685 A1 | 5/2014 | Kabe et al. |
| 2014/0194975 A1 | 7/2014 | Quill et al. |
| 2014/0200662 A1 | 7/2014 | Eftel et al. |
| 2014/0207231 A1 | 7/2014 | Hacohen et al. |
| 2014/0236198 A1 | 8/2014 | Goldfarb et al. |
| 2014/0243968 A1 | 8/2014 | Padala |
| 2014/0251042 A1 | 9/2014 | Asselin et al. |
| 2014/0277404 A1 | 9/2014 | Wilson et al. |
| 2014/0277411 A1 | 9/2014 | Bortlein et al. |
| 2014/0277427 A1 | 9/2014 | Ratz et al. |
| 2014/0316428 A1 | 10/2014 | Golan |
| 2014/0324164 A1 | 10/2014 | Gross et al. |
| 2014/0330368 A1 | 11/2014 | Gloss et al. |
| 2014/0336751 A1 | 11/2014 | Kramer |
| 2014/0371843 A1 | 12/2014 | Wilson et al. |
| 2015/0039084 A1 | 2/2015 | Levi et al. |
| 2015/0057704 A1 | 2/2015 | Takahashi |
| 2015/0094802 A1 | 4/2015 | Buchbinder et al. |
| 2015/0100116 A1 | 4/2015 | Mohl et al. |
| 2015/0105808 A1 | 4/2015 | Gordon et al. |
| 2015/0148896 A1 | 5/2015 | Karapetian et al. |
| 2015/0157268 A1 | 6/2015 | Winshtein et al. |
| 2015/0196390 A1 | 7/2015 | Ma et al. |
| 2015/0223793 A1 | 8/2015 | Goldfarb et al. |
| 2015/0230919 A1 | 8/2015 | Chau et al. |
| 2015/0238313 A1 | 8/2015 | Spence et al. |
| 2015/0257757 A1 | 9/2015 | Powers et al. |
| 2015/0257877 A1 | 9/2015 | Hernandez |
| 2015/0257883 A1 | 9/2015 | Basude et al. |
| 2015/0297346 A1 | 10/2015 | Duffy et al. |
| 2015/0305867 A1* | 10/2015 | Liu ............... A61F 2/2436 |
| 2015/0313592 A1 | 11/2015 | Coillard-Lavirotte et al. |
| 2015/0351904 A1 | 12/2015 | Cooper et al. |
| 2015/0366666 A1 | 12/2015 | Khairkhahan et al. |
| 2016/0008129 A1 | 1/2016 | Siegel |
| 2016/0008131 A1 | 1/2016 | Christianson et al. |
| 2016/0022970 A1 | 1/2016 | Forcucci et al. |
| 2016/0051796 A1 | 2/2016 | Kanemasa et al. |
| 2016/0074164 A1 | 3/2016 | Naor |
| 2016/0074165 A1 | 3/2016 | Spence et al. |
| 2016/0106539 A1 | 4/2016 | Buchbinder et al. |
| 2016/0113762 A1 | 4/2016 | Clague et al. |
| 2016/0113764 A1 | 4/2016 | Sheahan et al. |
| 2016/0113766 A1 | 4/2016 | Ganesan et al. |
| 2016/0155987 A1 | 6/2016 | Yoo et al. |
| 2016/0158497 A1* | 6/2016 | Tran ............... A61F 2/2436 604/95.04 |
| 2016/0174979 A1 | 6/2016 | Wei |
| 2016/0174981 A1 | 6/2016 | Fago et al. |
| 2016/0242906 A1 | 8/2016 | Morriss et al. |
| 2016/0287387 A1 | 10/2016 | Wei |
| 2016/0302811 A1 | 10/2016 | Rodriguez-Navarro et al. |
| 2016/0310701 A1* | 10/2016 | Pai ............... A61B 18/1492 |
| 2016/0317290 A1 | 11/2016 | Chau et al. |
| 2016/0331523 A1 | 11/2016 | Chau et al. |
| 2016/0345947 A1* | 12/2016 | Salahieh ............ A61B 17/00234 |
| 2016/0354082 A1 | 12/2016 | Oz et al. |
| 2017/0020521 A1 | 1/2017 | Krone et al. |
| 2017/0035561 A1 | 2/2017 | Rowe et al. |
| 2017/0035566 A1 | 2/2017 | Krone et al. |
| 2017/0042456 A1 | 2/2017 | Budiman |
| 2017/0042678 A1 | 2/2017 | Ganesan et al. |
| 2017/0049455 A1 | 2/2017 | Seguin |
| 2017/0100119 A1 | 4/2017 | Baird et al. |
| 2017/0100236 A1 | 4/2017 | Robertson et al. |
| 2017/0224955 A1 | 8/2017 | Douglas et al. |
| 2017/0239048 A1 | 8/2017 | Goldfarb et al. |
| 2017/0252154 A1 | 9/2017 | Tubishevitz et al. |
| 2017/0266413 A1 | 9/2017 | Khuu et al. |
| 2017/0281330 A1 | 10/2017 | Liljegren et al. |
| 2017/0348102 A1 | 12/2017 | Cousins et al. |
| 2018/0008311 A1 | 1/2018 | Shiroff et al. |
| 2018/0021044 A1 | 1/2018 | Miller et al. |
| 2018/0021129 A1 | 1/2018 | Peterson et al. |
| 2018/0021134 A1 | 1/2018 | McNiven et al. |
| 2018/0021546 A1* | 1/2018 | McDermott ...... A61M 25/0147 604/95.04 |
| 2018/0071487 A1 | 3/2018 | Khuu et al. |
| 2018/0078271 A1 | 3/2018 | Thrasher, III |
| 2018/0078361 A1 | 3/2018 | Naor et al. |
| 2018/0092661 A1 | 4/2018 | Prabhu |
| 2018/0126124 A1 | 5/2018 | Winston et al. |
| 2018/0133008 A1 | 5/2018 | Kizuka et al. |
| 2018/0146964 A1 | 5/2018 | Garcia et al. |
| 2018/0146966 A1 | 5/2018 | Hernandez et al. |
| 2018/0153552 A1 | 6/2018 | King et al. |
| 2018/0161159 A1 | 6/2018 | Lee et al. |
| 2018/0168803 A1 | 6/2018 | Pesce et al. |
| 2018/0185154 A1 | 7/2018 | Cao |
| 2018/0221147 A1 | 8/2018 | Ganesan et al. |
| 2018/0235657 A1 | 8/2018 | Abunassar |
| 2018/0243086 A1 | 8/2018 | Barbarino et al. |
| 2018/0258665 A1 | 9/2018 | Reddy et al. |
| 2018/0263767 A1 | 9/2018 | Chau et al. |
| 2018/0296326 A1 | 10/2018 | Dixon et al. |
| 2018/0296327 A1 | 10/2018 | Dixon et al. |
| 2018/0296328 A1 | 10/2018 | Dixon et al. |
| 2018/0296329 A1 | 10/2018 | Dixon et al. |
| 2018/0296330 A1 | 10/2018 | Dixon et al. |
| 2018/0296331 A1 | 10/2018 | Dixon et al. |
| 2018/0296332 A1 | 10/2018 | Dixon et al. |
| 2018/0296333 A1 | 10/2018 | Dixon et al. |
| 2018/0296334 A1 | 10/2018 | Dixon et al. |
| 2018/0318079 A1* | 11/2018 | Patel ............... A61M 25/0147 |
| 2018/0325661 A1 | 11/2018 | Delgado et al. |
| 2018/0325671 A1 | 11/2018 | Abunassar et al. |
| 2018/0333259 A1 | 11/2018 | Dibie |
| 2018/0344457 A1 | 12/2018 | Gross et al. |
| 2018/0353181 A1 | 12/2018 | Wei |
| 2019/0000613 A1 | 1/2019 | Delgado et al. |
| 2019/0000623 A1 | 1/2019 | Pan et al. |
| 2019/0008642 A1 | 1/2019 | Delgado et al. |
| 2019/0008643 A1 | 1/2019 | Delgado et al. |
| 2019/0015199 A1 | 1/2019 | Delgado et al. |
| 2019/0015200 A1 | 1/2019 | Delgado et al. |
| 2019/0015207 A1 | 1/2019 | Delgado et al. |
| 2019/0015208 A1 | 1/2019 | Delgado et al. |
| 2019/0021851 A1 | 1/2019 | Delgado et al. |
| 2019/0021852 A1 | 1/2019 | Delgado et al. |
| 2019/0029498 A1 | 1/2019 | Mankowski et al. |
| 2019/0029810 A1 | 1/2019 | Delgado et al. |
| 2019/0029813 A1 | 1/2019 | Delgado et al. |
| 2019/0030285 A1 | 1/2019 | Prabhu et al. |
| 2019/0053810 A1 | 2/2019 | Griffin |
| 2019/0060058 A1 | 2/2019 | Delgado et al. |
| 2019/0060059 A1 | 2/2019 | Delgado et al. |
| 2019/0060072 A1 | 2/2019 | Zeng |
| 2019/0060073 A1 | 2/2019 | Delgado et al. |
| 2019/0060074 A1 | 2/2019 | Delgado et al. |
| 2019/0060075 A1 | 2/2019 | Delgado et al. |
| 2019/0069991 A1 | 3/2019 | Metchik et al. |
| 2019/0069992 A1 | 3/2019 | Delgado et al. |
| 2019/0069993 A1 | 3/2019 | Delgado et al. |
| 2019/0105156 A1 | 4/2019 | He et al. |
| 2019/0111239 A1 | 4/2019 | Bolduc et al. |
| 2019/0117113 A1 | 4/2019 | Curran |
| 2019/0142589 A1 | 5/2019 | Basude |
| 2019/0159782 A1 | 5/2019 | Kamaraj et al. |
| 2019/0167197 A1 | 6/2019 | Abunassar et al. |
| 2019/0183644 A1 | 6/2019 | Hacohen |
| 2019/0192296 A1 | 6/2019 | Schwartz et al. |
| 2019/0209323 A1 | 7/2019 | Metchik et al. |

(56) References Cited

U.S. PATENT DOCUMENTS

| | | |
|---|---|---|
| 2019/0261995 A1 | 8/2019 | Goldfarb et al. |
| 2019/0261996 A1 | 8/2019 | Goldfarb et al. |
| 2019/0261997 A1 | 8/2019 | Goldfarb et al. |
| 2019/0314155 A1 | 10/2019 | Franklin et al. |
| 2019/0321166 A1 | 10/2019 | Freschauf et al. |
| 2020/0113683 A1 | 4/2020 | Dale et al. |
| 2020/0138569 A1 | 5/2020 | Basude et al. |
| 2020/0205979 A1 | 7/2020 | O'Carroll et al. |
| 2020/0237512 A1 | 7/2020 | McCann et al. |
| 2020/0337842 A1 | 10/2020 | Metchik et al. |
| 2020/0352717 A1 | 11/2020 | Kheradvar et al. |
| 2020/0360054 A1 | 11/2020 | Walsh et al. |
| 2020/0360132 A1 | 11/2020 | Spence |
| 2020/0368016 A1 | 11/2020 | Pesce et al. |
| 2021/0022850 A1 | 1/2021 | Basude et al. |
| 2021/0059680 A1 | 3/2021 | Lin et al. |
| 2021/0169650 A1 | 6/2021 | Dai et al. |
| 2021/0186698 A1 | 6/2021 | Abunassar et al. |
| 2021/0251757 A1 | 8/2021 | Siegel et al. |
| 2021/0259835 A1 | 8/2021 | Tyler, II et al. |
| 2021/0267781 A1 | 9/2021 | Metchik et al. |
| 2021/0307900 A1 | 10/2021 | Hacohen |
| 2021/0330456 A1 | 10/2021 | Hacohen et al. |
| 2021/0338418 A1 | 11/2021 | Feld |
| 2021/0361238 A1 | 11/2021 | Bak-Boychuk et al. |
| 2021/0361416 A1 | 11/2021 | Stearns |
| 2021/0361422 A1 | 11/2021 | Gross et al. |
| 2021/0361428 A1 | 11/2021 | Dixon |
| 2021/0378818 A1 | 12/2021 | Manash et al. |
| 2021/0401434 A1 | 12/2021 | Tien et al. |
| 2022/0039943 A1 | 2/2022 | Phan |
| 2022/0039954 A1 | 2/2022 | Nia et al. |
| 2022/0071767 A1 | 3/2022 | Dixon et al. |
| 2022/0133327 A1 | 5/2022 | Zhang et al. |
| 2022/0142780 A1 | 5/2022 | Zhang et al. |
| 2022/0142781 A1 | 5/2022 | Zhang et al. |
| 2022/0226108 A1 | 7/2022 | Freschauf et al. |
| 2022/0233312 A1 | 7/2022 | Delgado et al. |
| 2022/0257196 A1 | 8/2022 | Massmann |
| 2022/0287841 A1 | 9/2022 | Freschauf et al. |
| 2022/0296248 A1 | 9/2022 | Abunassar et al. |
| 2022/0313433 A1 | 10/2022 | Ma et al. |
| 2023/0014540 A1 | 1/2023 | Metchik et al. |
| 2023/0149170 A1 | 5/2023 | Giese et al. |
| 2023/0218291 A1 | 7/2023 | Zarbatany et al. |
| 2023/0270549 A1 | 8/2023 | Guidotti et al. |
| 2024/0148505 A1 | 5/2024 | Datta et al. |

FOREIGN PATENT DOCUMENTS

| | | |
|---|---|---|
| CN | 106491245 A | 3/2017 |
| CN | 107789017 A | 3/2018 |
| CN | 109953779 A | 7/2019 |
| CN | 110338857 A | 10/2019 |
| CN | 110495972 A | 11/2019 |
| CN | 110537946 A | 12/2019 |
| CN | 110664515 A | 1/2020 |
| CN | 209996540 U | 1/2020 |
| CN | 211243911 U | 8/2020 |
| CN | 211723546 U | 10/2020 |
| CN | 111870398 A | 11/2020 |
| CN | 111904660 A | 11/2020 |
| CN | 112120831 A | 12/2020 |
| CN | 112168427 A | 1/2021 |
| CN | 112190367 A | 1/2021 |
| CN | 212346813 U | 1/2021 |
| CN | 212415988 U | 1/2021 |
| CN | 212490263 U | 2/2021 |
| CN | 113476182 A | 10/2021 |
| CN | 113855328 A | 12/2021 |
| CN | 215019733 U | 12/2021 |
| EP | 0098100 A2 | 1/1984 |
| FR | 2146050 A5 | 2/1973 |
| FR | 9711600 | 3/1997 |
| WO | 2014064694 A2 | 5/2014 |
| WO | 2017015632 A1 | 1/2017 |
| WO | 2018013856 A1 | 1/2018 |
| WO | 2018050200 A1 | 3/2018 |
| WO | 2018050203 A1 | 3/2018 |
| WO | 2018195015 A1 | 10/2018 |
| WO | 2018195201 A1 | 10/2018 |
| WO | 2018195215 A2 | 10/2018 |
| WO | 2019139904 A1 | 7/2019 |
| WO | 2020106705 A1 | 5/2020 |
| WO | 2020106827 A1 | 5/2020 |
| WO | 2020112622 A1 | 6/2020 |
| WO | 2020167677 A1 | 8/2020 |
| WO | 2020168081 A1 | 8/2020 |
| WO | 2020172224 A1 | 8/2020 |
| WO | 2020176410 A1 | 9/2020 |
| WO | 2021196580 A1 | 10/2021 |
| WO | 2021227412 A1 | 11/2021 |
| WO | 2022006087 A2 | 1/2022 |
| WO | 2022036209 A1 | 2/2022 |
| WO | 2022051241 A1 | 3/2022 |
| WO | 2022052506 A1 | 3/2022 |
| WO | 2022068188 A1 | 4/2022 |
| WO | 2022101817 A2 | 5/2022 |
| WO | 2022140175 A1 | 6/2022 |
| WO | 2022153131 A1 | 7/2022 |
| WO | 2022155298 A2 | 7/2022 |
| WO | 2022157592 A1 | 7/2022 |
| WO | 2022212172 A1 | 10/2022 |
| WO | 2023003755 A1 | 1/2023 |
| WO | 2023004098 A1 | 1/2023 |
| WO | 2023278663 A2 | 1/2023 |
| WO | 2023288003 A1 | 1/2023 |

OTHER PUBLICATIONS

Al-Khaja et al., "Eleven years' experience with Carpentier-Edwards biological valves in relation to survival and complications", European Journal of Cardio-Thoracic Surgery, vol. 3, No. 4, pp. 305-311, Jul. 1, 1989, Springer-Verlag, Berlin, Germany.

Almagor et al., "Balloon Expandable Stent Implantation in Stenotic Right Heart Valved Conduits", Journal of the American College of Cardiology, vol. 16, No. 5, pp. 1310-1314, Nov. 15, 1990.

Andersen, et al., "Transluminal implantation of artificial heart valves. Description of a new expandable aortic valve and initial results with implantation by catheter technique in closed chest pigs", European Heart Journal, vol. 13, No. 5, pp. 704-708, May 1, 1992, The European Society of Cardiology, Oxford University Press, United Kingdom.

Andersen, H.R. "History of Percutaneous Aortic Valve Prosthesis," Herz, vol. 34., No. 5, pp. 343-346, Aug. 2009, Urban & Vogel, Germany.

Batista RJ et al., "Partial left ventriculectomy to treat end-stage heart disease", Ann Thorac Surg., vol. 64, Issue—3, pp. 634-638, Sep. 1997.

Beall AC Jr. et al., "Clinical experience with a dacron velour-covered teflon-disc mitral-valve prosthesis", Ann Thorac Surg., vol. 5, Issue 5, pp. 402-410, May 1968.

Benchimol et al., "Simultaneous left ventricular echocardiography and aortic blood velocity during rapid right ventricular pacing in man", The American Journal of the Medical Sciences, vol. 273, No. 1, pp. 55-62, Jan.-Feb. 1977, Elsevier, United States.

Dake et al., "Transluminal Placement of Endovascular Stent-Grafts for the Treatment of Descending Thoracic Aortic Aneurysms", The New England Journal of Medicine, vol. 331, No. 26, pp. 1729-1734, Dec. 29, 1994.

Dotter et al., "Transluminal Treatment of Arteriosclerotic Obstruction: Description of a New Technic and a Preliminary Report of Its Application", Circulation, vol. XXX, No. 30, pp. 654-670, Nov. 1, 1964, Lippincott Williams & Wilkins, Philadelphia, PA.

Fucci et al., "Improved results with mitral valve repair using new surgical techniques", Eur J Cardiothorac Surg. 1995;Issue 9, vol. 11, pp. 621-626.

Inoune et al., "Clinical application of transvenous mitral commissurotomy by a new balloon catheter," The Journal of Thoracic and Cardiovascular Surgery, vol. 87, No. 3, pp. 394-402, Mar. 1984, Elsevier, United States.

(56) References Cited

OTHER PUBLICATIONS

Kolata, Gina "Device That Opens Clogged Arteries Gets a Failing Grade in a New Study", The New York Times, Jan. 3, 1991, pp. 1-2 [online], [retrieved on Jul. 29, 2009]. Retrieved from the Internet <URL:http://www.nytimes.com/1991/01/03/health/device-that-opens-clogged-arteries-gets-a-faill . . . .

Lawrence, Jr., et al., "Percutaneous Endovascular Graft: Experimental Evaluation", Cardiovascular Radiology 163, pp. 357-360, May 1987.

Maisano F et al., 'The edge-to-edge technique: a simplified method to correct mitral insufficiency', Eur J Cardiothorac Surg., vol. 13, Issue—3, pp. 240-245, Mar. 1998.

Pavcnik et al. "Development and Initial Experimental Evaluation of a Prosthetic Aortic Valve for Transcatheter Placement," Radiology, vol. 183, No. 1, pp. 151-154, Apr. 1, 1992. Elsevier, United States.

Porstmann et al., "Der Verschluß des Ductus Arteriosus Persistens Ohne Thorakotomie", Thoraxchirurgie Vaskuläre Chirurgie, Band 15, Heft 2, Stuttgart, im Apr. 1967, pp. 199-203.

Praz et al., "Compassionate use of the PASCAL transcatheter mitral valve repair system for patients with severe mitral regurgitation: a multicentre, prospective, observational, first-in-man study," Lancet, vol. 390, pp. 773-780, Aug. 19, 2017, Lancet, United States.

Reul RM et al., "Mitral valve reconstruction for mitral insufficiency", Prog Cardiovasc Dis., vol. 39, Issue—6, May-Jun. 1997.

Rösch et al., "The Birth, Early Years and Future of Interventional Radiology," Journal of Vascular and Interventional Radiology, vol. 14, No. 7, pp. 841-853, Jul. 1, 2003, Elsevier, United States.

Sabbah et al., "Mechanical Factors in the Degeneration of Porcine Bioprosthetic Valves: An Overview", Journal of Cardiac Surgery, vol. 4, No. 4, pp. 302-309, Dec. 1989.

Selby et al., "Experience with New Retrieval Forceps for Foreign Body Removal in the Vascular, Urinary, and Biliary Systems", Radiology, vol. 176, No. 2, pp. 535-538, Jul. 31, 1990, Radiological Society of North America, Oak Brook, IL.

Serruys et al., "Stenting of coronary arteries. Are we the sorcerer's apprentice?", European Heart Journal, vol. 10, No. 9 pp. 774-782, Sep. 1, 1989, The European Society of Cardiology, Oxford University Press, United Kingdom.

Sigwart, Ulrich, "An Overview of Intravascular Stents: Old and New," Textbook of Interventional Cardiology, Second Edition, chapter 48, pp. 803-815, © 1994, W.B. Saunders Company, Philadelphia, PA.

Uchida et al., "Modifications of Gianturco Expandable Wire Stents", Technical Note, American Roentgen Ray Society, pp. 1185-1187, May 1988.

Umaña JP et al., Bow-tie' mitral valve repair: an adjuvant technique for ischemic mitral regurgitation', Ann Thorac Surg., vol. 66, Issue—6, pp. 1640-1646, Nov. 1998.

Urban, Philip MD, "Coronary Artery Stenting", pp. 5-47, © 1991, ISBN: 2-88049-054-5, Editions Medecine et Hygiene, Geneva, Switzerland.

Watt et al., "Intravenous adenosine in the treatment of supraventricular rachycardia: a dose-ranging study and interaction with dipyridamole", British Journal of Clinical Pharmacology, vol. 21, No. 2, pp. 227-230, Feb. 1986, British Pharmacological Society, London, United Kingdom.

Wheatley, David J., "Valve Prosthesis", Rob & Smith's Operative Surgery-Cardiac Surgery, vol. 91, No. 2, pp. 415-424, Feb. 1, 1987, Butterworth Scientific, London, UK.

Grasso et al., "The PASCAL transcatheter mitral valve repair system for the treatment of mitral regurgitation: another piece to the puzzle of edge-to-edge technique", Journal of Thoracic Disease, vol. 9, No. 12, pp. 4856-4859, Dec. 2017, doi: 10.21037/jtd.2017.10.156, AME Publishing Company, Hong Kong, China.

\* cited by examiner

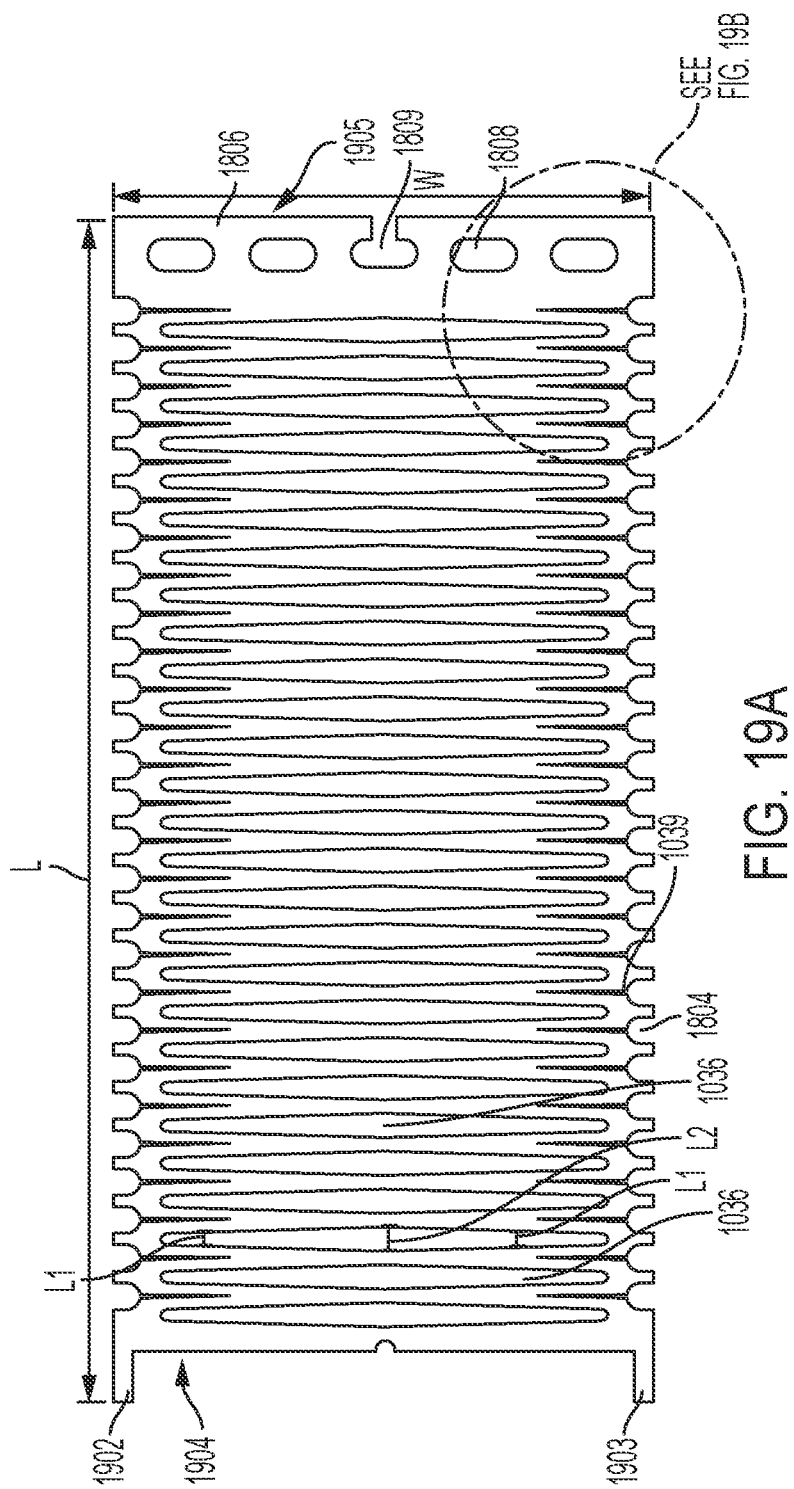

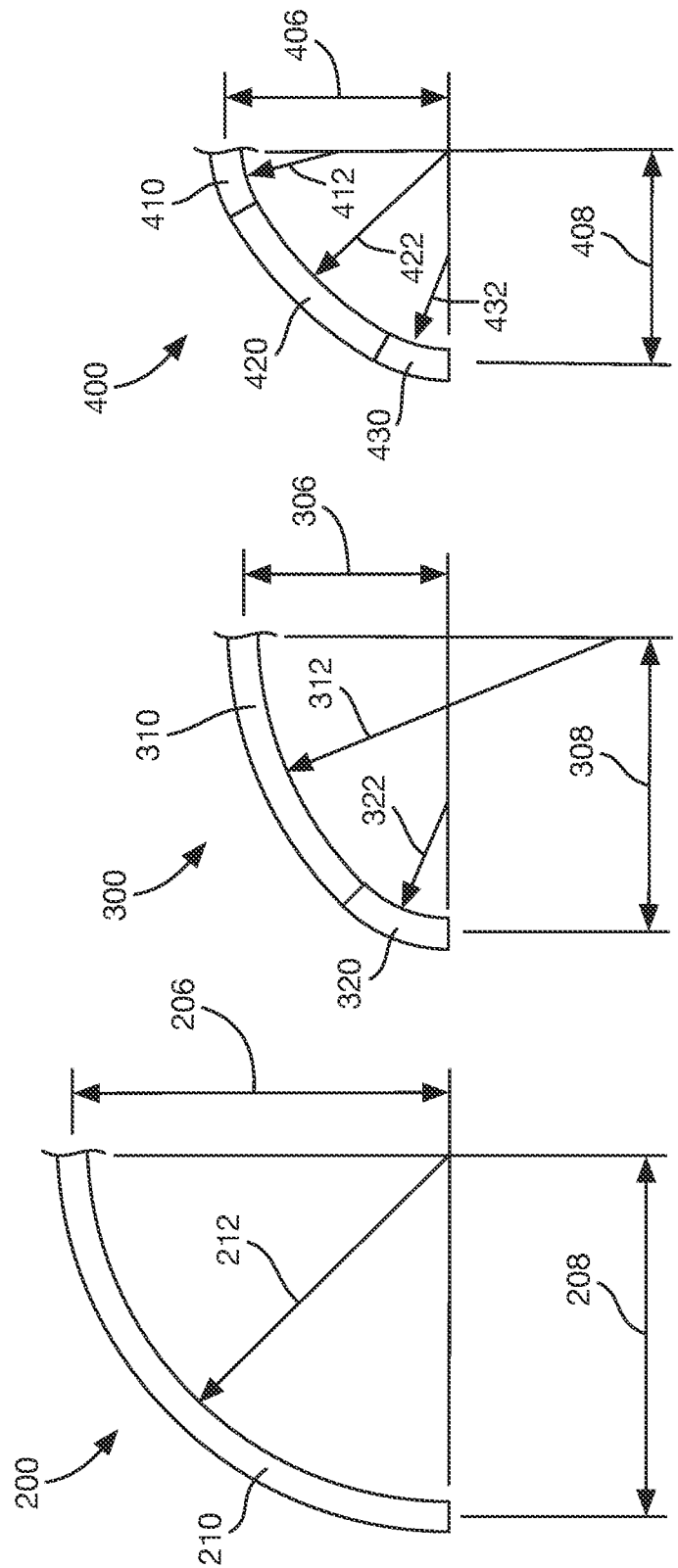

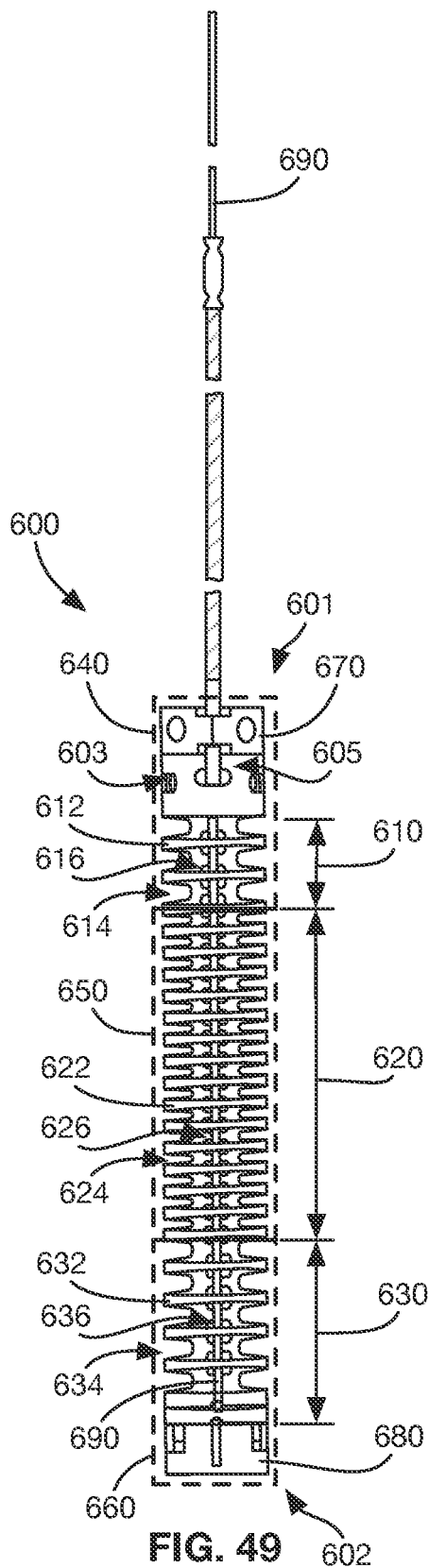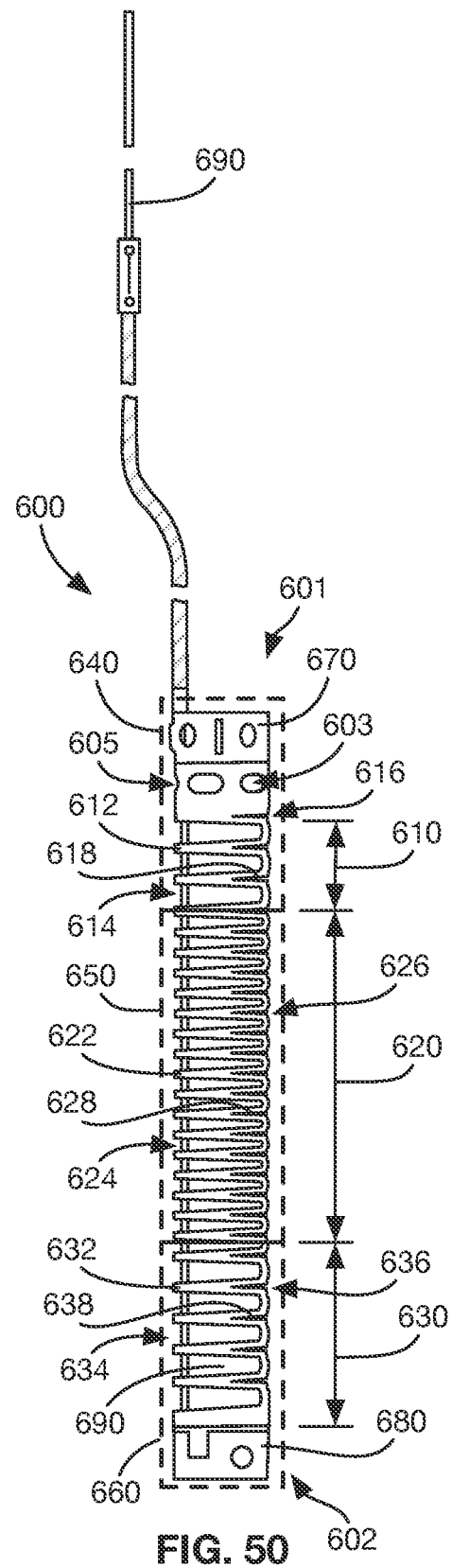

DEPLOYMENT TOOLS AND METHODS FOR DELIVERING A DEVICE TO A NATIVE HEART VALVE

RELATED APPLICATION

The present application is a continuation of International Patent Application No. PCT/US2019/062194, filed Nov. 19, 2019, titled "Deployment Tools and Methods for Delivering a Device to a Native Heart Valve," which claims the benefit of U.S. Provisional Patent Application Ser. No. 62/770,071, filed on Nov. 20, 2018, titled "Deployment Tools and Methods for Delivering a Device to a Native Heart Valve," which are incorporated herein by reference in their entirety for all purposes.

BACKGROUND OF THE INVENTION

The native heart valves (i.e., the aortic, pulmonary, tricuspid, and mitral valves) serve critical functions in assuring the forward flow of an adequate supply of blood through the cardiovascular system. These heart valves can be damaged, and thus rendered less effective, by congenital malformations, inflammatory processes, infectious conditions, disease, etc. Such damage to the valves can result in serious cardiovascular compromise or death. Damaged valves can be surgically repaired or replaced during open heart surgery. However, open heart surgeries are highly invasive and complications may occur. Transvascular techniques can be used to introduce and implant prosthetic devices in a manner that is much less invasive than open heart surgery. As one example, a transvascular technique useable for accessing the native mitral and aortic valves is the trans-septal technique. The trans-septal technique comprises advancing a catheter into the right atrium (e.g., inserting a catheter into the right femoral vein, up the inferior vena cava and into the right atrium). The septum is then punctured, and the catheter passed into the left atrium. A similar transvascular technique can be used to implant a prosthetic device within the tricuspid valve that begins similarly to the trans-septal technique but stops short of puncturing the septum and instead turns the delivery catheter toward the tricuspid valve in the right atrium.

A healthy heart has a generally conical shape that tapers to a lower apex. The heart is four-chambered and comprises the left atrium, right atrium, left ventricle, and right ventricle. The left and right sides of the heart are separated by a wall generally referred to as the septum. The native mitral valve of the human heart connects the left atrium to the left ventricle. The mitral valve has a very different anatomy than other native heart valves. The mitral valve includes an annulus portion, which is an annular portion of the native valve tissue surrounding the mitral valve orifice, and a pair of cusps, or leaflets, extending downward from the annulus into the left ventricle. The mitral valve annulus can form a "D"-shaped, oval, or otherwise out-of-round cross-sectional shape having major and minor axes. The anterior leaflet can be larger than the posterior leaflet, forming a generally "C"-shaped boundary between the abutting sides of the leaflets when they are closed together.

When operating properly, the anterior leaflet and the posterior leaflet function together as a one-way valve to allow blood to flow only from the left atrium to the left ventricle. The left atrium receives oxygenated blood from the pulmonary veins. When the muscles of the left atrium contract and the left ventricle dilates (also referred to as "ventricular diastole" or "diastole"), the oxygenated blood that is collected in the left atrium flows into the left ventricle. When the muscles of the left atrium relax and the muscles of the left ventricle contract (also referred to as "ventricular systole" or "systole"), the increased blood pressure in the left ventricle urges the sides of the two leaflets together, thereby closing the one-way mitral valve so that blood cannot flow back to the left atrium and is instead expelled out of the left ventricle through the aortic valve. To prevent the two leaflets from prolapsing under pressure and folding back through the mitral annulus toward the left atrium, a plurality of fibrous cords called chordae tendineae tether the leaflets to papillary muscles in the left ventricle.

Valvular regurgitation involves the valve improperly allowing some blood to flow in the wrong direction through the valve. For example, mitral regurgitation occurs when the native mitral valve fails to close properly and blood flows into the left atrium from the left ventricle during the systolic phase of heart contraction. Mitral regurgitation is one of the most common forms of valvular heart disease. Mitral regurgitation can have many different causes, such as leaflet prolapse, dysfunctional papillary muscles, stretching of the mitral valve annulus resulting from dilation of the left ventricle, more than one of these, etc. Mitral regurgitation at a central portion of the leaflets can be referred to as central jet mitral regurgitation and mitral regurgitation nearer to one commissure (i.e., location where the leaflets meet) of the leaflets can be referred to as eccentric jet mitral regurgitation. Central jet regurgitation occurs when the edges of the leaflets do not meet in the middle and thus the valve does not close, and regurgitation is present.

SUMMARY

This summary is meant to provide some examples and is not intended to be limiting of the scope of the invention in any way. For example, any feature included in an example of this summary is not required by the claims, unless the claims explicitly recite the features. Also, the features, components, steps, concepts, etc. described in examples in this summary and elsewhere in this disclosure can be combined in a variety of ways. Various features and steps as described elsewhere in this disclosure may be included in the examples summarized here.

A flexible delivery catheter can be used to deploy valve repair and replacement devices at an implant site for the repair or replacement of poorly functioning native heart valves. Such a catheter can include a flexible tube having a plurality of links. A control wire (e.g., a pull wire, etc.) can be connected to the plurality of links, such that applying tension to the control wire causes the flexible tube to bend.

In one example embodiment, a delivery catheter includes a having a main lumen, a control wire lumen, a plurality of links, and a control wire. Each link is aligned with and connected to at least one adjacent link with a slot formed between each pair of adjacent links. A top portion of each link is narrower than a bottom portion of each link when the links are viewed from a side. Each link includes an orifice at the bottom of the link. Each link includes at least one slit. Each slit begins at and extends upward along at least a portion of the link. The control wire is connected to the plurality of links. Applying tension to the control wire causes the distal region of the catheter to bend.

In one example embodiment, a delivery catheter includes a flexible tube, a first ring, a second ring, a single control wire, a coil sleeve, and a plurality of links. The flexible tube includes a main lumen and a control wire lumen. The first ring is in a distal region of the flexible tube. The second ring is in the distal region of the flexible tube and is spaced apart from the first ring. The single control wire is in the control wire lumen and is connected to the first ring. The plurality of links are between the first ring and the second ring. The coil sleeve is in the control wire lumen around the control wire. A portion of the single control wire that extends from the second ring and to the first ring is not covered by the coil sleeve. Applying tension to the single control wire causes the distal region of the flexible tube to bend.

A delivery catheter includes a flexible tube, a first ring, a second ring, a single control wire, a plurality of links, and a coil sleeve. The flexible tube has a main lumen and a control wire lumen. The first and second rings are spaced apart in a distal region of the flexible tube. The single control wire is in the control wire lumen and is connected to the first ring. The plurality of links are disposed in the distal region of the flexible tube between the first ring and the second ring. The links are cut from a single piece of material, such that each link is aligned with and connected to at least one adjacent link with a slot formed between each pair of adjacent links, an orifice at the bottom of each link, and at least one slit in each link. The slit begins at the orifice and extends upward along at least a portion of the link. The coil sleeve is disposed in the control wire lumen around the control wire in a proximal region of the flexible tube. A portion of the control wire that extends from the second ring and to the first ring is not covered by the coil sleeve. Applying tension to the control wire causes the distal region of the flexible tube to bend.

In one example embodiment, a sheet is used to form a flexible catheter tube. The sheet has a plurality of spaced apart aligned cutouts each having a central portion between two end portions. A width of the central portion of each cutout is wider than the width of the two end portions of each cutout. The cutouts form a corresponding plurality of spaced apart aligned strips each having a central portion and two end portions. A width of the central portion of each strip is narrower than the width of the two end portions of each strip. The spaced apart aligned strips each have a second cutout along a first edge of the flat sheet. Each of the spaced apart aligned strips has at least one slit which begins at the second cutout and extends toward a center of the aligned strip. The sheet is configured to be rolled into a cylindrical shape (e.g., a substantially cylindrical shape) having a plurality of links with a slot formed between each pair of adjacent links, a bottom orifice for each link, and at least one slit extending upward from the bottom orifice. Top portions of the links correspond to the central portions of the strips. Bottom portions of the links correspond to the end portions of the strips. The bottom orifices correspond to the second cutouts. A side of the cylindrical shape (e.g., substantially cylindrical shape) corresponds to ends of the slits.

In one example embodiment, a delivery catheter includes a flexible tube, a plurality of links, a coiled tube, and a control wire. The flexible tube has a main lumen and a control wire lumen. Each of the links have a slit along a bottom region of the flexible tube. In a first configuration, the distal region of the flexible tube is straight, a top of each link is spaced apart from an adjacent link by a distance. In a second configuration, the distal region of the flexible tube is curved, the slits of each link are opened, and the distance between the top of each link has decreased such that the top of the distal region of the flexible tube defines a curve.

In one example embodiment, a delivery catheter has a first flexible portion, a second flexible portion, and a control wire. The first flexible portion has a first stiffness. The second flexible portion has a second stiffness that is different from the first stiffness. The control wire extends along the first flexible portion and the second flexible portion to a distal end of the second flexible portion. Applying tension to the control wire causes the first and second flexible portions of the flexible tube to bend to different radii.

In one example embodiment, a delivery catheter includes a first flexible portion, a second flexible portion, and a control wire. The first flexible portion has a first flexible frame with a first stiffness. The second flexible portion has a second flexible frame with a second stiffness that is different from the first stiffness. Applying tension to the control wire causes the first and second flexible portions of the flexible tube to bend to different radii.

In one embodiment, a delivery catheter usable for delivering a device to a native valve of a patient's heart comprises a flexible tube having a main lumen and a control wire lumen, and a plurality of links disposed in a distal region of the flexible tube. In some embodiments, each link is aligned with and connected to at least one adjacent link with a slot formed between each pair of adjacent links, wherein a top portion of each link is narrower than a bottom portion of each link when the links are viewed from a side, and wherein each link includes an orifice at the bottom of the link. In some embodiments, each link includes at least one slit, wherein the slit begins at the orifice and extends upward along at least a portion of the link. The delivery catheter includes a control wire in the control wire lumen that is connected to the plurality of links, such that applying tension to the control wire causes the distal region of the flexible tube to bend.

In one embodiments, a delivery catheter usable for delivering a device to a native valve of a patient's heart comprises a flexible tube having a main lumen and a control wire lumen. The delivery catheter can also include a first ring in a distal region of the flexible tube and a second ring in the distal region of the flexible tube that is spaced apart from the first ring. In one embodiment, the delivery catheter includes a single control wire in a control wire lumen that is connected to the first ring. A plurality of links can be disposed in the distal region of the flexible tube between the first ring and the second ring. In some embodiments, a coil sleeve is at least partially disposed in the control wire lumen around the control wire. The coil sleeve can be configured to extend proximally from the distal region of the flexible tube such that a portion of the single control wire that extends from the second ring and to the first ring is not covered by the coil sleeve. The delivery catheter can be configured such that applying tension to the single control wire causes the distal region of the flexible tube to bend.

In one embodiment, a delivery catheter for delivering a device to a native valve of a patient's heart comprises a flexible tube having a centered main lumen and a control wire lumen and a first ring in a distal region of the flexible tube. In some embodiments, a second ring is in the distal region of the flexible tube spaced apart from the first ring. The delivery catheter includes a single control wire in the control wire lumen that is connected to the first ring. In some embodiments, the delivery catheter further includes a plurality of cylindrically shaped links disposed in the distal region of the flexible tube between the first ring and the second ring. The plurality of cylindrically shaped links can be cut from a single piece of material, such that each link is aligned with and connected to at least one adjacent link with a slot formed between each pair of adjacent links. An orifice can be at the bottom of each link, and at least one slit can be in each link. The slit can be configured to begin at the orifice and extend upward along at least a portion of the link. The delivery catheter is configured such that applying tension to the control wire causes the distal region of the flexible tube to bend.

In some embodiments, the delivery catheter also includes a coil sleeve disposed in the control wire lumen around the control wire in a proximal region of the flexible tube. The coil sleeve can be configured to extend proximally from the distal region of the flexible tube such that a portion of the control wire that extends from the second ring and to the first ring is not covered by the coil sleeve.

In one embodiment, a sheet (e.g., a flat sheet) formable into a flexible catheter tube comprises a plurality of spaced apart aligned cutouts each having a central portion between two end portions, wherein a width of the central portion of each cutout is wider than the width of the two end portions of each cutout. The cutouts can be configured to form a corresponding plurality of spaced apart aligned strips each having a central portion and two end portions. A width of the central portion of each strip can be narrower than the width of the two end portions of each strip. In some embodiments, the spaced apart aligned strips each have a second cutout along a first edge of the flat sheet. Each of the spaced apart aligned strips can comprise at least one slit which begins at the second cutout and extends toward a center of the aligned strip. The sheet is configured to be rolled into a cylindrical shape (e.g., a substantially cylindrical shape) having a plurality of links with a slot formed between each pair of adjacent links. The cylindrical shape (e.g., substantially cylindrical shape) can also include a bottom orifice for each link, and at least one slit extending upward from the bottom orifice, wherein top portions of the links correspond to the central portions of the strips, bottom portions of the links correspond to the end portions of the strips, the bottom orifices correspond to the second cutouts, and a side of the cylindrical shape corresponds to ends of the slits.

In some embodiments, each of the spaced apart aligned strips comprises a third cutout along a second edge of the flat sheet, and each of the spaced apart flat strips comprises another slit that begins at the third cutout. The bottom orifices can further correspond to the third cutouts aligning with the second cutouts.

In one embodiment, a method of making a flexible catheter tube comprises providing a flat sheet and/or a hypotube and cutting a plurality of spaced apart aligned cutouts in to the sheet and/or hypotube. In some embodiments, each cutout has a central portion between two end portions, wherein a width of the central portion of each cutout is wider than the width of the two end portions of each cutout and wherein the cutouts form a corresponding plurality of spaced apart aligned strips each having a central portion and two end portions. A width of the central portion of each strip can be configured to be narrower than the width of the two end portions of each strip. With a flat sheet, the method can further include cutting a plurality of cutouts along a first edge of the flat sheet such that each edge of the aligned strips has a corresponding cutout along a first edge of the sheet. The method can further include cutting a plurality of slits, wherein each slit begins at one of the cutouts along the first edge and extends toward a center of the aligned strip. The method can further include rolling the sheet into a cylindrical shape (e.g., a substantially cylindrical shape) having (and/or configuring the hypotube such that it includes) a plurality of links with a slot formed between each pair of adjacent links, a bottom orifice for each link, and at least one slit extending upward from the bottom orifice, wherein top portions of the links correspond to the central portions of the strips, bottom portions of the links correspond to the end portions of the strips, the bottom orifices correspond to the second cutouts. A side of the cylindrical shape (e.g., substantially cylindrical shape) can correspond to the ends of the slits.

In some embodiments, each of the spaced apart aligned strips comprises a third cutout along a second edge of the flat sheet, and each of the spaced apart flat strips comprises another slit that begins at the third cutout, and the bottom orifices further correspond to the third cutouts aligning with the second cutouts.

In one embodiments, a delivery catheter usable for delivering a device to a native valve of a patient's heart comprises a flexible tube having a main lumen and a control wire lumen, and a plurality of links disposed in a distal region of the flexible tube, each link having a slit along a bottom region of the flexible tube. The delivery catheter can also include a coiled tube having a coiled tube lumen. A control wire can be positioned/located in the control wire lumen, be fixedly connected to a distal end of the plurality of links and extend through the coiled tube lumen.

In some embodiments, in a first configuration: the distal region of the flexible tube is straight, a length of the control wire extends distal to the coiled tube, another length of the control wire extends proximal to the coiled tube, and a top of each link is spaced apart from an adjacent link by a distance.

In some embodiments, in a second configuration: the distal region of the flexible tube is curved, the slits of each link are opened, a shorter length of the control wire extends distal to the coiled tube than in the first configuration, a longer length of the control wire extends proximal to the coiled tube than in the first configuration, and the distance between the top of each link has decreased such that the top of the distal region of the flexible tube defines a curve.

In some embodiments, the delivery catheter is configured such that applying tension to the control wire causes the distal region of the flexible tube to bend from the first configuration to the second configuration. In some embodiments, the delivery catheter is configured such that releasing tension from the control wire causes the distal region of the flexible tube to return to the first configuration.

In some embodiments, a delivery catheter for delivering a device to a native valve of a patient's heart comprises a flexible tube having a main lumen and a control wire lumen and a first flexible portion in a distal region of the flexible tube comprising a first flexible frame, wherein the first flexible portion has a first stiffness. In some embodiments, the delivery catheter includes a second flexible portion in the distal region of the flexible tube comprising a second flexible frame, wherein the second flexible portion has a second stiffness that is different from the first stiffness. In some embodiments, the delivery catheter includes a control wire extending through the control wire lumen of the first flexible portion and the second flexible portion to a distal end of the second flexible portion, such that applying tension to the control wire causes the first and second flexible portions of the flexible tube to bend.

In some embodiments, the first and second flexible frames comprise a plurality of links, and each of the plurality of links is aligned with and connected to at least one adjacent link to form a slot between each pair of adjacent links.

In some embodiments, each of the plurality of links comprises a top portion and a bottom portion, wherein the top portion is narrower than the bottom portion. In some embodiments, each of the plurality of links includes an orifice at the bottom of the link. In some embodiments, each of the plurality of links includes at least one slit, wherein the slit begins at the orifice and extends upward along at least a portion of the link.

In some embodiments, the second stiffness is less than the first stiffness and the slots between the links of the first flexible portion are narrower than the slots between the links of the second flexible portion. In some embodiments, the second stiffness is less than the first stiffness and the links of the first flexible portion are wider than the links of the second flexible portion. In some embodiments, the second stiffness is less than the first stiffness and the links of the first flexible portion are wider than the links of the second flexible portion. In some embodiments, the first flexible portion and the second flexible portion can form an about 90-degree bend in a bent condition.

In some embodiments, the first flexible portion has a first length that is about equal to a second length of the second flexible portion. In some embodiments, the first flexible portion has a first length that is about half as long as a second length of the second flexible portion. In some embodiments, the first flexible portion has a first length that is about one-third as long as a second length of the second flexible portion. In some embodiments, the first flexible portion has a first length that is about twice as long as a second length of the second flexible portion. In some embodiments, the first flexible portion has a first length that is about three times as long as a second length of the second flexible portion.

In some embodiments the first flexible portion is formed from a first polymer material, and the second flexible portion is formed from a second polymer material. In some embodiments, the second polymer material has a second durometer that is less than a first durometer of the first polymer material.

In one embodiment, a delivery catheter comprises a flexible tube having a main lumen and a control wire lumen. A first flexible portion in a distal region of the flexible tube comprises a first flexible frame, wherein the first flexible portion has a first stiffness. In some embodiments, a second flexible portion in the distal region of the flexible tube comprises a second flexible frame, wherein the second flexible portion has a second stiffness that is different from the first stiffness. In some embodiments, a third flexible portion in the distal region of the flexible tube comprises a third flexible frame, wherein the third flexible portion has a second stiffness that is different from the second stiffness. In some embodiments, a control wire extends through the control wire lumen of the first flexible portion, the second flexible portion, and the third flexible portion to a distal end of the third flexible portion, such that applying tension to the control wire causes the first, second, and third flexible portions of the flexible tube to bend.

In some embodiments, the first, second, and third flexible frames comprise a plurality of links, and each of the plurality of links is aligned with and connected to at least one adjacent link to form a slot between each pair of adjacent links.

In some embodiments, each of the plurality of links comprises a top portion and a bottom portion, wherein the top portion is narrower than the bottom portion. In some embodiments, each of the plurality of links includes an orifice at the bottom of the link. In some embodiments, each of the plurality of links includes at least one slit, wherein the slit begins at the orifice and extends upward along at least a portion of the link.

In some embodiments, the first stiffness and the third stiffness are less than the second stiffness and the slots between the links of the second flexible portion are narrower than the slots between the links of the first and third flexible portions. In some embodiments, the first stiffness and the third stiffness are less than the second stiffness and the links of the second flexible portion are wider than the links of the first and third flexible portions. In some embodiments, the first stiffness and the third stiffness are less than the second stiffness, the links of the second flexible portion are wider than the links of the first and third flexible portions, and the slots between the links of the second flexible portion are narrower than the slots between the links of the first and third flexible portions. In some embodiments, the first flexible portion, the second flexible portion, and the third flexible portion can form an about 90-degree bend in a bent condition.

In some embodiments, the first flexible portion has a first length that is about equal to a second length of the second flexible portion and a third length of the third flexible portion. In some embodiments, the first flexible portion has a first length and the third flexible portion has a third length and the first and third lengths are about half as long as a second length of the second flexible portion. In some embodiments, the first flexible portion has a first length and the third flexible portion has a third length and the first and third lengths are about one-third as long as a second length of the second flexible portion. In some embodiments, the first flexible portion has a first length and the third flexible portion has a third length and the first and third lengths are about twice as long as a second length of the second flexible portion.

In some embodiments, the first flexible portion is formed from a first polymer material, the second flexible portion is formed from a second polymer material, and the third flexible portion is formed from a third polymer material.

A further understanding of the nature and advantages of the present invention are set forth in the following description and claims, particularly when considered in conjunction with the accompanying drawings in which like parts bear like reference numerals.

BRIEF DESCRIPTION OF THE DRAWINGS

To further clarify various aspects of embodiments of the present disclosure, a more particular description of the certain embodiments will be made by reference to various aspects of the appended drawings. It is appreciated that these drawings depict only typical embodiments of the present disclosure and are therefore not to be considered limiting of the scope of the disclosure. Moreover, while the figures can be drawn to scale for some embodiments, the figures are not necessarily drawn to scale for all embodiments. Embodiments and other features and advantages of the present disclosure will be described and explained with additional specificity and detail through the use of the accompanying drawings in which:

FIG. 19A shows a flat view of a laser cut sheet usable to make the distal section of FIG. 18A-D;

FIGS. 34-36 show schematic side views of example distal ends of a delivery catheter in bent configurations for comparison of the three shown embodiments;

FIG. 49 shows a top view of the distal section of FIG. 44 with a control wire running therethrough; and FIG. 50 shows a side view of the distal section with a control wire shown in FIG. 49.

DETAILED DESCRIPTION

Figure 1:
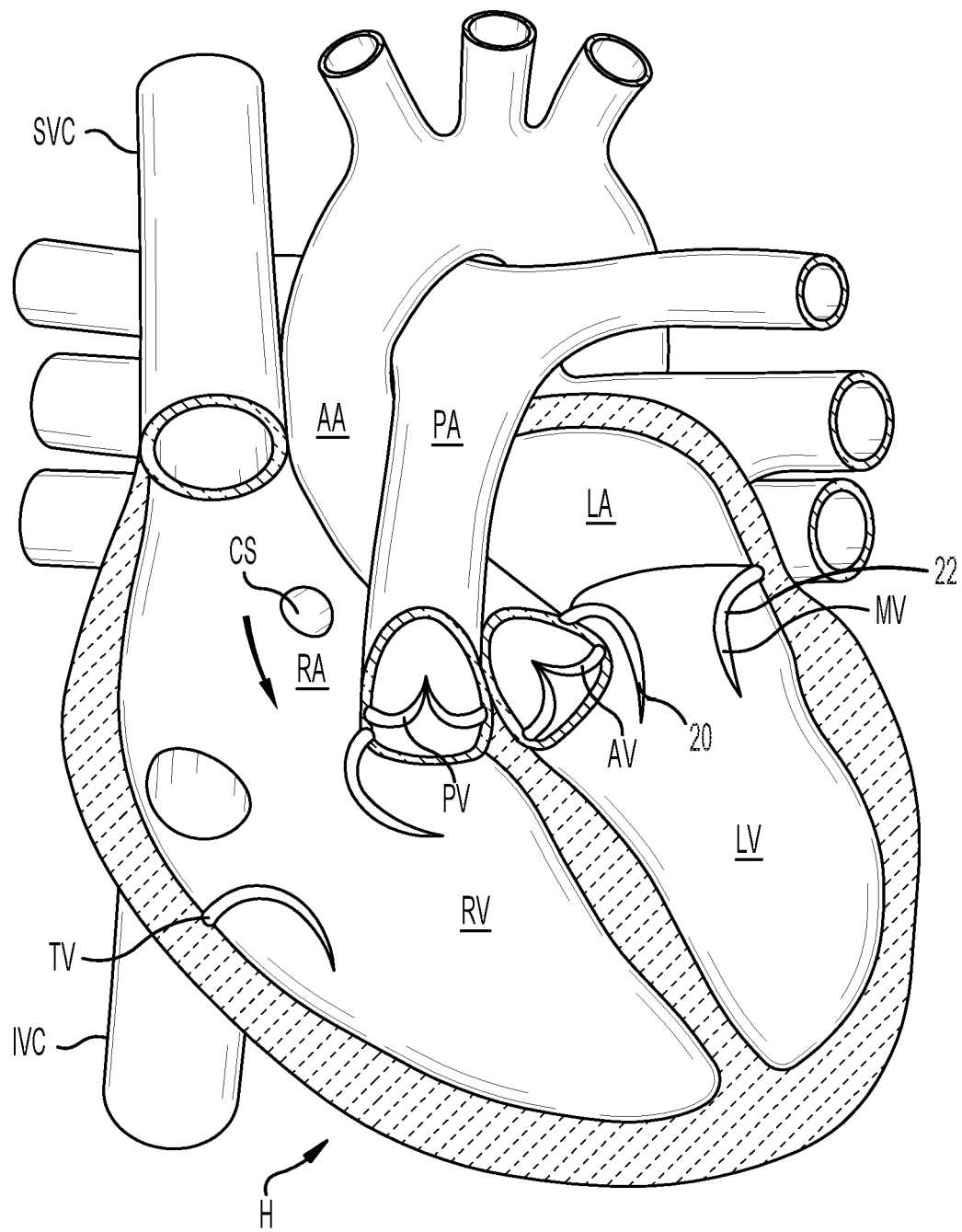
FIG. 1 illustrates a cutaway view of the human heart in a diastolic phase.

The following description refers to the accompanying drawings, which illustrate specific embodiments of the present disclosure. Other embodiments having different structures and operation do not depart from the scope of the present disclosure.

Example embodiments of the present disclosure are directed to devices and methods for repairing a defective heart valve. It should be noted that various embodiments of native valve reparation devices and systems for delivery are disclosed herein, and any combination of these options can be made unless specifically excluded. In other words, individual components of the disclosed devices and systems can be combined unless mutually exclusive or otherwise physically impossible. Further, the treatment methods and steps shown, discussed, and/or suggested herein can be performed on a living animal or on a simulation, such as on a cadaver, cadaver heart, simulator (e.g. with the body parts, heart, tissue, etc. being simulated), etc.

As described herein, when one or more components are described as being connected, joined, affixed, coupled, attached, or otherwise interconnected, such interconnection may be direct as between the components or may be indirect such as through the use of one or more intermediary components. Also as described herein, reference to a "member," "component," or "portion" shall not be limited to a single structural member, component, or element but can include an assembly of components, members, or elements. Also as described herein, the terms "substantially" and "about" are defined as at least close to (and includes) a given value or state (preferably within 10% of, more preferably within 1% of, and most preferably within 0.1% of).

The present disclosure generally concerns deployment tools for delivering valve repair and replacement devices and methods of using the same. More specifically, the disclosure relates to a flexible delivery catheter used to deploy valve repair and replacement devices at an implant site for the repair or replacement of heart valves that have malformations and/or dysfunctions, and methods of using the delivery catheter to implant such repair or replacement devices.

Described herein are embodiments of deployment tools that are intended to facilitate implantation of prosthetic devices at one of the native mitral, aortic, tricuspid, or pulmonary valve regions of a human heart, as well as methods for using the same. For example, the deployment tools can be used to deploy valve repair or replacement devices that serve as a docking site to position and secure a prosthetic heart valve at a native valve region. The details of the example embodiments of deployment tools described herein can be used to deploy a wide variety of valve repair and/or replacement devices.

The valve repair and/or replacement devices and methods involved can take a wide variety of forms, including but not limited to valves, docks, devices, systems, methods, etc. disclosed in U.S. patent application Ser. No. 15/912,971, filed on Mar. 6, 2018 and published as US 2018/0193139, those disclosed in U.S. patent application Ser. No. 15/902,956, filed on Feb. 22, 2019 and published as US 2018/0177594, and/or those disclosed in U.S. Patent Application Ser. No. 62/908,402, filed on Sep. 30, 2019, the disclosures of which are each herein incorporated by reference in their entirety. The valve repair or replacement device can be a transcatheter heart valve that is placed in a docking station. The valve repair or replacement device can also be a heart valve sealing device such as described in, and the systems and methods used can be the same as or similar to those described in, PCT Patent Application No. PCT/US2019/055320, filed on Oct. 9, 2019, and U.S. Patent Application Ser. No. 62/744,031, filed on Oct. 10, 2018, the disclosures of which are each herein incorporated by reference in their entirety. The deployment tools herein can be used to more accurately place such valve repair or replacement devices, so that the valve repair or replacement devices and prosthetic heart valves anchored thereto function properly after implantation. The methods and steps shown and/or discussed here and/or in the incorporated references can be performed on a living animal or on a simulation, such as on a cadaver, cadaver heart, simulator (e.g. with the body parts, heart, tissue, etc. being simulated), etc.

Figure 2:
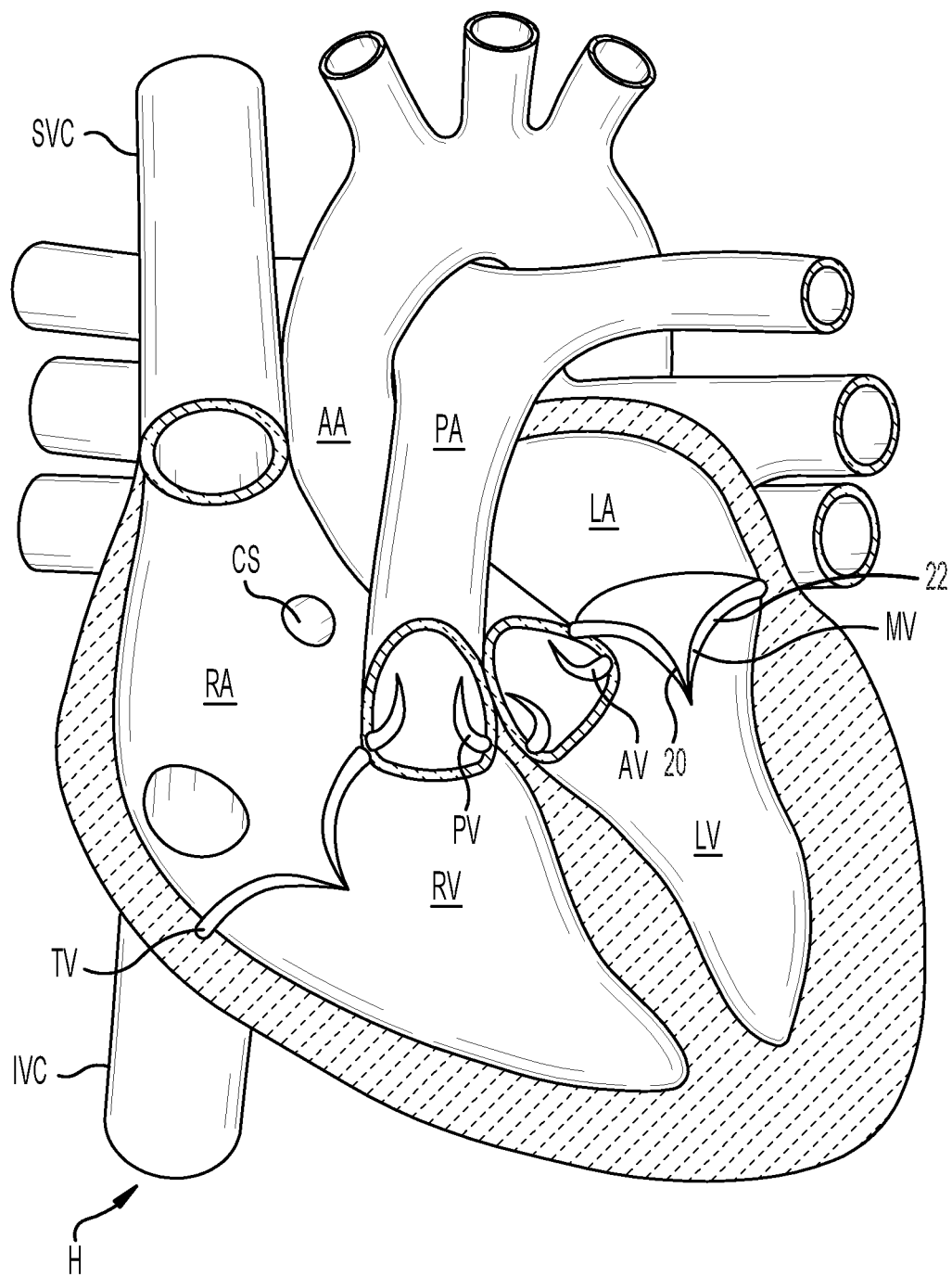
FIG. 2 illustrates a cutaway view of the human heart in a systolic phase.

FIGS. 1 and 2 are cutaway views of the human heart H in diastolic and systolic phases, respectively. The right ventricle RV and left ventricle LV are separated from the right atrium RA and left atrium LA, respectively, by the tricuspid valve TV and mitral valve MV; i.e., the atrioventricular valves. Additionally, the aortic valve AV separates the left ventricle LV from the ascending aorta AA, and the pulmonary valve PV separates the right ventricle from the pulmonary artery PA. Each of these valves has flexible leaflets (e.g., leaflets 20, 22 shown in FIGS. 4 and 5) extending inward across the respective orifices that come together or "coapt" in the flowstream to form the one-way, fluid-occluding surfaces. The native valve repair systems of the present application are described primarily with respect to the mitral valve MV. Therefore, anatomical structures of the left atrium LA and left ventricle LV will be explained in greater detail. It should be understood that the devices described herein may also be used in repairing other native valves, e.g., the devices can be used in repairing the tricuspid valve TV, the aortic valve AV, and the pulmonary valve PV.

The left atrium LA receives oxygenated blood from the lungs. During the diastolic phase, or diastole, seen in FIG. 1, the blood that was previously collected in the left atrium LA (during the systolic phase) moves through the mitral valve MV and into the left ventricle LV by expansion of the left ventricle LV. In the systolic phase, or systole, seen in FIG. 2, the left ventricle LV contracts to force the blood through the aortic valve AV and ascending aorta AA into the body. During systole, the leaflets of the mitral valve MV close to prevent the blood from regurgitating from the left ventricle LV and back into the left atrium LA, and blood is collected in the left atrium from the pulmonary vein. In one example embodiment, the devices described by the present application are used to repair the function of a defective mitral valve MV. That is, the devices are configured to help close the leaflets of the mitral valve to prevent blood from regurgitating from the left ventricle LV and back into the left atrium LA.

Figure 3:
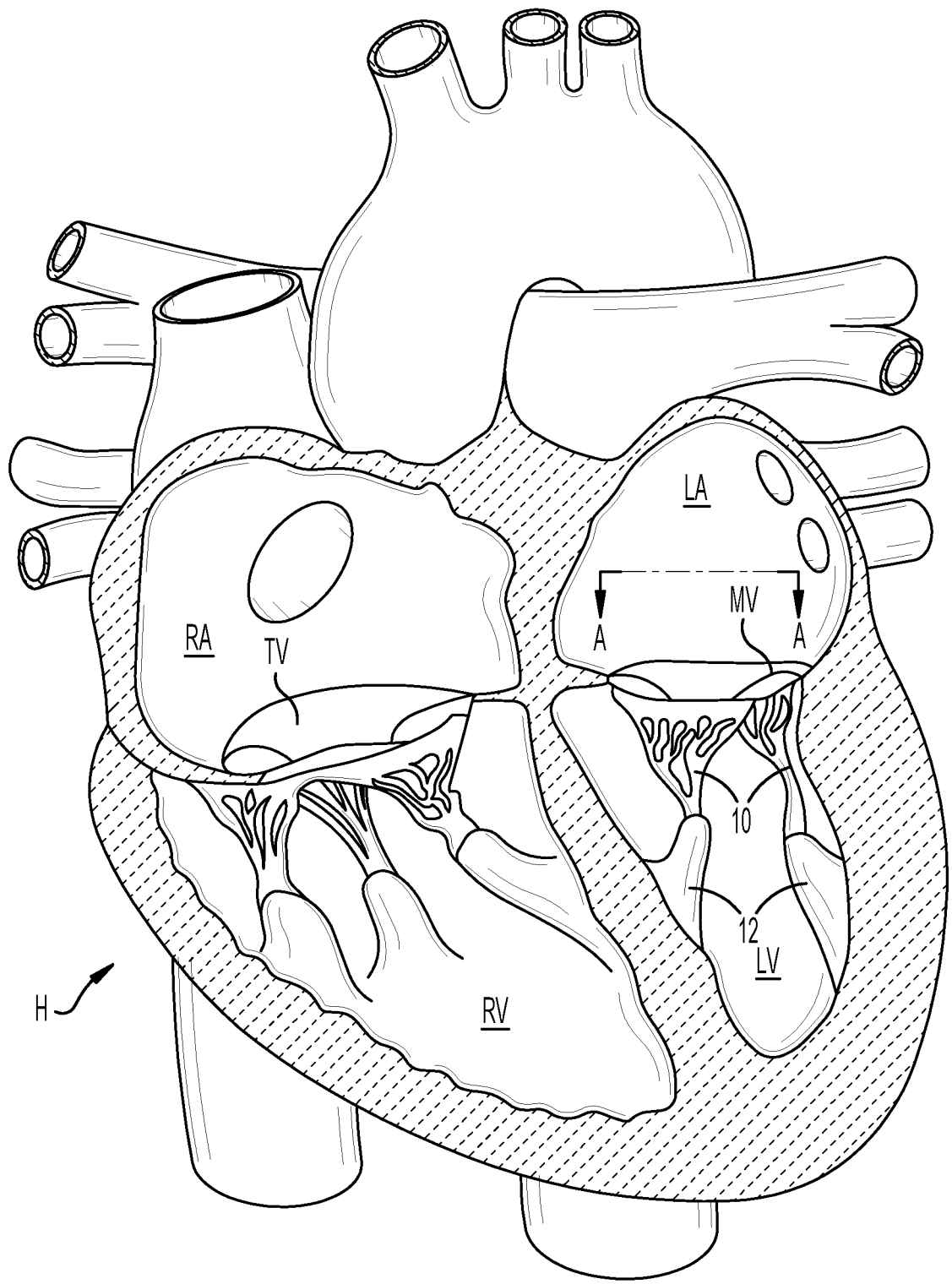
FIG. 3 illustrates a cutaway view of the human heart in a diastolic phase, in which the chordae tendineae are shown attaching the leaflets of the mitral and tricuspid valves to ventricle walls.

Referring now to FIGS. 1-7, the mitral valve MV includes two leaflets, the anterior leaflet 20 and the posterior leaflet 22. The mitral valve MV also includes an annulus 24, which is a variably dense fibrous ring of tissues that encircles the leaflets 20, 22. Referring to FIG. 3, the mitral valve MV is anchored to the wall of the left ventricle LV by chordae tendineae 10. The chordae tendineae 10 are cord-like tendons that connect the papillary muscles 12 (i.e., the muscles located at the base of the chordae tendineae and within the walls of the left ventricle) to the leaflets 20, 22 of the mitral valve MV. The papillary muscles 12 serve to limit the movements of the mitral valve MV and prevent the mitral valve from being reverted. The mitral valve MV opens and closes in response to pressure changes in the left atrium LA and the left ventricle LV. The papillary muscles do not open or close the mitral valve MV. Rather, the papillary muscles brace the mitral valve MV against the high pressure needed to circulate blood throughout the body. Together the papillary muscles and the chordae tendineae are known as the subvalvular apparatus, which functions to keep the mitral valve MV from prolapsing into the left atrium LA when the mitral valve closes.

Various disease processes can impair proper function of one or more of the native valves of the heart H. These disease processes include degenerative processes (e.g., Barlow's Disease, fibroelastic deficiency), inflammatory processes (e.g., Rheumatic Heart Disease), and infectious processes (e.g., endocarditis). In addition, damage to the left ventricle LV or the right ventricle RV from prior heart attacks (i.e., myocardial infarction secondary to coronary artery disease) or other heart diseases (e.g., cardiomyopathy) can distort a native valve's geometry, which can cause the native valve to dysfunction. However, the vast majority of patients undergoing valve surgery, such as surgery to the mitral valve MV, suffer from a degenerative disease that causes a malfunction in a leaflet (e.g., leaflets 20, 22) of a native valve (e.g., the mitral valve MV), which results in prolapse and regurgitation.

Generally, a native valve may malfunction in two different ways: (1) valve stenosis; and (2) valve regurgitation. Valve stenosis occurs when a native valve does not open completely and thereby causes an obstruction of blood flow. Typically, valve stenosis results from buildup of calcified material on the leaflets of a valve, which causes the leaflets to thicken and impairs the ability of the valve to fully open to permit forward blood flow.

The second type of valve malfunction, valve regurgitation, occurs when the leaflets of the valve do not close completely thereby causing blood to leak back into the prior chamber (e.g., causing blood to leak from the left ventricle to the left atrium). There are three main mechanisms by which a native valve becomes regurgitant—or incompetent—which include Carpentier's type I, type II, and type III malfunctions. A Carpentier type I malfunction involves the dilation of the annulus such that normally functioning leaflets are distracted from each other and fail to form a tight seal (e.g., the leaflets do not coapt properly). Included in a type I mechanism malfunction are perforations of the leaflets, as are present in endocarditis. A Carpentier's type II malfunction involves prolapse of one or more leaflets of a native valve above a plane of coaptation. A Carpentier's type III malfunction involves restriction of the motion of one or more leaflets of a native valve such that the leaflets are abnormally constrained below the plane of the annulus. Leaflet restriction can be caused by rheumatic disease (IIIa) or dilation of a ventricle (IIIb).

Figure 4:
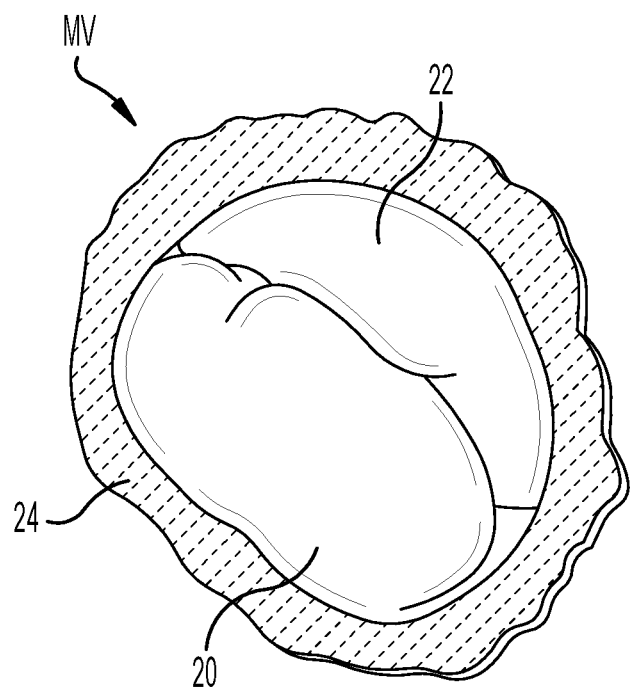
FIG. 4 illustrates a healthy mitral valve with the leaflets closed as viewed from an atrial side of the mitral valve.
Figure 5:
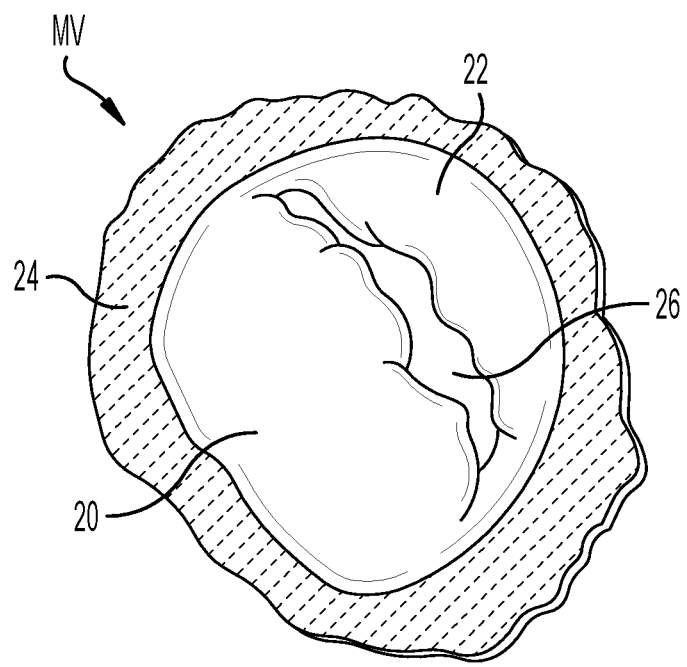
FIG. 5 illustrates a dysfunctional mitral valve with a visible gap between the leaflets as viewed from an atrial side of the mitral valve.

Referring to FIG. 4, when a healthy mitral valve MV is in a closed position, the anterior leaflet 20 and the posterior leaflet 22 coapt, which prevents blood from leaking from the left ventricle LV to the left atrium LA. Referring to FIG. 5, regurgitation occurs when the anterior leaflet 20 and/or the posterior leaflet 22 of the mitral valve MV is displaced into the left atrium LA during systole. This failure to coapt causes a gap 26 between the anterior leaflet 20 and the posterior leaflet 22, which allows blood to flow back into the left atrium LA from the left ventricle LV during systole. As set forth above, there are several different ways that a leaflet (e.g. leaflets 20, 22 of mitral valve MV) may malfunction, which can thereby lead to regurgitation.

Figure 6:
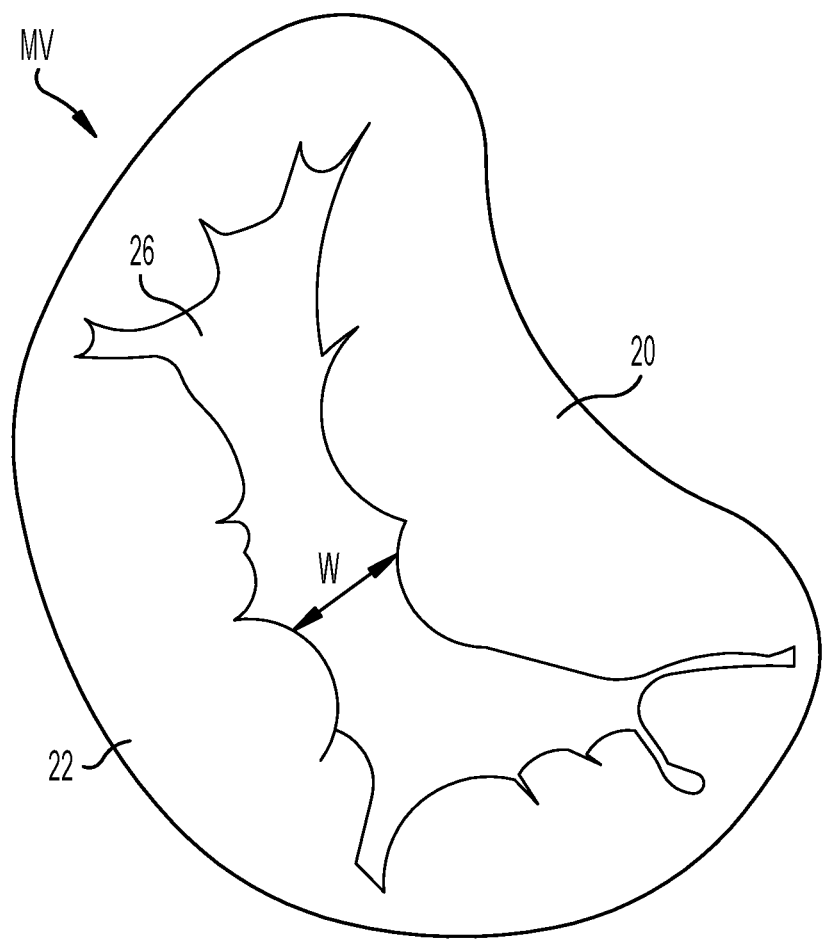
FIG. 6 illustrates a mitral valve having a wide gap between the posterior leaflet and the anterior leaflet.
Figure 7:
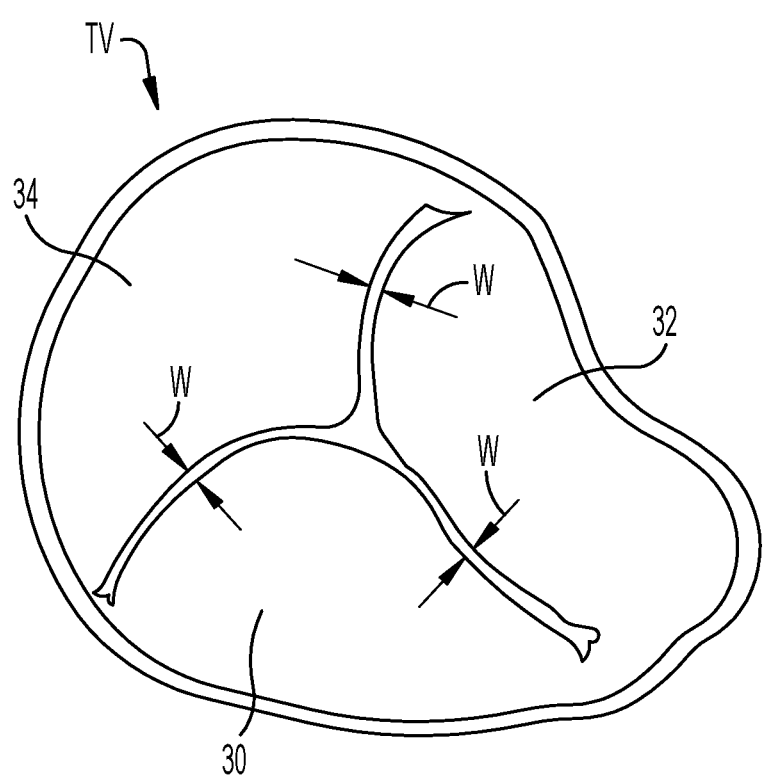
FIG. 7 illustrates a tricuspid valve viewed from an atrial side of the tricuspid valve.

Referring to FIG. 6, in certain situations, the mitral valve MV of a patient can have a wide gap 26 between the anterior leaflet 20 and the posterior leaflet 22 when the mitral valve is in a closed position (i.e., during the systolic phase). For example, the gap 26 can have a width W between about 2.5 mm and about 17.5 mm, such as between about 5 mm and about 15 mm, such as between about 7.5 mm and about 12.5 mm, such as about 10 mm. In some situations, the gap 26 can have a width W greater than 15 mm. In any of the above-mentioned situations, a valve repair device is desired that is capable of engaging the anterior leaflet 20 and the posterior leaflet 22 to close the gap 26 and prevent regurgitation of blood through the mitral valve MV.

When mitral valve regurgitation occurs, blood enters the left atrium from the left ventricle during systole. In a healthy heart, blood should only enter the left atrium from the pulmonary veins, not the left ventricle. But when mitral valve regurgitation occurs the left atrial pressure then increases above the pressure it should be, throughout the cardiac cycle, and is most noticeable at the end of systole.

Although stenosis or regurgitation can affect any valve, stenosis is predominantly found to affect either the aortic valve AV or the pulmonary valve PV, and regurgitation is predominantly found to affect either the mitral valve MV or the tricuspid valve TV. Both valve stenosis and valve regurgitation increase the workload of the heart H and may lead to very serious conditions if left un-treated; such as endocarditis, congestive heart failure, permanent heart damage, cardiac arrest, and ultimately death. Because the left side of the heart (i.e., the left atrium LA, the left ventricle LV, the mitral valve MV, and the aortic valve AV) is primarily responsible for circulating the flow of blood throughout the body, malfunction of the mitral valve MV or the aortic valve AV is particularly problematic and often life threatening. Accordingly, because of the substantially higher pressures on the left side of the heart, dysfunction of the mitral valve MV or the aortic valve AV is much more problematic.

Malfunctioning native heart valves may either be repaired or replaced. Repair typically involves the preservation and correction of the patient's native valve. Replacement typically involves replacing the patient's native valve with a biological or mechanical substitute. Typically, the aortic valve AV and pulmonary valve PV are more prone to stenosis. Because stenotic damage sustained by the leaflets is irreversible, the most conventional treatments for a stenotic aortic valve or stenotic pulmonary valve are removal and replacement of the valve with a surgically implanted heart valve, or displacement of the valve with a transcatheter heart valve. As noted above, the various valves of the heart can be repaired using transvascular techniques wherein a delivery catheter enters the heart through, for example, the inferior vena cava IVC and is then directed toward the valve needing repair. Different paths through the heart are required to reach different valves. As an example, reaching the tricuspid valve TV from the inferior vena cava IVC requires tight turns or bends to be made in the catheter almost immediately after entry into the right atrium RA from the inferior vena cava IVC (see FIGS. 2 and 3). In contrast, reaching the mitral valve MV from the inferior vena cava IVC requires that the septum be punctured so that the catheter can pass from the right atrium RA to the left atrium LA before bending toward the mitral valve MV.

Referring now to FIGS. 8A-31C, example embodiments of delivery catheters having a steerable distal end and components thereof (e.g., flexible tube frames and one or more control wires (e.g., pull wires, etc.) to control the curvature of the distal region of the delivery catheter, etc.) are illustrated and described in detail.

Figure 8A:
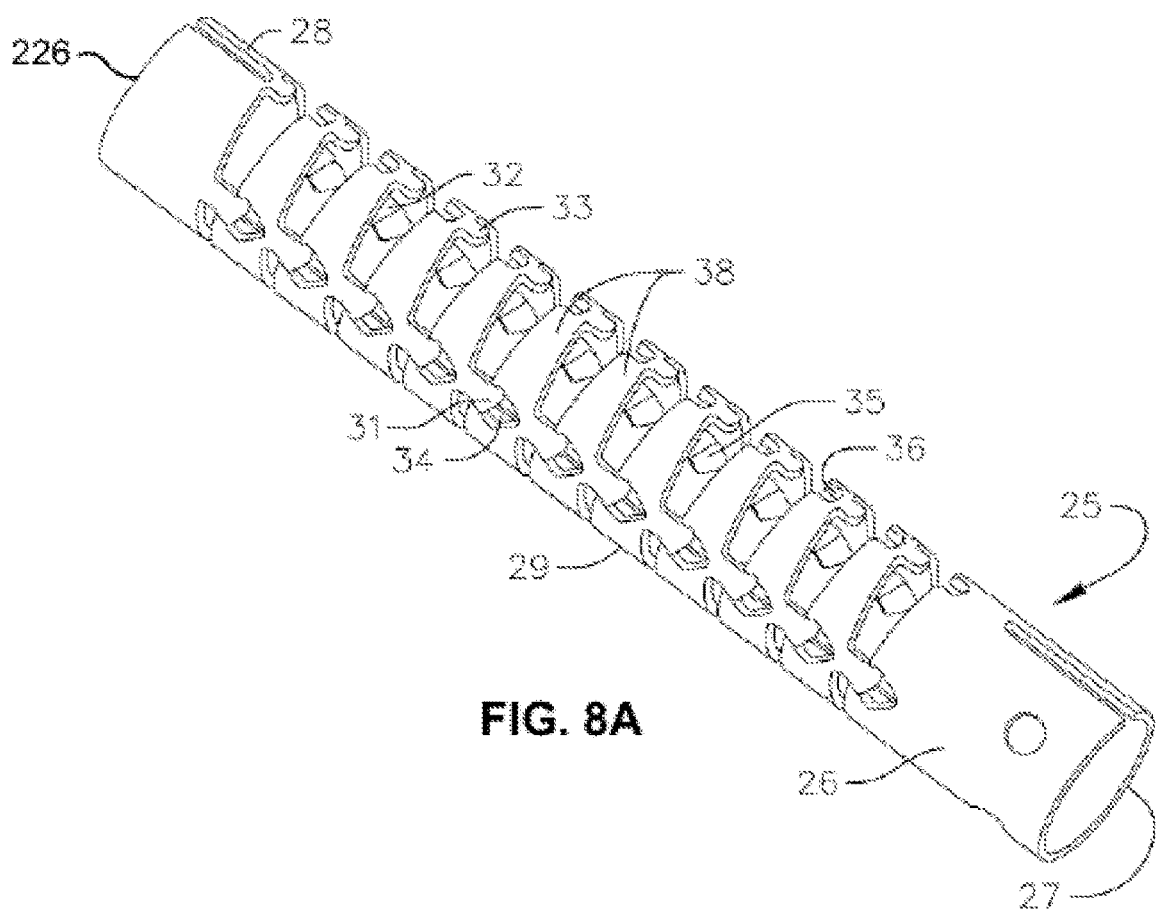
FIG. 8A shows a perspective view of an example distal section of (or usable in) a delivery catheter as part of a delivery device or system for implanting a valve repair or replacement device.
Figure 8B:
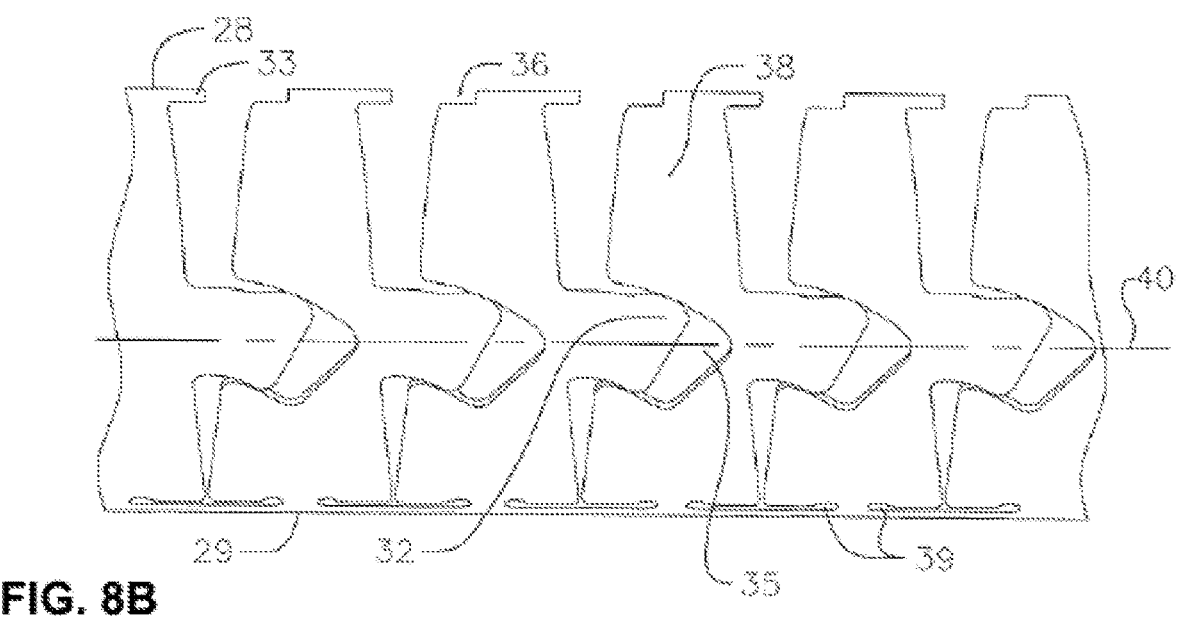
FIG. 8B is a cross-sectional view of several links of the distal section of FIG. 8A.

FIG. 8A shows a perspective view of a component of a distal section 25 of a delivery catheter 224 (See FIG. 9), according to an example embodiment. The delivery device can have features such as those described in U.S. patent application Ser. No. 15/984,661, filed on May 21, 2018 and published as US 2018/0318079, the disclosure of which is herein incorporated by reference in its entirety. The distal section includes two opposite ends and sides 226, 27, a top 28, and a bottom 29 extending between the two ends. These have been labelled for case of understanding and are not intended to limit the orientation of the distal section 25. The flexible tube frame in the distal section 25 of the delivery catheter forms a generally cylindrical hollow tube including a plurality of links 38. The distal section and/or flexible tube can be covered, coated, and/or include additional elements in the final configuration of the delivery catheter. Each link 38 has the shape of a cylindrical segment and each link 38 is aligned with and connected to adjacent links 38 to form the cylindrical tube shape of the distal section 25. While the distal section 25 is cylindrical in this embodiment, other shapes, such as ovular distal sections, are also possible. Each link 38 of the distal section 25 has a greater width at the bottom 29 than at the top 28, giving the links 38 the general shape of an acute trapezoid when viewed from the side, as best seen in FIG. 8B. The bottom of each link 38 has slits 39 to allow for more flexing of the links 38 relative to one another.

Figure 9:
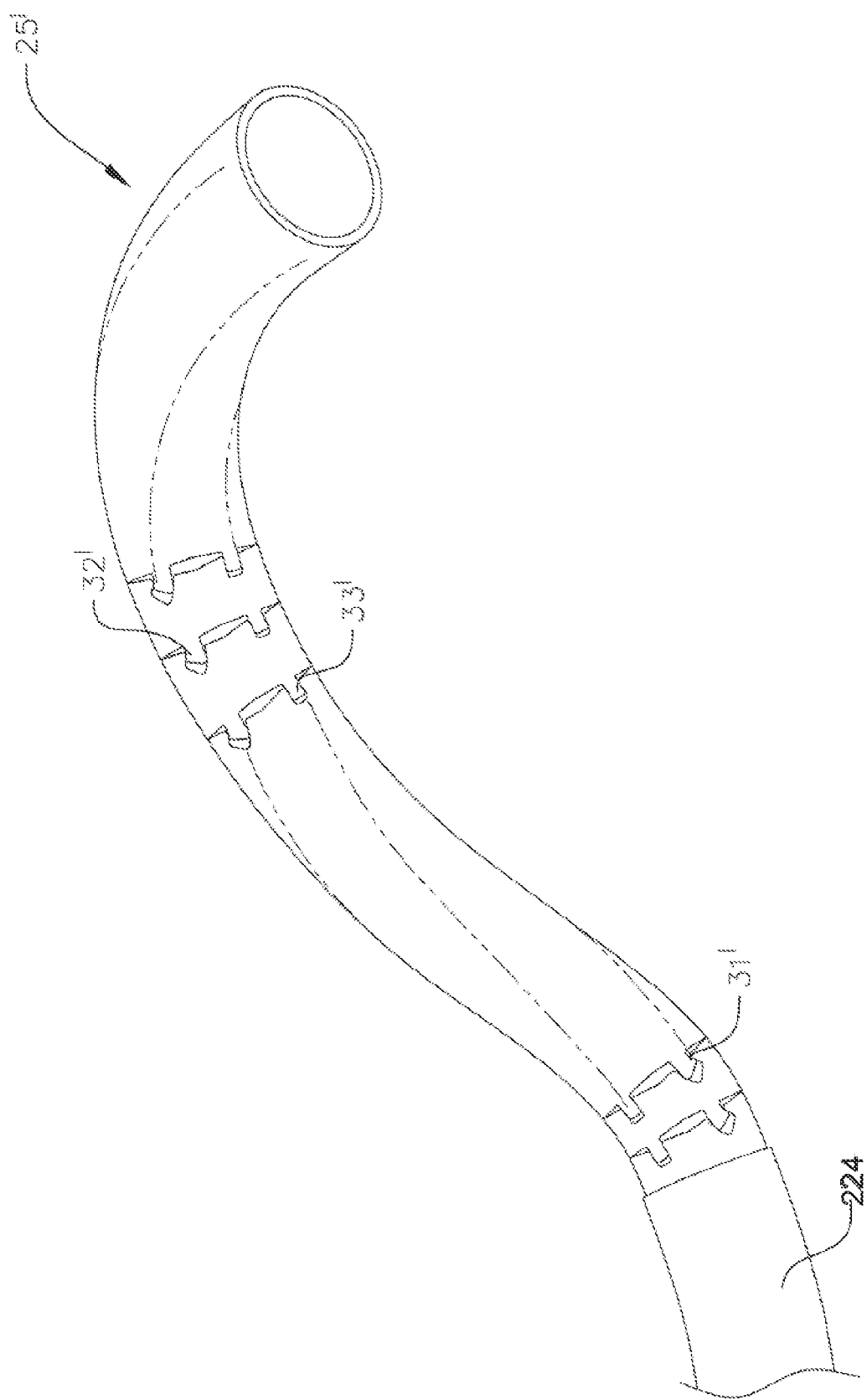
FIG. 9 is a perspective view of an example distal section of (or usable in) a delivery catheter, the distal section in a bent configuration.

The distal section 25 also includes an optional double guiding pattern forming a hybrid bending section that incorporates both side teeth 31, 32 and top teeth 33. To this effect, each link 38 includes two side teeth 31, 32 on opposite sides of the link 38 and a top tooth 33. With respect to the distal section 25, the two rows of side teeth 31, 32 of the links 38 run the length of the sides 226, 27 of the distal section 25, respectively, and the top teeth 33 run the length of the distal section 25 on the top 28, as best seen in FIG. 8A. While the rows of side teeth 31, 32 and top teeth 33 are shown to run straight along the length of the distal section 25 in this illustrated embodiment, other embodiments can have different configurations. For example, in some embodiments, the rows of side teeth 31, 32 and top teeth 33 can spiral around the tube of the distal section 25, for example, as shown in FIG. 9, to effect specific bending shapes of the distal section 25 when the distal section 25 is actuated. In some embodiments, the side teeth 31, 32 can be mirror images of each other to allow analogous bending on opposite sides 226, 27 of the distal section 25. In some embodiments, the side teeth 31, 32 can have different shapes and/or sizes in comparison to each other. The teeth 31, 32, 33 can take any other suitable shape and/or size that allows the distal section 25 to move to a flexed configuration while delivering a valve repair or replacement device. While the teeth 31, 32, 33 are all right-facing teeth in the illustrated embodiment (e.g., directed to the right in the view shown in FIG. 8B), in other embodiments, the teeth can be left-facing teeth (see, for example, FIG. 9) or the top and side teeth can face different directions, for example.

Adjacent to each side tooth 31, 32 and each top tooth 33 is a corresponding side slot or groove 34, 35 and top slot or groove 36, respectively, on an adjacent link 38. Each slot 34, 35, 36 can have a shape complementary to the side tooth 31, 32 or top tooth 33 to which it is adjacent. When the distal section 25 is in a straightened configuration, the side teeth 31, 32 are partially inserted into the side slots 34, 35 and the top teeth 33 are separated from their adjacent top slots 36 by a gap. Having the side teeth 31, 32 partially within the side slots 34, 35 in this straightened configuration provides additional torque resistance to the distal section 25 when the distal section 25 of the delivery catheter 224 is not fully flexed. However, in some embodiments, the side teeth 31, 32 may not be positioned partially within the side slots 34, 35 when the distal section 25 is in the straightened configuration.

When the distal section 25 is bent, each side tooth 31, 32 moves further into its corresponding side slot 34, 35 and each top tooth 33 moves closer to and then into its corresponding top slot 36. The addition of the top teeth 33 and top slots 36 provides enhanced torqueability and torque resistance to the distal section 25 when it is in the fully flexed configuration. Further, having both side teeth 31, 32 and top teeth 33 provides additional guiding control and structural support when adjusting the distal section 25 from its straightened to its flexed configuration.

FIG. 8B is a detailed cross-sectional view of several links 38 of the distal section 25 of FIG. 8A. While FIG. 8B is described with respect to the side teeth 32, this description equally applies to side teeth 31 on the opposite side of the distal section 25. Side teeth 32 are positioned along a tooth line 40 that is low relative to the top 28 of the distal section 25. This positioning causes the side teeth 32 to have a smaller displacement, i.e., the distance the side teeth 32 move into the adjacent slot 35 is much shorter or less than if the side teeth 32 were positioned closer to the top 28 of the distal section 25. For example, in the illustrated embodiment, the distance that the side teeth 31, 32 move during flexing is smaller compared to the distance that the top teeth 33 move. In other words, the top teeth 33 move a greater distance relative to adjacent links 38 when the distal section 25 is adjusted to a fully bent configuration, as compared to the side teeth 31, 32. This arrangement allows the use of shorter side teeth 31, 32 (e.g., to have side teeth with shorter longitudinal lengths), which can in turn be incorporated into shorter bending sections in the distal section 25.

Further, the low tooth line also provides more space for wider tooth slots 34, 35 to accommodate, for example, even larger side teeth since the tooth slots 34, 35 are located at the wider lower portions of the links 38. Having more space to house larger and/or more appropriate or robust tooth slots 34, 35 for the side teeth 31, 32 can enhance guiding of the teeth 31, 32 into the slots 34, 35, for example, during bending. The low tooth line also allows for the above discussed robust tooth design that can still provide structural support while bending the links away from each other, i.e., in the opposite direction of the bending configuration. Therefore, when bending the links away from each other, the side teeth can still maintain their interface with the adjacent side slots, and this maintained tooth-slot interface can provide for more structural support and torqueability.

FIG. 9 is a perspective view of a distal section 25' in a bent configuration according to a modification of the first embodiment. The distal section 25' in FIG. 9 is similar to the distal section 25 of FIG. 8A, except that in FIG. 9, the rows of top teeth 33' and the rows of side teeth 31', 32' are shifted laterally around the tube-shaped distal section 25' instead of continuing in a straight line down the length of the distal section. This positioning of the rows of teeth 31', 32', 33' along, for example, a spiral line allows the distal section 25' to bend in three dimensions, as opposed to a single plane as would occur in FIG. 8A. As seen in FIG. 9, the example distal section 25' has a three-dimensional curved shape. Various embodiments of distal sections can be laser cut so that the top and side teeth follow a pattern that will form a desired shape during bending. For example, patterns can be cut that create a distal section having a bent shape that, when used in surgery, allows the distal section to be positioned at the mitral or other valve, such that a valve repair or replacement device can be advanced from the distal section and accurately positioned at the valve.

Figure 10:
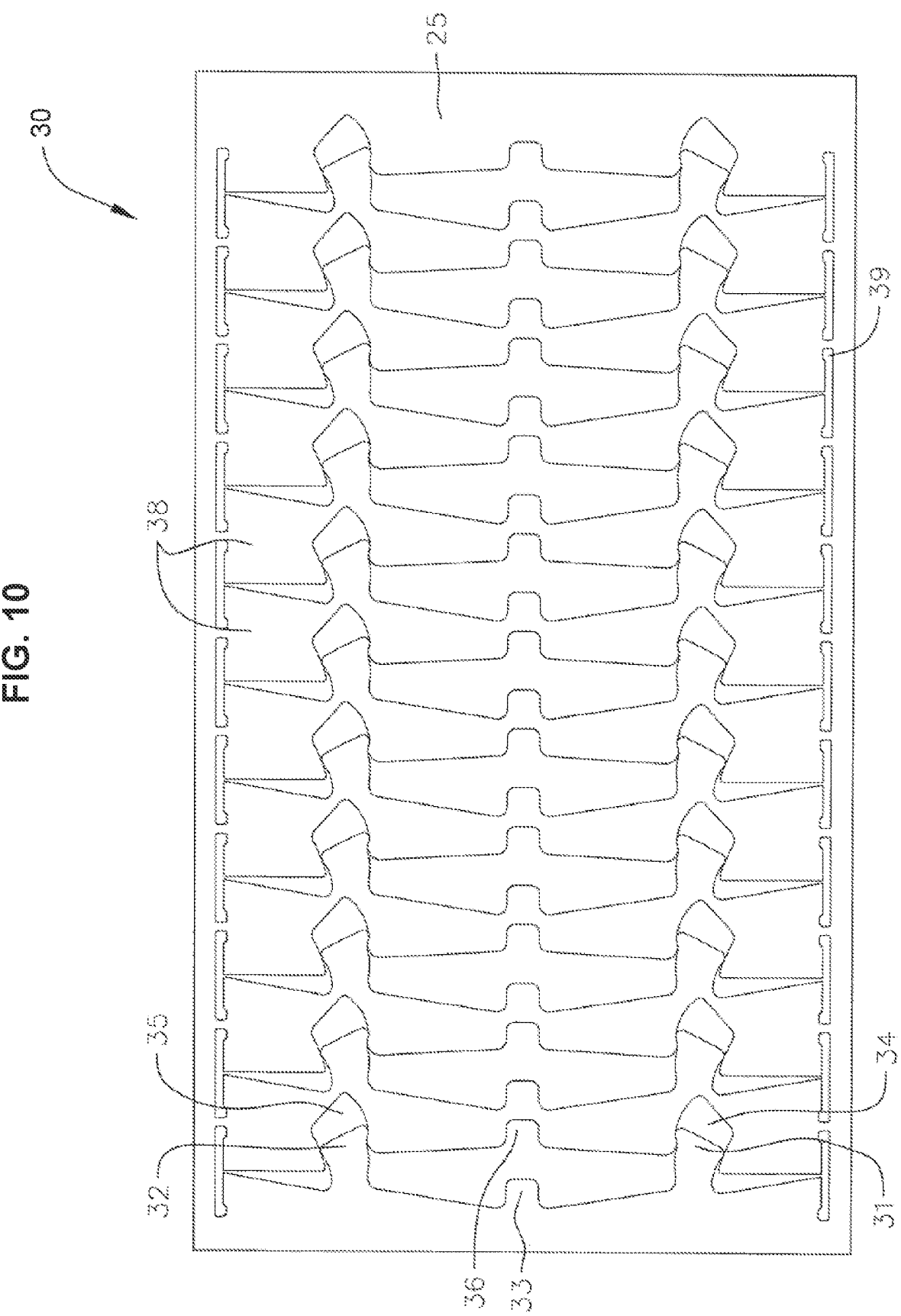
FIG. 10 is a flat view of an example laser cut sheet usable to make the distal section of FIGS. 8A-8B.
Figure 11:
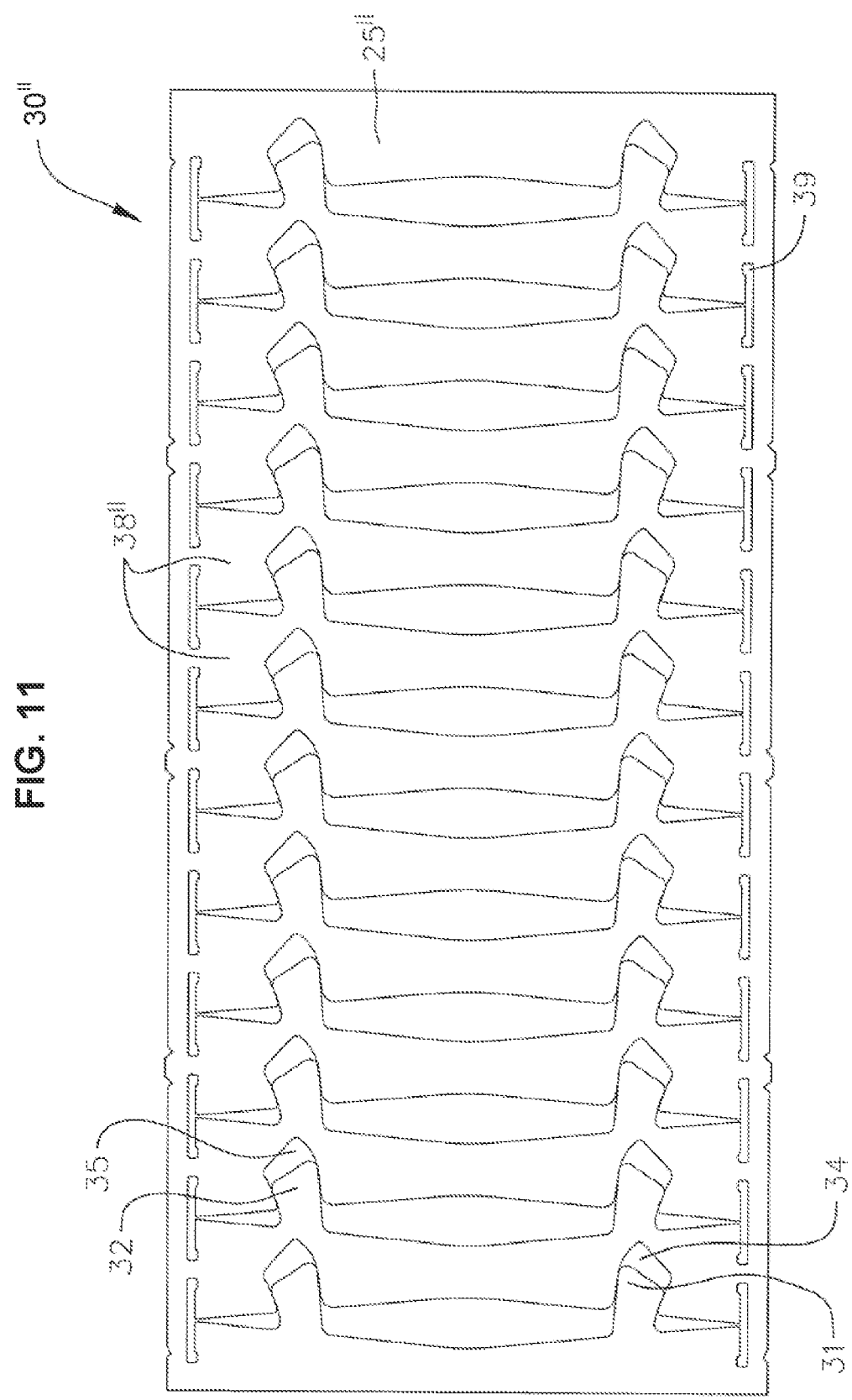
FIG. 11 is a flat view of an example laser cut sheet usable to make the distal section of FIG. 9.
Figure 12:
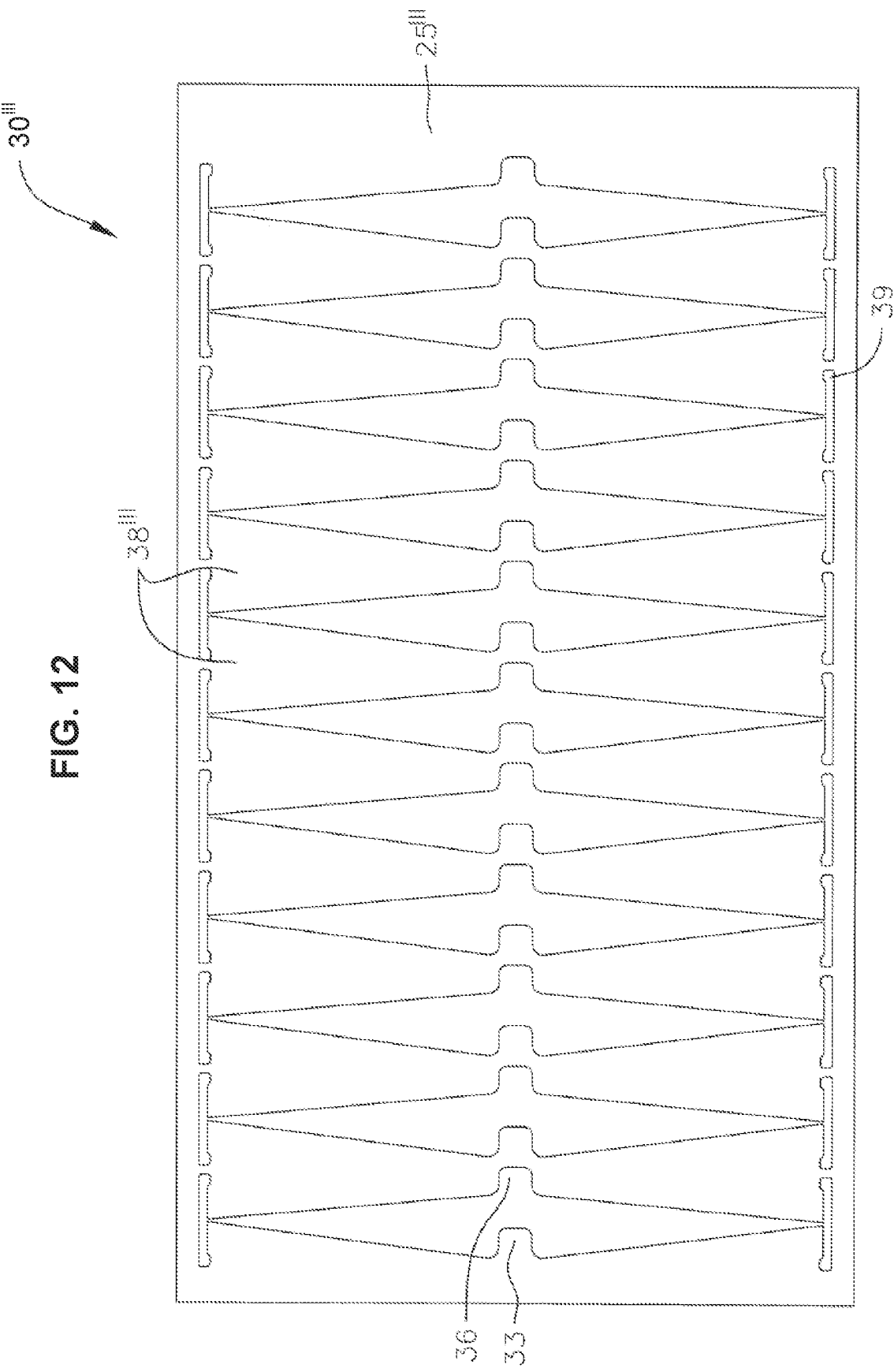
FIG. 12 is a flat view of an example laser cut sheet useable to make a distal section for a delivery catheter.

Distal sections 25, 25' can be manufactured by cutting, for example, by laser cutting a flat metal strip or sheet with the desired pattern and then rolling the patterned metal strip or sheet into a hypotube or by cutting a pre-formed hypotube. As one example, FIG. 10 is a flat view of a laser cut file or sheet 30 for the distal section 25 of FIG. 8A. This laser cut sheet 30 includes both the top teeth 33 and their associated slots 36 and the side teeth 31, 32 and their associated slots 34, 35 arranged in straight rows along the length of the distal section 25. However, as noted above, this laser cut sheet 30 can be modified to have the teeth 31, 32, 33 and their associated slots 34, 35, 36 arranged in other different paths or configurations, for example, in rows of spiral lines, in order to create a curved or spiral bent distal section 25' similar to the one shown in FIG. 9. In some embodiments, various patterns can be cut that provide distal sections that can bend in other shapes or configurations that help accurately navigate and deploy a valve repair or replacement device into position at the implant site during surgery. For example, FIGS. 11-12 and 18A-19B illustrate example embodiments of slots and/or grooves, slits, and cut-outs that help accurately navigate and deploy a mitral valve implant. The various patterns can be cut into sheets and formed into tubes or can be cut directly into a pre-formed tube, e.g., a hypotube.

Many types of sheets capable of being folded into tubing and/or many types of tubes can be used for making the cut distal sections. For example, Nitinol and stainless steel can be used, as well as various other suitable metals known in the art, as materials for the sheets and/or tubes.

While the above embodiments include both top and side teeth, such that each link 38 has three teeth total, other embodiments may only include one of either the top or side teeth, or no teeth at all.

Various sheath and catheter designs can be used to effectively deploy the valve repair or replacement device at the implant site. For example, for deployment at the mitral position, the delivery catheter can be shaped and/or positioned to point towards commissure A3P3 and/or to point downward into the center of the mitral valve, between the leaflets of the mitral valve. In still further embodiments, the catheter itself can also be positioned to pass through the mitral valve, below the mitral plane, and to extend into the left ventricle (e.g., through one of the commissures). The catheter can be positioned in any suitable manner that allows a valve repair or replacement device to be deployed at an implant site. In some embodiments, the catheter itself can have an atraumatic tip design, to provide atraumatic access to the implant site, for example, by reducing or eliminating any damage that could potentially be caused by the advancement and/or shape manipulation of the catheter while it is positioned at the implant site.

Figure 13:
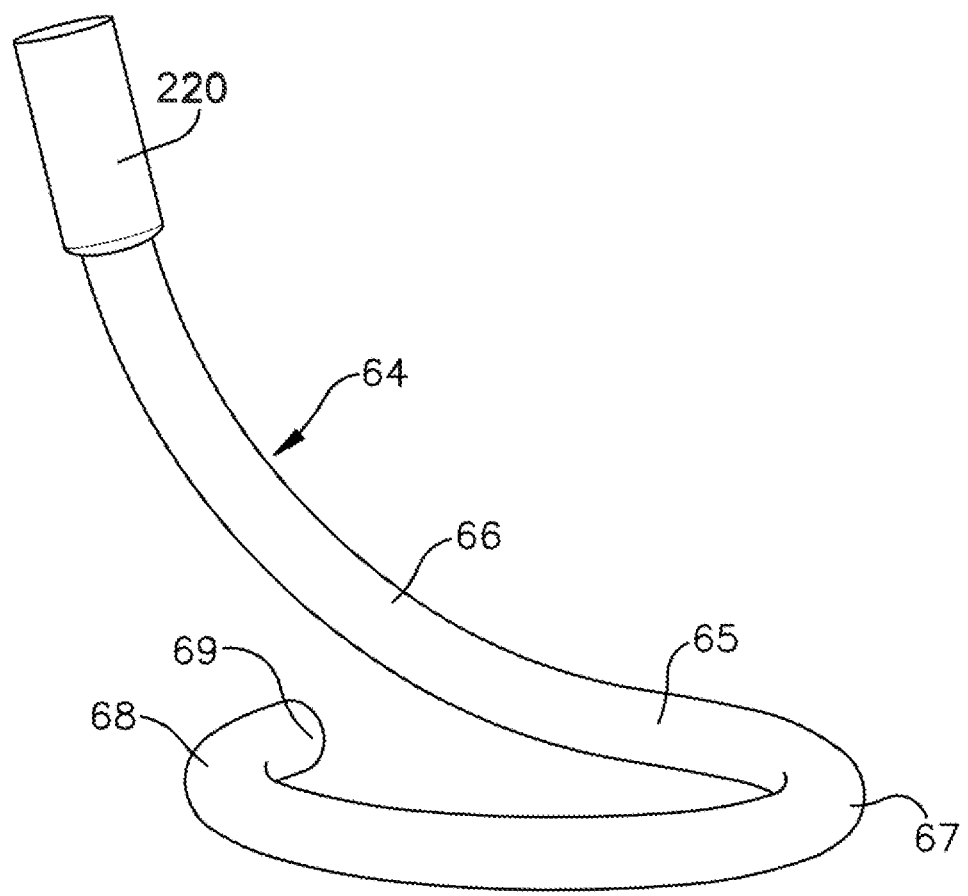
FIG. 13 shows a perspective view of a curved configuration of a distal section of (or usable in) a delivery catheter used for implanting a valve repair or replacement device at a native valve, which can be used in a trans-septal technique.

FIG. 13 shows a perspective view of a curved configuration, multiple-curve configuration, or a "hockey stick" configuration of a distal section 65 of a delivery catheter 64. This configuration can be used for implanting a valve repair or replacement device at a native mitral valve using, for example, a trans-septal technique. In the illustrated configuration, the distal end 65 of the delivery catheter 64 extending from a guide sheath 220 (e.g., a trans-septal sheath) has four main subsections: a shallow curved portion 66, a circular planar portion 67, a turn 68 and a flexible end portion 69. The shapes of these subsections allow the distal section 65 to navigate the delivery catheter 64 into position at a native valve, e.g., at a native mitral valve, and accurately deploy a valve repair or replacement device at the native valve. The distal section 65 can take any suitable form that allows the distal section to take the flexed configuration described above, such as, for example, any form described in the present application. While, in the illustrated embodiment, the distal section 65 of the delivery catheter 64 curves in a clockwise direction, in other embodiments, the distal section 65 can instead curve in an opposite, counter-clockwise direction. In embodiments where the delivery device is configured to deploy an implantable device in the tricuspid valve, as is described above, different bend profiles and radii can be selected to navigate the delivery catheter into position at the native tricuspid valve.

In some embodiments, the flexible tube frame can be a full laser cut hypotube (similar to the laser cut catheter described in FIGS. 9-12 above) where the cuts are arranged in a pattern such that, when bent, the distal section forms the spiral configuration. In some embodiments, the spiral configuration of the laser cut hypotube is allowed to be shape set to a spiral that stretches or extends from the FO to a position that is lower than the mitral plane. Respective gaps between the top teeth and their associated slots (e.g., where the slots are radially wider than the teeth to provide a space for the teeth to move radially when they are in their respective slots) allows the vertical stretching of the catheter to occur. The distal section can be shape set with this vertically stretched configuration. Then when the spiral is in the mitral anatomy, the distal tip of the catheter can be pulled up to position it along or just above the mitral plane, for example, by flexing or tensioning the flex wire in or otherwise attached to the distal section of the catheter as previously discussed. This feature allows the spiral to be adjusted to varying heights to accommodate different patient anatomies.

Figure 14:
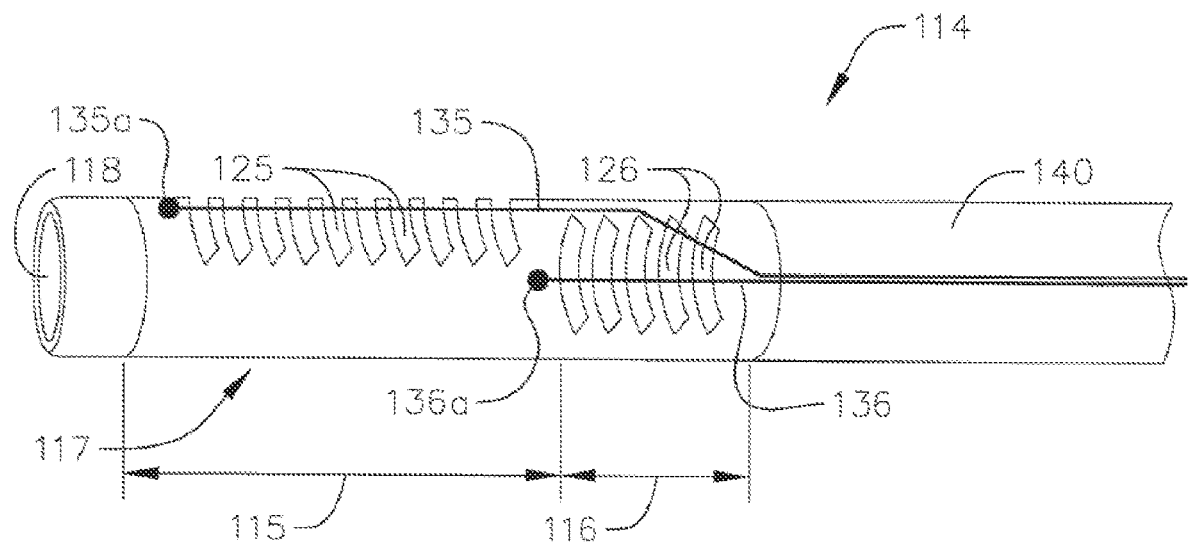
FIG. 14 shows a schematic side view of an example distal section of (or usable in) a delivery catheter with a two-control wire system, which can be used in the delivery catheter of FIG. 13.
Figure 15:
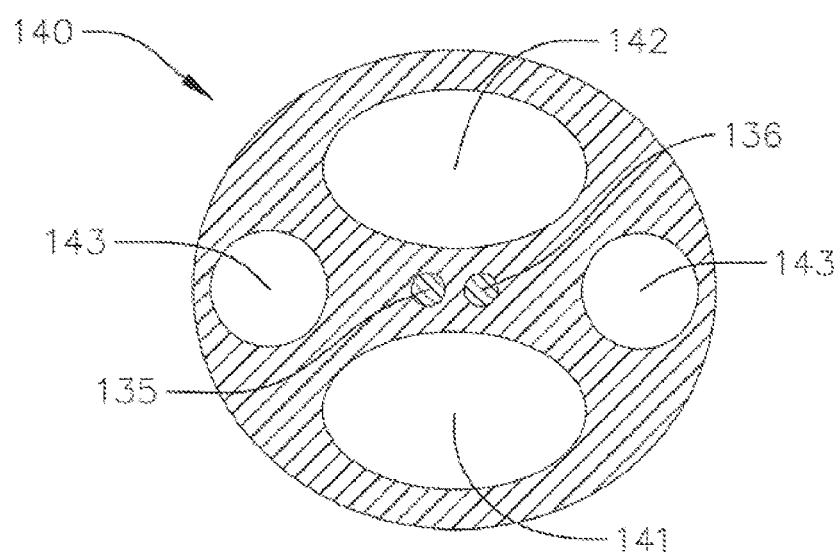
FIG. 15 shows a cross-sectional view of a multi-lumen extrusion portion of the delivery catheter of FIGS. 13 and 14, the cross-section taken in a plane perpendicular to a longitudinal axis of the delivery catheter.
Figure 16:
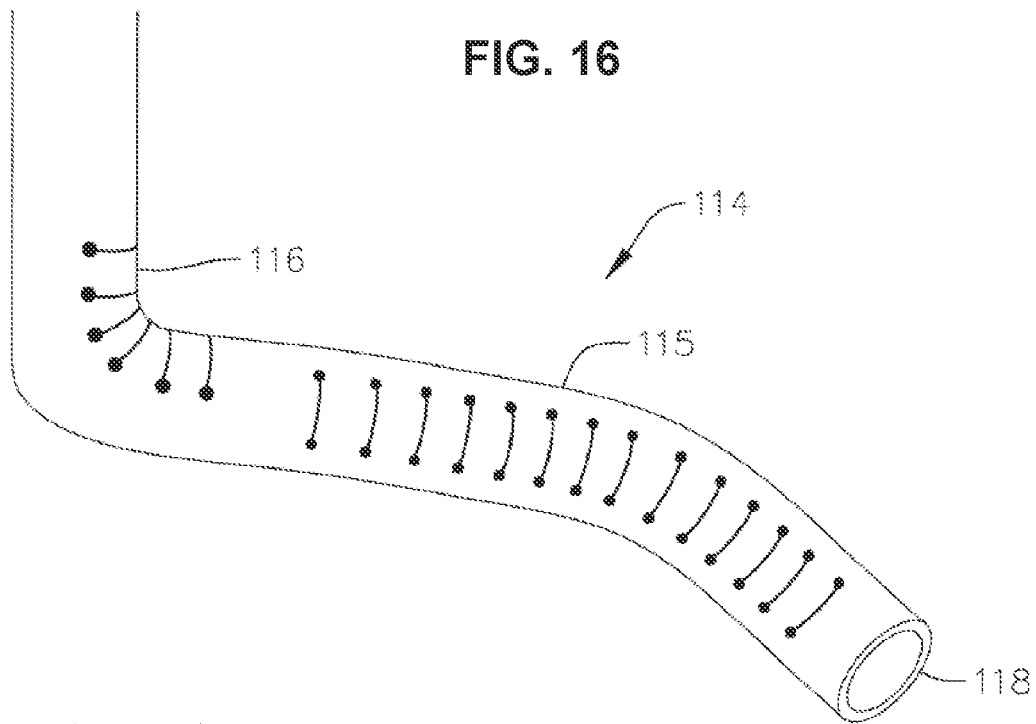
FIG. 16 shows a schematic perspective view of the delivery catheter of FIGS. 13-15 in a partially actuated state.
Figure 17:
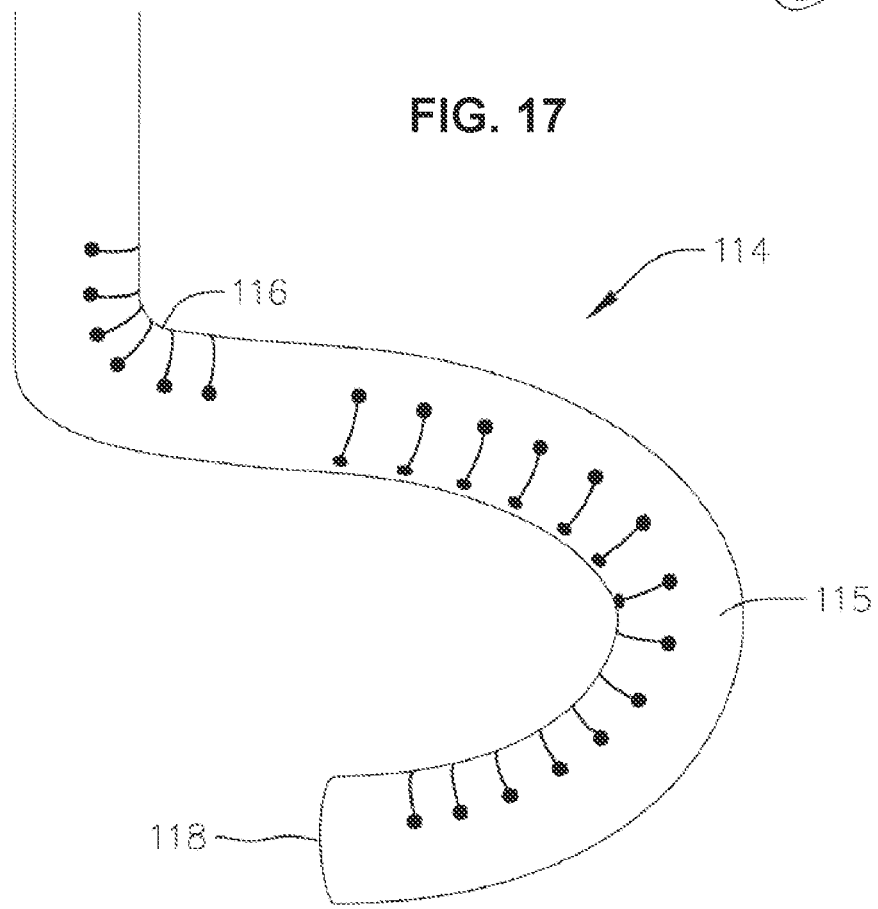
FIG. 17 shows a schematic perspective view of the delivery catheter of FIGS. 13-15 in a fully actuated state.

Referring to FIGS. 14-17, in one example embodiment, the distal region 117 of the delivery catheter 114 (which can be the same as or similar to delivery catheter 64 and/or be used to make delivery catheter 64) can be constructed of a hypotube having slits to provide controlled flexibility. The delivery catheter also has a two-control wire system that includes a first control wire 135 and a second control wire 136. FIG. 14 shows a schematic side view of a distal section 117 of an example embodiment of a delivery catheter 114. FIG. 15 shows a cross-sectional view of a multi-lumen extrusion portion of the delivery catheter 114, the cross-section taken in a plane perpendicular to a longitudinal axis of the delivery catheter, and FIGS. 16 and 17 respectively show schematic perspective views of the delivery catheter 114 in partial and fully actuated states. In some embodiments, other similar and/or different two control wire systems can be used. In some embodiments, only one control wire is used.

In certain embodiments, each of the sections 115, 116 can have an associated control wire 135, 136, for respectively controlling the bending of the sections 115, 116. The control wire 135 can extend distally past the slots 125 and can be attached to the distal region 117, for example, via welding or other attachment means at connection point 135a. Similarly, the control wire 136 can extend distally past the slots 126 and can be welded or otherwise attached to the distal region 117 at connection point 136a. In one example embodiment, the control wire 136 and corresponding slots 126 are omitted, leaving only the control wire 135 and slots 125.

Meanwhile, on a proximal side of the distal region 117, the delivery catheter 114 includes a proximal section 140 that can be formed as a braided multi-lumen tube extrusion. As can best be seen in the cross-section of FIG. 15, the proximal section 140 of the delivery catheter 114 has one or more central lumens through which the control wires 135, 136 extend to reach the distal region 117. The control wires 135, 136 can be arranged to extend side-by-side through a central region of proximal section 140 and can then exit distally from the proximal section 140 and attached to the side walls of the distal region 117, as previously described. The central positioning of the control wires 135, 136 through the proximal section 140 can provide for an anti-whipping or anti-bending effect through the delivery catheter 114 when the control wires 135, 136 are used, allowing the delivery catheter 114 to maintain full torqueability.

In addition, the proximal section 140 has a main lumen 141 that is offset from the center of the extrusion. The main lumen 141 is sufficiently sized for the valve repair or replacement device to pass and be delivered therethrough. The main lumen 141 can have, for example, an ovoid cross-section, a circular cross-section, or can have a cross-section with any other appropriate shape, so long as the valve repair or replacement device can be effectively advanced through it. In addition to the main lumen, a number of optional parallel dummy lumens can also be formed in and extend longitudinally through the proximal section 140, in order to affect a symmetric moment of inertia about the control wires through the proximal section 140. In the embodiment shown, a first dummy lumen 142 is optionally positioned diametrically opposite the main delivery lumen 141 and is formed to be the same or substantially the same shape as the main lumen 141 (e.g., ovoid in the illustrated embodiment). In addition, two more optional dummy lumens 143 are positioned diametrically opposite one another and circumferentially between the lumens 141 and 142. The additional dummy lumens 143 are illustrated to be slightly smaller than the lumens 141, 142, and have a more circular shape. In practice, the size and shape of the dummy lumens 143 can otherwise vary and will generally be selected based on the respective sizes of the lumens 141, 142, and the amount of space remaining in the extrusion. In addition, the main lumen 141 and the first dummy lumen 142 can also have variable sizes and shapes, depending on the particular application. Furthermore, in some embodiments, more or less than four total lumens can be formed in the proximal section 140, to affect a desired symmetry and moment of inertia, and to even out the stiffness, about the control wires that run through the center axis of the proximal section 140.

Referring back to FIGS. 13 and 14, in practice, once the guide sheath 220 is arranged as desired (e.g., with the distal end in the desired chamber of the heart and/or in proximity to a native annulus), distal regions of the delivery catheter 64, 114, including distal tip region 117, and in some embodiments, a portion of proximal section 140, are advanced out of the distal opening of the guide sheath 220. Here, the portions of the delivery catheter 64, 114 that extend out of the guide sheath 220 can be positioned in a desired chamber of the heart (e.g., in the left atrium for accessing the mitral valve). In some cases, part of the delivery catheter 64, 114 or distal end thereof can also extend into a second chamber as well (e.g., slightly into the left ventricle through the native mitral valve, etc.). The central control wires 135, 136 can then be tensioned in order to actuate the distal region 117 and to gain articulation of the one or two bends in sections 115, 116 at the distal portions of the delivery catheter 64, 114. The control wires 135, 136 can be tensioned partially or fully in different amounts and/or orders to properly and safely navigate around the patient's anatomy during actuation.

The design of the proximal section 140 and the central arrangement of the control wires 135, 136 provides for an anti-whipping or anti-bending effect through the delivery catheter 64, 114 when the control wire(s) 135, 136 are operated, allows for maintaining of full torqueability of the delivery catheter 64, 114 through the trans-septal bend, and facilitates the actuated shape of the distal region 117 to be held and maintained more effectively.

In some embodiments, a delivery catheter for delivering a device to a native valve of a patient's heart has a flexible tube with a centered main lumen and a control wire lumen. Referring now to FIGS. 18A-18D, a flexible tube frame 1025 of the distal end of a flexible delivery catheter in accordance with an example embodiment is shown. This flexible tube frame 1025 can have an overall cylindrical shape, open at both proximal and distal ends, and provides controlled flexibility to a flexible tube at the distal end of a delivery catheter. As with the various example embodiments described herein, the flexible tube frame, and distal region of the delivery catheter are not limited to a cross-section with a circular shape; the cross-section can also be elliptical or ovoid in shape.

Figure 18A:
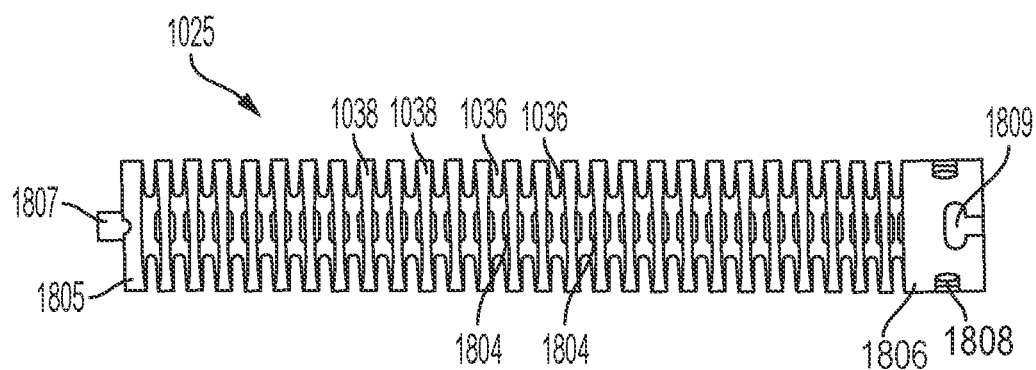
FIG. 18A shows a top view of an example distal section of (or usable in) a delivery catheter as part of a delivery device or system for implanting a valve repair or replacement device.
Figure 18B:
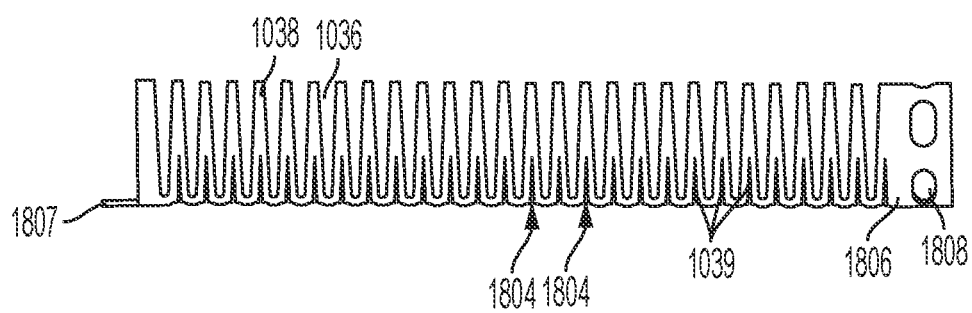
FIG. 18B shows a side view of the example distal section illustrated in FIG. 18A.
Figure 18C:
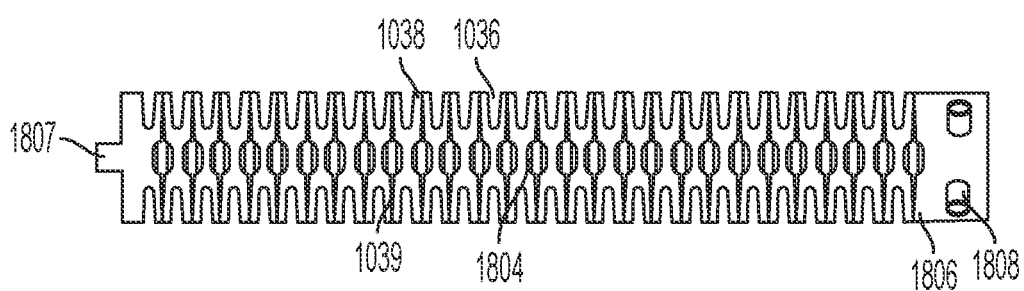
FIG. 18C shows a bottom view of the example distal section illustrated in FIG. 18A.

Referring to FIG. 18A, a top view of a flexible tube frame of the delivery catheter is illustrated. The flexible tube frame 1025 can be made of links 1038, which are defined by slots or grooves 1036. The links 1038 can also have cut-outs 1804, and slits 1039. Each of the plurality of links 1038 can have a circular shape, and each link can be spaced apart from at least one other link by a slot 1036 (or groove) at the tops and sides of the links, in a circular configuration. Referring now to FIG. 18B, a side view of the flexible tube frame is illustrated, with cut-outs 1804 and slits 1039 positioned near the bottom of the frame. The cut-outs 1804 can be curved in shape, such as a semi-circle or semi-oval cut-out from the frame. There can be a cut-out that corresponds to each of the plurality of links, on each side of the frame 1025 (see FIGS. 19A and 19B) so that when the frame is in a tubular configuration, each pair of cut-outs 1804 align to form a circle, oval, or cylindrical shaped opening, positioned along the bottom of the frame, as illustrated in FIG. 18C. The slits 1039 as illustrated in FIGS. 18B and 18C can be cut into the frame such that there are two slits cut into each of the plurality of links, which extend partially upward from the frame bottom into the associated link. There is little to no space created by the slits when the flexible tube frame is straight, but the frame links can each expand at the slits when the frame is moved into a curved configuration.

Figure 18D:
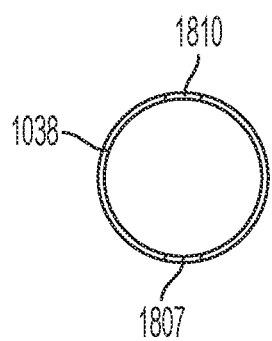
FIG. 18D shows an end view of the example distal section illustrated in FIG. 18A.

Referring now to FIG. 18D, a distal end of the flexible tube frame 1025 is illustrated. The cut-out 1810 for connecting a control wire is at the top of the distal end, and the tooth 1807 for securing the anchor ring is at the bottom of the distal end.

Figure 19B:
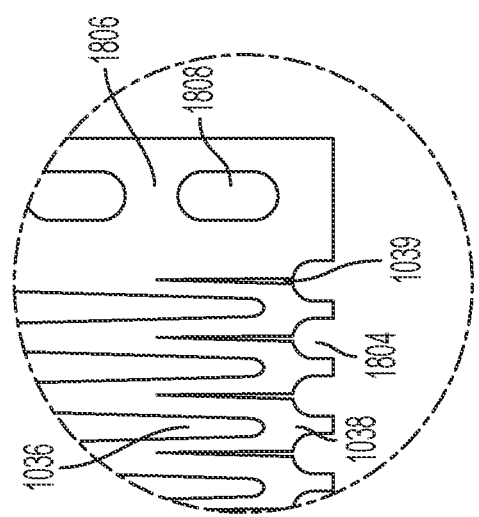
FIG. 19B shows a close-up view of a portion of the laser cut sheet of FIG. 19A.

Referring now to FIGS. 19A and 19B, a flat view of the flexible tube frame in a flat configuration is illustrated. The flexible tube of the delivery catheter can have a flexible tube frame made of a plurality of links disposed in the distal region of the flexible tube, the plurality of links positioned between the first ring and the second ring. The plurality of links can be cylindrically shaped, and cut from a single piece of material, such that each link is aligned with and connected to at least one adjacent link, with a slot formed between each pair of adjacent links. The flat sheet can be a hypotube having properties similar to or the same as the example embodiments described above and illustrated in FIG. 9 having the slots 1036, cut-outs 1804, and slits 1039 formed by laser cutting. FIG. 19A illustrates an example embodiment of the flexible tube frame in a flat configuration, and FIG. 19B illustrates a close-up view of a corner of the frame, in FIG. 19A. The frame 1025 can be rectangular or substantially rectangular in shape when in the flat configuration, with the length L modified by cut-outs 1804 and slits 1039. The slots 1036 can be cut out of a central region to form the plurality of links 1038. The slots can have an elongated and/or tapered shape, such that the center region 1901 of each slot 1036 is greater in length L2 than the length L3 of the ends of each slot. The edges of the frame 1025 along each width W can also be altered by additional cut-outs. The first end of the frame can have a cut-out that is rectangular or substantially rectangular in shape with another cut-out that is semi-circular or substantially semi-circular, aligned with a midpoint of the width W of the frame. These cut-outs in the first end create two end pieces 1902, 1903 that when the frame is in a tubular configuration, provide a tooth 1807 attachment point for a pull ring 2001, which is positioned at the bottom of the frame. The tooth 1807, however, is not limited to being formed by two end pieces, but instead can be one end piece that extends distally from distal edge 1904 of the sheet. The semicircular cut-out 1804 is positioned at the top of the first end of the frame, when the frame is in a tubular configuration, and can be clocked with a control wire, when the distal end of the delivery catheter is assembled. In this example embodiment, one control wire (e.g., pull wire, etc.) is used to control the curvature of the distal region of the delivery catheter, but the device is not so limited in other example embodiments, where the delivery catheter can have more than one control wire.

The cut-outs at a second end 1806 of the frame can be a plurality of oval shaped or substantially oval shaped windows 1808. The center window can have an additional proximal cut in it, which can be a proximal slot 1809, so that the center window is open to a proximal edge 1905 of the frame. The proximal slot 1809 can be aligned with the hypotube anchor when the delivery catheter is fully assembled. The windows can be used to provide an opening for adhesive material or polymer material to flow through and adhere to a layer underneath, or interior to, the window, embedding the component (the frame in this instance) and therefore securing it in place.

Figure 20A:
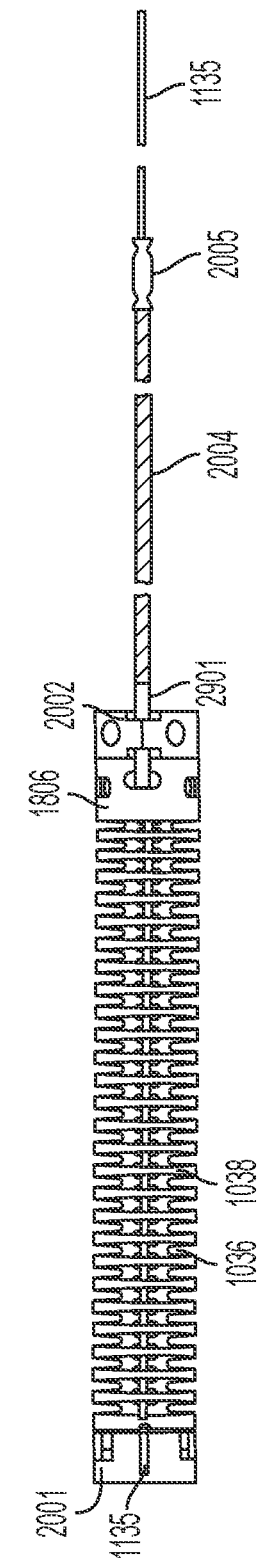
FIG. 20A shows a top view of an example distal section of (or usable in) a delivery catheter with a control wire running therethrough.
Figure 20B:
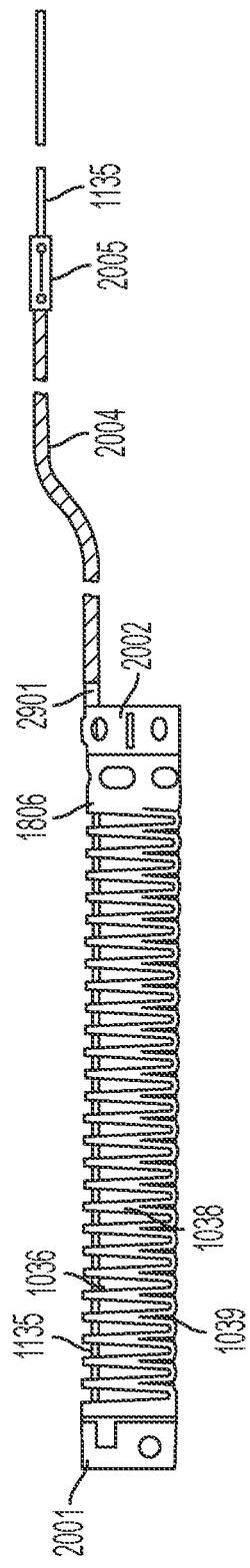
FIG. 20B shows a side view of the example distal section of (or usable in) a delivery catheter with a control wire running therethrough illustrated in FIG. 20A.

Referring now to FIGS. 20A and 20B, a control wire 1135 and other components are assembled with the flexible tube frame to control the bending of the flexible tube frame by using the control wire. The components include a first optional ring added at a distal end of the flexible tube frame, and a second optional ring added at a proximal end of the flexible tube frame.

The first ring at the distal end of the flexible tube frame can be a pull ring 2001, connected to the tooth 1807 at the distal end of the frame. The pull ring is fixedly attached to the distal end and can be attached by a weld between the pull ring and the tooth. The pull ring and distal end of the frame can alternatively be attached by any other known technique typically used and that can withstand a tensile load of at least 25 pounds. The pull ring can have cut-outs 1804 which can overlap with cut-outs of the flexible tube frame. The control wire 1135 can be fixedly attached to the pull ring.

Figure 21A:
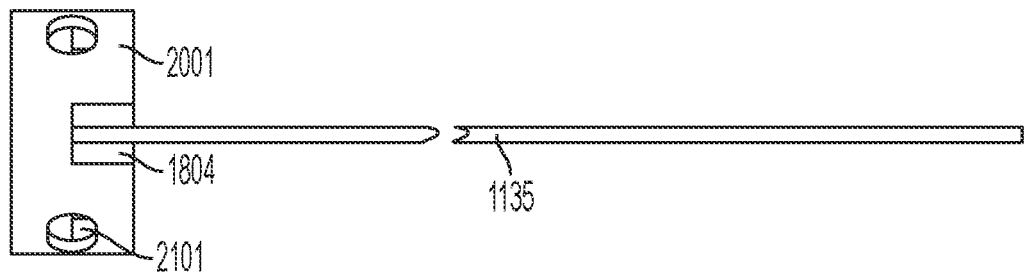
FIG. 21A shows a top view of an example distal pull ring attached to a control wire.
Figure 21B:
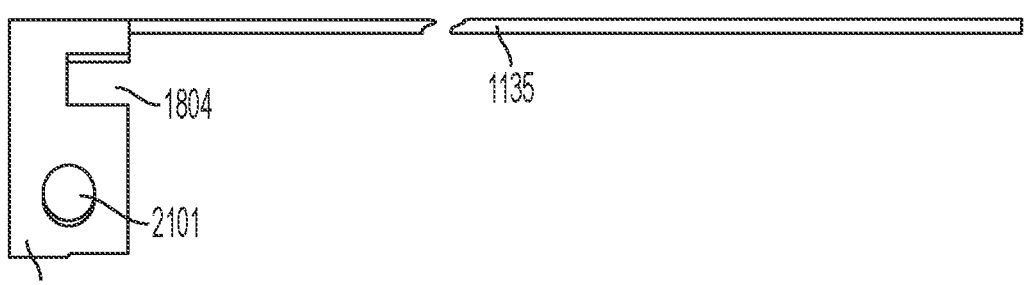
FIG. 21B shows a side view of the example distal pull ring attached to a control wire of FIG. 21A.
Figure 21C:
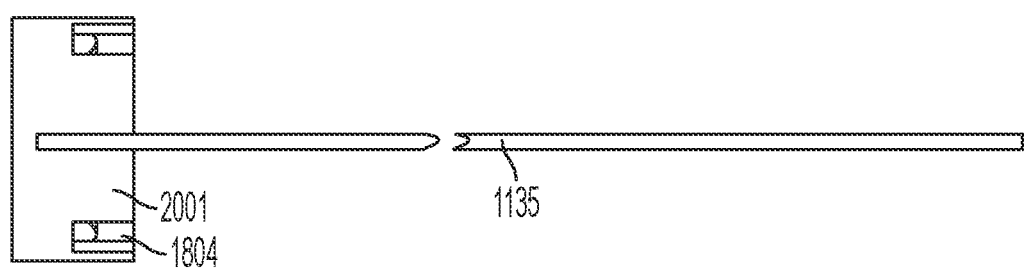
FIG. 21C shows a bottom view of the example distal pull ring attached to a control wire of FIG. 21A.

Referring now to FIGS. 21A-21C, a pull ring 2001 attached to a control wire 1135, such as that used in the example embodiment of FIGS. 20A and 20B, is illustrated. FIG. 21A illustrates a top view of the pull ring and control wire assembly. The pull ring 2001 has openings 2101. FIG. 21B illustrates a side view of the pull ring and control wire assembly. The pull ring can have additional cut-outs 1804, such as those on the proximal end of the pull ring in FIGS. 21B and 21C. The additional cut-outs can facilitate positioning of the pull ring on the distal end of the flexible tube frame. For example, cut-out 1804 is positioned on the bottom of the pull ring and aligns with the tooth 1807 of the flexible tube frame when assembled.

FIG. 21C, which is a bottom view of the pull ring and control wire, has a bottom cut-out 1804 of a size and shape to align with the tooth, and also reveals a view of the distal end of the control wire 1135.

FIG. 20A illustrates a top view of the assembly, and the control wire 1135 extends along the length of the flexible tube frame 1025 and is visible at each slot 1036. FIG. 20B illustrates a side view of the assembly and the control wire 1135 is visible running along the top interior of the flexible tubular frame.

There can be a second ring in the distal region of the flexible tube that is an anchor ring 2002. The second ring in the distal region of the flexible tube is spaced apart from the first ring. The anchor ring 2002 is attached to the proximal end of the flexible tube frame. The anchor ring 2002 can have a hypotube 2901 (see FIGS. 29A and 29B) attached to the inside top surface of it, and the control wire, which passes through the flexible tube frame, is slidably positioned within the hypotube 2901.

Figure 28A:
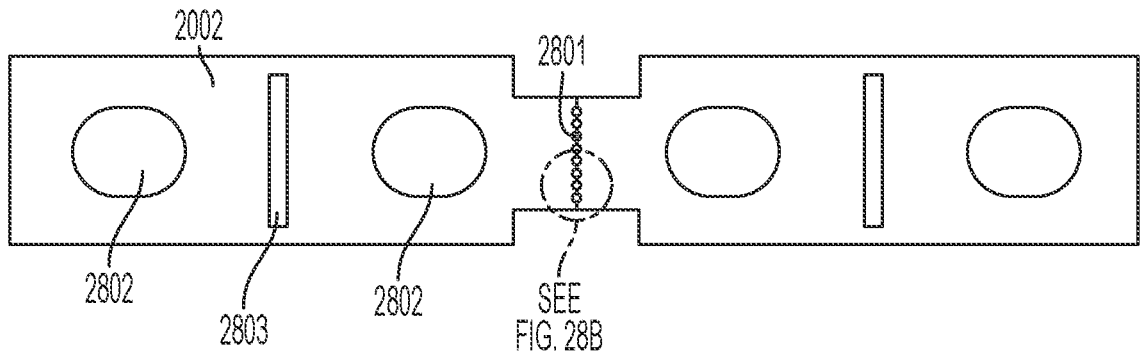
FIG. 28A shows a flat view of an example anchor ring for a distal portion of a delivery catheter.
Figure 29A:
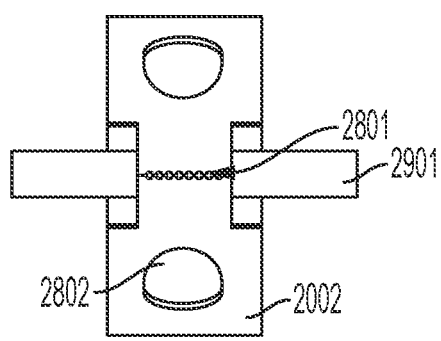
FIG. 29A shows a top view of the example anchor ring of FIG. 28A with a hypotube according to an example embodiment.
Figure 28B:
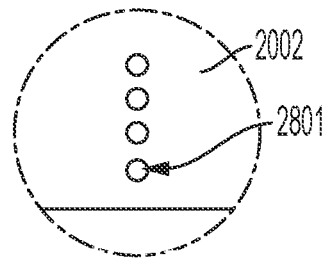
FIG. 28B shows a close-up view of a portion of the anchor ring of FIG. 28A, having weld holes.
Figure 29B:
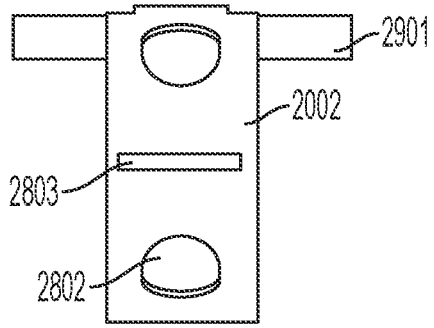
FIG. 29B shows a side view of the example anchor ring of FIG. 29A.
Figure 29C:
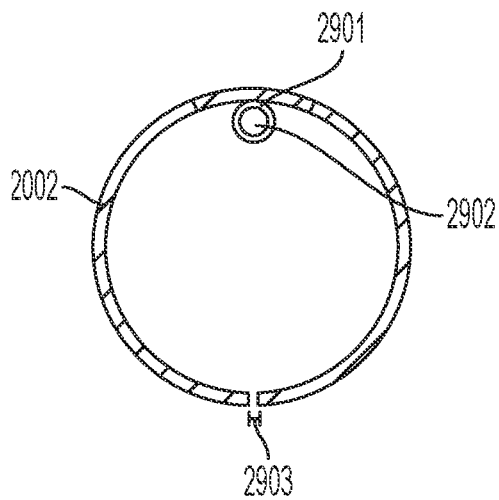
FIG. 29C shows an end view of the example anchor ring of FIG. 29A.

Referring to FIGS. 28A-29C, an anchor ring and hypotube assembly according to the example embodiment of FIGS. 20A and 20B is illustrated. FIG. 28A illustrates a flat view of the anchor ring 2002. When flat, the anchor ring can have a rectangular or substantially rectangular shape, with a width about the same as that of the flexible tube frame when in a flat configuration. The anchor ring 2002 can have cut-outs 2803, which can be rectangular in shape. The anchor ring can also have its own holes 2802. The holes 2802 and cut-outs 2803 can be circular or substantially circular and can also be rectangular, or any other shape that permits layering of materials in the assembly of the delivery catheter. The anchor ring can also have weld holes 2801 for the alignment of and welding of a hypotube 2901 to the top-inside of the anchor ring. FIG. 28A illustrates a close-up view of the weld holes. FIG. 29A illustrates a top view of the anchor ring and hypotube 2901 welded together. The hypotube is an anchor for the control wire to slidably pass through. FIG. 29B is a side view of the anchor ring 2002 and hypotube 2901. FIG. 29C illustrates an end view of the anchor ring. The hypotube can be positioned and welded to the interior surface of the top of the anchor ring. The anchor ring can be curved into a cylindrical configuration to match that of the flexible tube frame; however the ends of the anchor ring are not required to be in contact with each other to form a complete cylinder or other substantially cylindrical shape. FIG. 29C illustrates a gap 2903 which can remain once the components are assembled. The weld between the anchor ring and the hypotube should be able to withstand a tensile load of at least 30 pounds, with the load being applied in a coaxial direction to the hypotube.

Figure 30A:
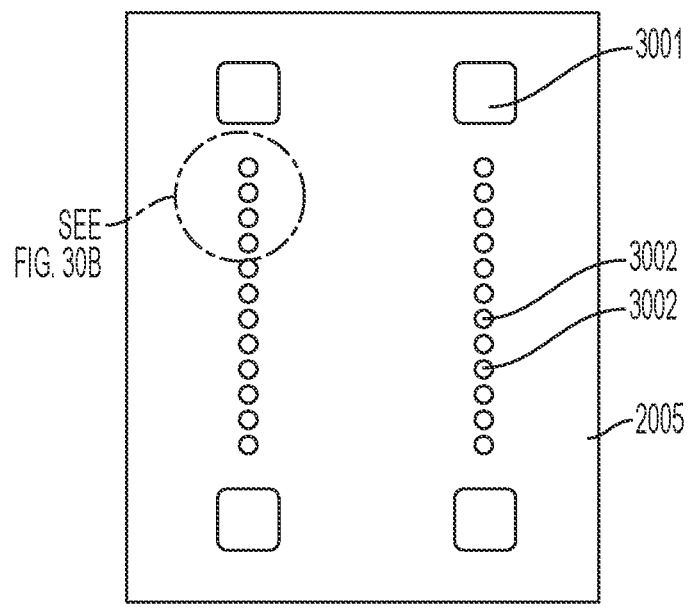
FIG. 30A shows a flat view of an example coil stopper.
Figure 30B:
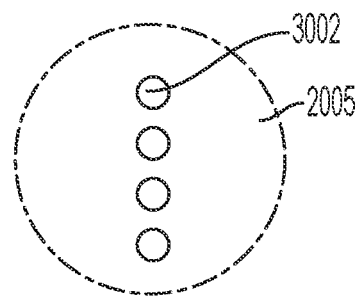
FIG. 30B shows a close-up of weld holes in the example coil stopper of FIG. 30A.

Referring now to FIGS. 30A-31C, the coil sleeve 2004 and proximal coil stopper 2005 are described in greater detail. FIG. 30A illustrates a flat view of the proximal coil stopper 2005. The proximal coil stopper can have windows 3001 and weld holes 3002. The windows allow assembly of the components to be held together with the polymer catheter material, and the weld holes permit the proximal coil stopper to be secured to the coil sleeve. FIG. 30B illustrates a close up of the weld holes 3002 which can be used to weld the proximal coil stopper 2005 to the coil sleeve 2004.

Figure 31A:
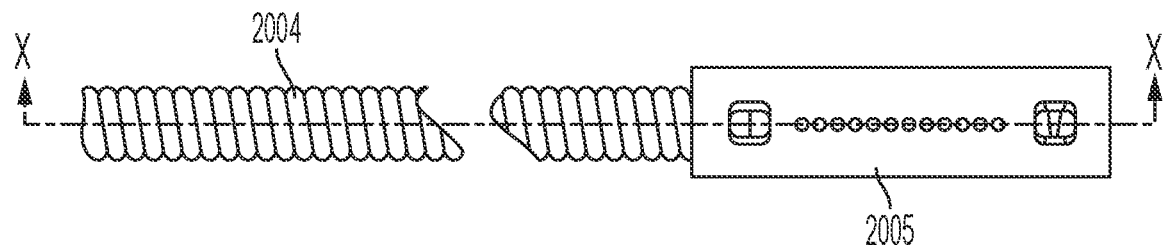
FIG. 31A shows a top view of an example coil stopper with a portion of a coil.
Figure 31B:
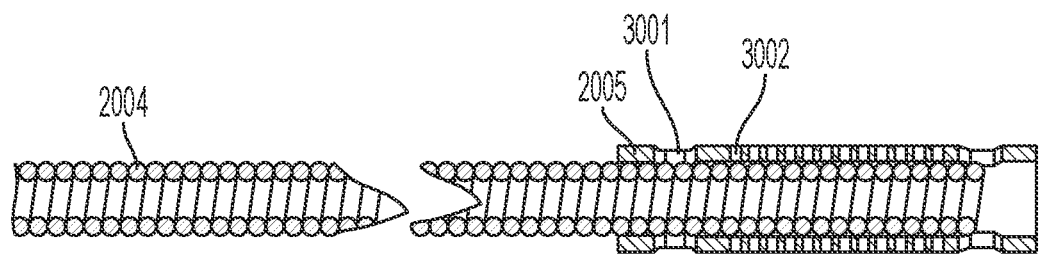
FIG. 31B shows a cross-section view of the example coil stopper and coil taken along line X-X of FIG. 31A according to an example embodiment.
Figure 31C:
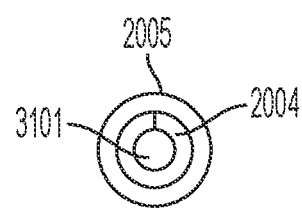
FIG. 31C shows an end view of the proximal end of the example coil stopper and coil of FIG. 31A.

FIGS. 31A-31C illustrate a proximal region of the coil sleeve 2004 as it is assembled with the proximal coil stopper 2005. In FIG. 31A, a top view is illustrated. Here the assembly windows are positioned so that there is a top proximal window and a top distal window. Each of the assembly windows in FIG. 31A can be part of a pair, having a corresponding bottom assembly window, as shown in FIG. 31B. The proximal coil stopper is not limited to this particular configuration of assembly windows and weld holes. FIG. 31B illustrates a cross-section of the coil sleeve and proximal coil stopper taken along line X-X. A proximal end of the coil sleeve 2004 fits snugly within the proximal coil stopper. The weld holes are on both the top and bottom of the proximal coil stopper. The weld holes are in the proximal coil stopper so that a plurality of rotations of the coil in the coil sleeve can be fixed to the proximal coil stopper. FIG. 31C illustrates the coil within the proximal coil stopper, and the channel 3101 in which the control wire slidably extends through. The weld between the proximal coil stopper and the coil sleeve should be able to withstand a compressive load of at least 35 pounds.

Figure 22A:
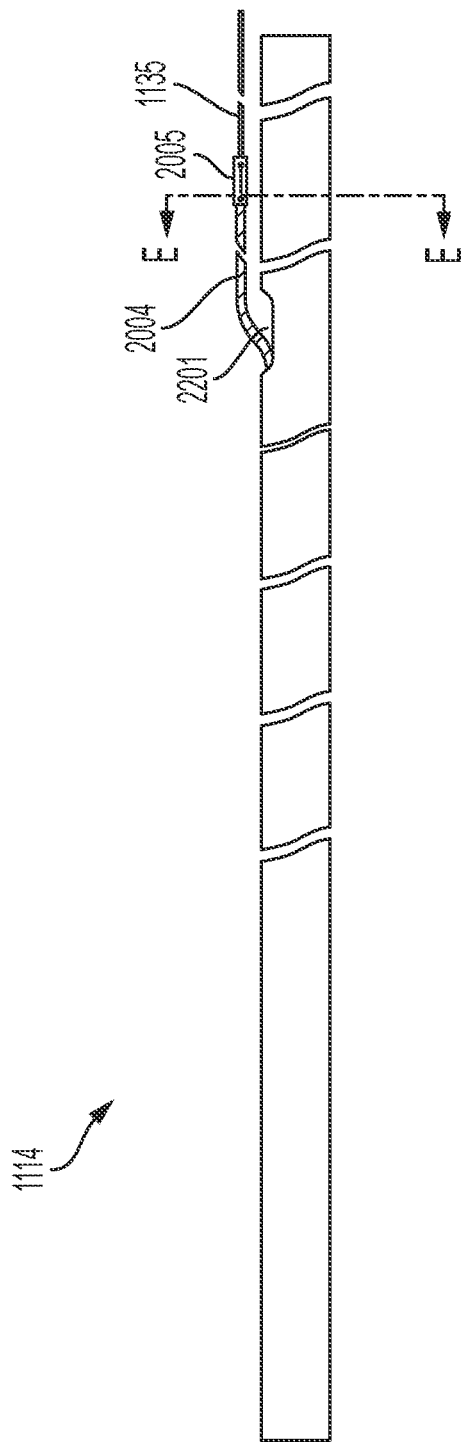
FIG. 22A shows a side view of an example shaft of a steerable catheter.
Figure 22B:
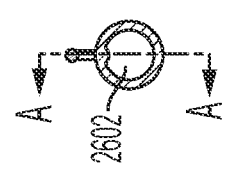
FIG. 22B shows an end view of the example shaft of the steerable catheter of FIG. 22A.

Referring now to FIGS. 22A and 22B, the distal portion of a delivery catheter 1114 containing a flexible tube frame is illustrated. FIG. 22A illustrates a side view, showing an outer layer that is a polymer coating. The polymer coating can be a thermoplastic elastomer (TPE), that can be a polyether block amide (PEBA). The properties of the polyether block amide can vary along the length of the distal end of the catheter and can be chosen based on the desired flexibility and number of components of each portion of the catheter. At a proximal location along the length of the delivery catheter, the catheter 1114 has an opening 2201 for the control wire 1135 to exit from. The coil sleeve 2004 surrounds the control wire until the control wire passes through the proximal coil anchor. FIG. 22B illustrates a distal end view of the delivery catheter.

Figure 23A:
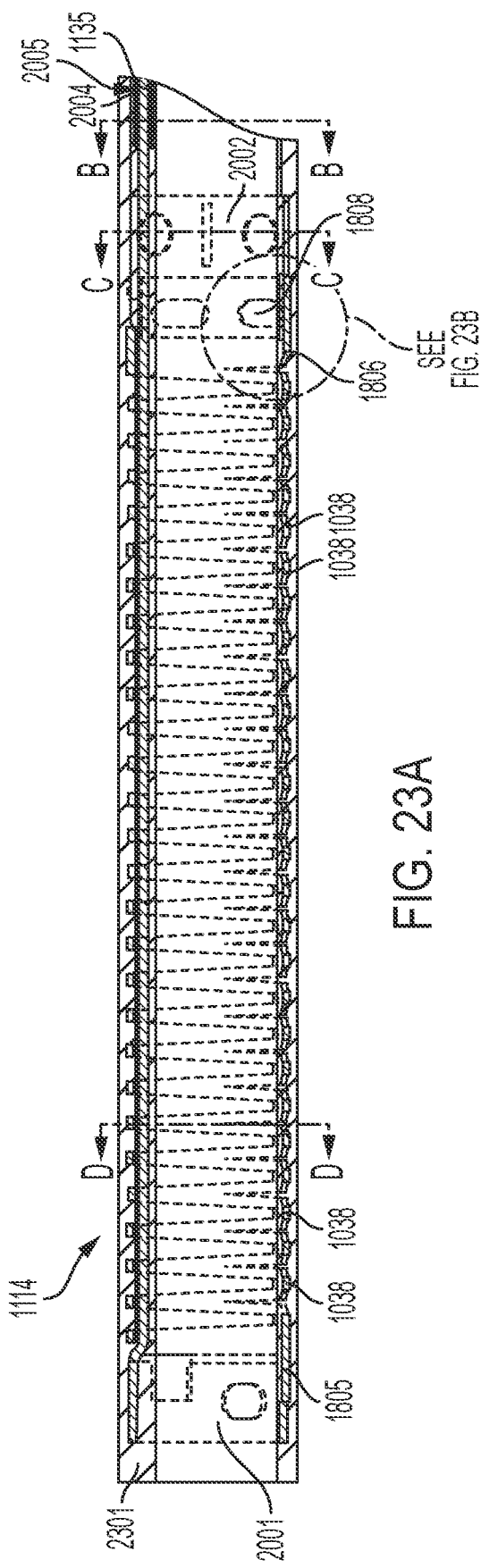
FIG. 23A shows a cross-section view of the example shaft of the steerable catheter, taken along line A-A of FIG. 22B.
Figure 23B:
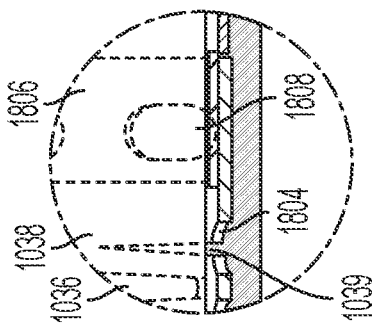
FIG. 23B shows a close-up view of a portion of the cross-section view of the example shaft of the steerable catheter of FIG. 23A.

Referring now to FIGS. 23A and 23B, a cross section of the distal end of the delivery catheter, is illustrated, taken along line A-A of FIG. 22B. FIG. 23B is a close-up view of a portion of the cross-section of FIG. 23A.

The components illustrated in the various cross-sections of FIGS. 22A-23A can extend various lengths along the delivery catheter in certain example embodiments. For example, the flexible tube frame 1025 extends along a distal region of the delivery catheter. The coil sleeve 2004 is proximal to the flexible tube frame and extends for a length inside the control wire lumen, then exits the delivery catheter and extends in a proximal direction for another length. The braid 2401 extends along a central region of the delivery catheter. The primary catheter lumen liner can extend along the entire length of the delivery catheter. The control wire lumen liner can extend along the entire length of the control wire lumen.

FIG. 23A illustrates the position of the control wire 1135, from the distal end of the control wire, secured to the pull ring, to a portion of the control wire that is surrounded by the coil sleeve. The coil sleeve 2004 covers a portion of the control wire that is proximal to the anchor ring. As shown in FIGS. 23A and 23B, the delivery catheter can be configured such that the flexible tube frame is in contact with the outer polymer layer 2301 of the delivery catheter. The slots or grooves 1036 of the flexible tube frame are positioned at the top and sides of the frame and the slits and cut-outs are at the bottom of the frame.

Figure 24:
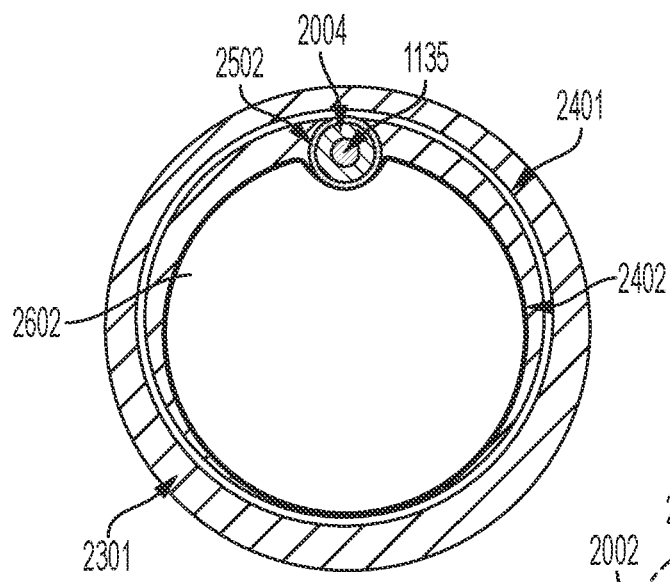
FIG. 24 shows a cross-section view of the example shaft of the steerable catheter of FIG. 22A taken along line B-B of FIG. 23A.
Figure 25B:
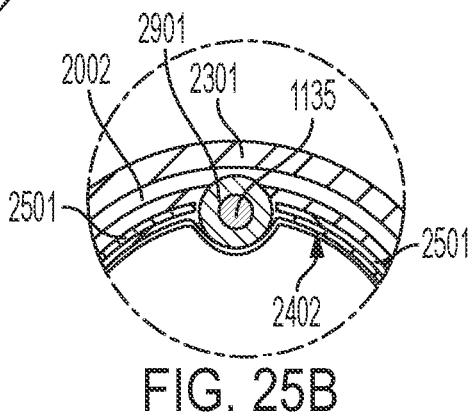
FIG. 25B shows a close up of a portion of the cross-section view of FIG. 25A, having a control wire.
Figure 25A:
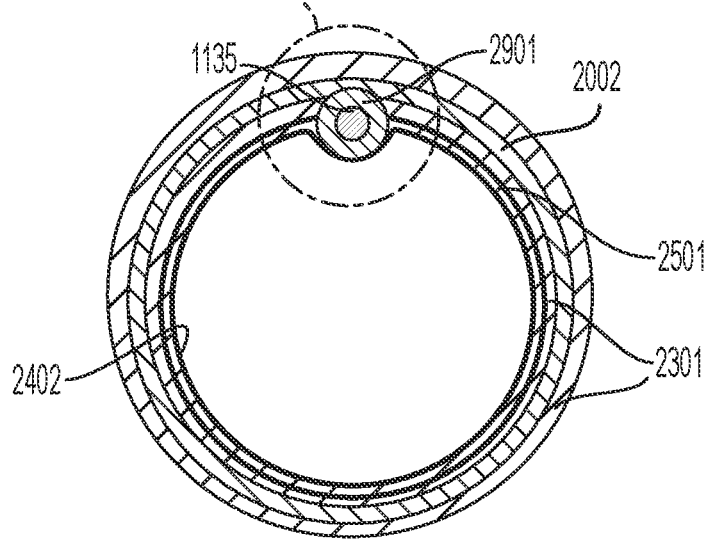
FIG. 25A shows a cross-section view of the example shaft of the steerable catheter of FIG. 22A taken along line C-C of FIG. 23A.
Figure 26:
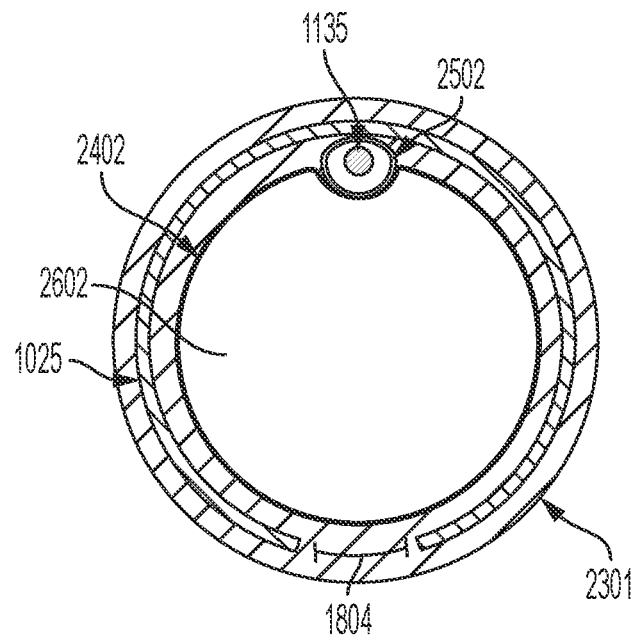
FIG. 26 shows a cross-section view of the example shaft of the steerable catheter of FIG. 22A taken along line D-D of FIG. 23A.
Figure 27:
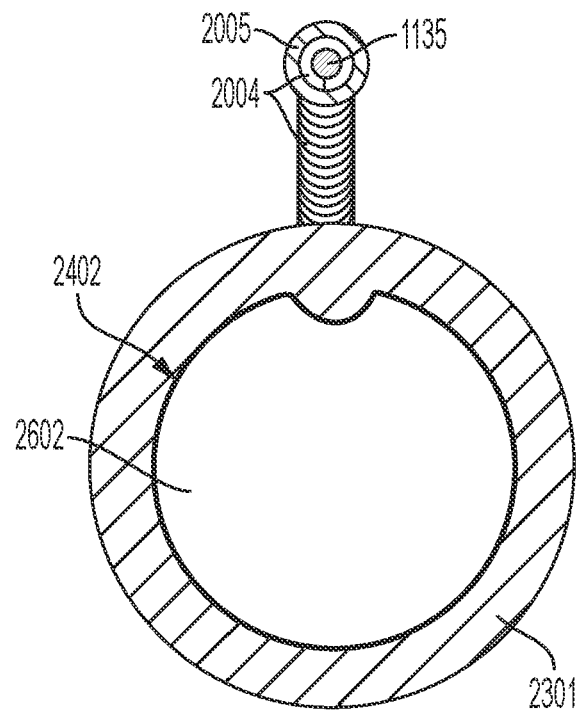
FIG. 27 shows a cross-section view of the example shaft of the steerable catheter of FIG. 22A taken along line E-E of FIG. 22A.

Referring now to FIGS. 24-27, cross-sections of the delivery catheter are illustrated, taken along various points along the length of the catheter. FIGS. 24-26 illustrate cross-sections from the distal region of the delivery catheter and include the flexible tube frame 1025. FIG. 27 illustrates a cross-section from a proximal region of the delivery catheter, where the control wire is positioned external to the catheter.

Referring to FIG. 24, the cross-section of the delivery catheter illustrated is taken along line B-B of FIG. 23A. This cross-section is at a proximal portion of the distal region. There is an outer layer 2301 of the catheter that can be an outer polymer layer having any of the properties described above regarding polymers used for delivery catheters. There is an inner layer that is a primary lumen liner 2402, which can be made of etched PTFE, and extends the full length of the primary lumen of the delivery catheter. The liner fully surrounds the interior surface of the catheter lumen, to provide a smooth surface so that a valve implant device can be passed through without catching on the interior surface and delivered to a heart valve. There can be a braid 2401 that provides additional support to the catheter without limiting the flexibility needed to navigate the delivery catheter inside the heart. The braid 2401 is embedded in the outer polymer layer. The braid can be made of a flat wire(s) and/or round wire(s) and can have an almond-shaped pattern, or any other pattern known in the art to provide both strength to and retain flexibility in a delivery catheter. There is a control wire lumen 2502 that is at the top of the tube, and in this lumen, at cross section B-B, is a control wire lumen liner 2502 lining the control wire lumen, and a coil sleeve 2004 surrounding a control wire 1135. There remains a hollow primary lumen 2602 in the catheter inside the primary catheter lumen liner 2402.

Referring to FIG. 25A, the cross-section of the delivery catheter illustrated is taken along line C-C in FIG. 23A. This cross-section is at an intermediate portion of the distal region of the delivery catheter, at a location just proximal to the flexible tube frame where the anchor ring is located. FIG. 25B illustrates a close-up view of the top of the catheter at the cross section shown in FIG. 25A, where the control wire lumen is located. Hypotube 2901 is attached to anchor ring 2002, and the control wire 1135 extends through hypotube 2901. The hypotube can be made of stainless steel, polymer, or other biocompatible material.

There can also be a marker band 2501. The marker band can provide an indicator to the user of the location of the proximal end of the flexible tube frame in the distal region of the delivery catheter. The marker band can be made of platinum iridium or other material that would be readable with the imaging techniques commonly used in conjunction with mitral valve implant delivery catheters. Liner 2401, which is the liner of the primary lumen 2602 of the catheter, can extend along the entire length of the lumen 2602, including at the portion of the distal region of the delivery catheter at line C-C.

Referring to FIG. 26, the cross-section of the delivery catheter illustrated is taken along line D-D in FIG. 23A. This cross-section is more distally located in the distal region of the delivery catheter. At this cross-section, there is the flexible tube frame 1025 embedded in the outer catheter 2301. This particular cross-section is taken at a part of the catheter having a cut-out 1804 at the bottom of the flexible tube frame, as indicated by the gap 2601. The interior of the primary catheter lumen and the control wire lumen are each lined with a primary lumen liner 2402 and a control wire lumen liner 2502, respectively. The control wire lumen is occupied by the control wire. The outer catheter is made of a polymer as described above.

FIG. 27 illustrates the cross-section taken along line E-E of FIG. 22A, in a proximal region. The primary catheter lumen 2602 has a liner 2402, which extends along the length of the delivery catheter. The control wire lumen begins at a more distal location in the catheter. At cross-section E-E, the control wire has exited the catheter so that it can be manipulated at its proximal end (not shown) by an operator. The control wire 1135 is surrounded by a coil sleeve 2004 and the coil sleeve is partially covered by the proximal coil stopper 2005.

Referring again to FIGS. 20A and 20B, the delivery catheter can have a control wire in the control wire lumen 2502 (see FIG. 26). The control wire lumen 2502 can be connected to pull ring, and extend at least along the delivery catheter, at an inside location along the flexible tube frame (i.e., in the interior of the flexible tube frame). The hypotube of the anchor ring and a coil sleeve 2004 are disposed in the control wire lumen. The coil is located proximal to the flexible tube frame and is connected to a proximal end of the hypotube 2901. The coil surrounds the control wire to protect it and to prevent the plastic material around the coil sleeve from compressing, foreshortening, or buckling when the control wire is pulled. A proximal coil stopper 2005 can surround the proximal end of the coil sleeve. The coil sleeve 2004 has a distal region within the catheter, in the control wire lumen, and exits the catheter at opening 2201. A proximal region of the coil sleeve is external to the delivery catheter and extends for a length. At least the portion of the control wire that extends from the second ring to the first ring is not covered by the coil sleeve (see FIG. 26). The coil stopper 2005 maintains the integrity of the proximal end of the coil sleeve 2004 and provides a means for connecting the coil sleeve to other components of the catheter, such as the pull ring. The coil sleeve acts as a stopper to the control wire, to stop it from compressing, foreshortening, or buckling the proximal region of the delivery catheter. The coil stopper and coil sleeve can be configured in a variety of different ways and may in some embodiments be omitted.

The delivery catheter 114 includes a control wire lumen 2502 for housing the control wire 1135. In the illustrated embodiment, the control wire conduit is defined, at least in part, by a liner. In some embodiments, the control wire conduit 2502 can take any other suitable form.

In some embodiments, the delivery catheter 114 includes a coil sleeve 2004 that extends around the control wire until it reaches the flexible tube frame 1025. The design of the proximal section of the delivery catheter and the arrangement of the control wire 1135 and coil sleeve 2004 provides for an anti-whipping or anti-bending effect through the delivery catheter 114 when the control wire is operated. This can allow for maintaining full torqueability of the delivery catheter 114 through the trans-septal bend. This can also facilitate the actuated shape of the distal region 25 to be held and maintained more effectively during torqueing or rotation during delivery. The coil sleeve 2004 is configured to provide for the anti-whipping or anti-bending effect and for maintaining the full torqueability of the delivery catheter 114.

Figure 20C:
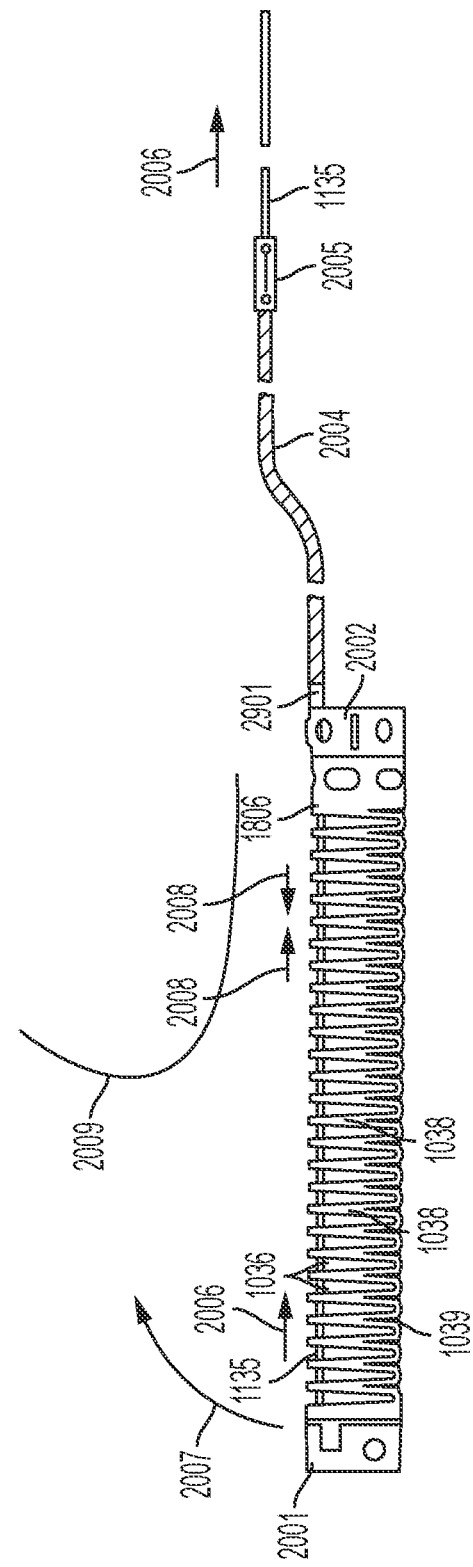
FIG. 20C shows a side view of the example distal section of (or usable in) a delivery catheter of FIG. 20B and how it moves when a control wire is pulled.

The control wire 1135, control wire conduit 2502, flexible tube frame 1035, pull ring 2001, anchor ring 2002, and coil sleeve 2004 operate in a manner similar to a cinch, or a drawstring, where the control wire is the string, and the flexible tube frame allows the distal region of the catheter to be "cinched." FIG. 20C illustrates the movement of the components when tension is applied to the control wire. At the proximal end of the device, the operator can pull the control wire 1135 in a proximal direction, as indicated by arrows 2006. The control wire can be tensioned partially or fully in different amounts to properly and safely navigate around a patient's anatomy. Upon applying this tension in a proximal direction to the control wire 1135, the control wire, connected to the pull ring 2001 at the distal end, applies a force in a proximal direction on the top of the pull ring. This force causes the pull ring 2001 to move both upward and in a proximal direction, as indicated by arrow 2007. The flexible tube frame 1025 bends and bunches along the slots or grooves 1036, so that the slots 1036 positioned along the top curve of the frame become smaller as the tops of the frame links 1036 are pulled closer together, as indicated by arrows 2008. This is what causes the flexible tube frame, and therefore the distal section of the delivery catheter, to flex so that its distal region curves upwards in the direction illustrated with arrow 2007, where the upward direction is defined as the direction that the top of the tube frame 1025 faces. The result of applying tension to the control wire 1135 by pulling it in a proximal direction is that the flexible tube frame 1025 is curved into a configuration with its proximal and distal ends brought closer together and having a curve such as that provided by the curve 2009 in FIG. 20C. In this way, the tension on the control wire is what determines the degree of curvature. As the flexible tube frame 1025 bends, the slits 1039 along the bottom of the frame can expand to alleviate force applied to the flexible tube frame.

Referring again to FIG. 20C, the control wire 1135 is fixedly connected to the pull ring 2001 and is slidably connected to the anchor ring 2002 at the proximal end of the flexible tube frame 1025 by passing through the hypotube 2901. The control wire 1135 is also slidably positioned within the control wire lumen 2502 and the coil sleeve 2004. The coil sleeve 2004 prevents cinching and/or bunching of the delivery catheter in regions other than that of the flexible tube. The coil sleeve provides additional stiffness to the delivery catheter, such that the length of the delivery catheter having the coil sleeve does not flex excessively. As the control wire 1135 is pulled in the direction of arrows 2006 to flex the distal region of the delivery catheter, a tensile load is applied to the distal end of the control wire, where it is connected to the pull ring. The flexible tube frame bends, but the coil sleeve 2004 prevents curvature of the control wire 1135 in the proximal region of the delivery catheter. When the tension in the control wire is released, the tube frame returns to a straight configuration, the plurality of links 1038 become spaced apart again along the slots and/or grooves 1036, and the slits 1039 close again.

Figure 32:
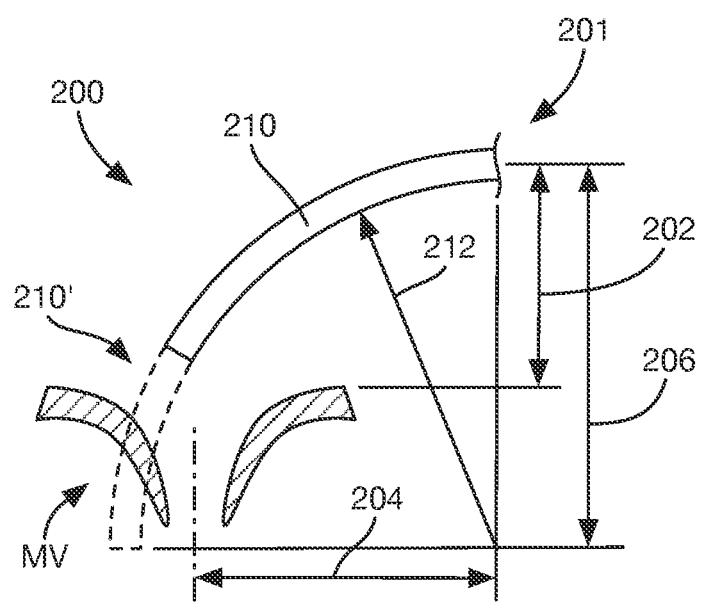
FIG. 32 is a schematic side view of an example distal end of a delivery catheter in a bent configuration according to one embodiment.

To deliver some implantable prosthetic devices, an example distal end of a delivery device may need to bend/curve about 90 degrees to properly align the implantable prosthetic device within the mitral valve. One technique used to reach the mitral valve is the trans-septal technique, mentioned above. In some trans-septal techniques, a delivery device is extended through the inferior vena cava IVC (see FIGS. 2 and 3) and then through a puncture in the septum (though in some embodiments, the septum may be accessed via the superior vena cava SVC). The height of the distal end when bent/curved to a maximum bending condition (e.g., 90 degrees) determines a minimum distance between the mitral valve and the puncture through the septum that is made during implantation, i.e., the septal puncture height. If the puncture through the septum is made too close to the mitral valve—below the minimum septal puncture height—the distal end will not be able to bend/curve to 90 degrees without contacting the tissue of heart, thereby frustrating proper alignment and implantation of the implantable prosthetic device in the mitral valve, as can be seen in FIG. 32. The delivery device can also be configured to reach the tricuspid valve TV after extending through the inferior vena cava IVC, which may require additional bending beyond 90 degrees where bend height and distance also impact alignment of the implantable prosthetic device within the tricuspid valve TV.

Referring now to FIG. 32, a schematic side view of an example distal end 200 of a delivery catheter is shown protruding through a septal puncture or opening 201 in the septum of the heart and bending toward the mitral valve MV. A guide sheath 220 (see FIG. 13), such as a trans-septal sheath, can also be used to guide the delivery catheter and/or cross the septum. The septal puncture 201 is made at a vertical distance or septal puncture height 202 above the mitral valve MV. The center of the mitral valve MV is spaced apart laterally by a lateral distance 204 from the septum. The distal end 200 has a bending portion 210 with a bending radius 212 that enables the distal end 200 of the delivery device to be bent toward the mitral valve MV to deliver an implantable prosthetic device within the valve for implantation. Similarly, in embodiments where the delivery catheter is configured to reach the tricuspid valve TV, the delivery catheter enters the right atrium RA from the inferior vena cava IVC (and/or superior vena cava SVC) and is bent toward the tricuspid valve TV to deliver an implantable prosthetic device within the valve for implantation.

As was described above and can be seen in FIG. 32, a bending height 206 of the bending portion 210 is greater than the minimum septal puncture height 202. Thus, a fully extended bending portion 210', shown in broken lines, would interfere with the native tissue of the mitral valve MV such that the implantable prosthetic device could not be implanted in the middle of the mitral valve MV using the septal puncture 201. A similar situation can arise when delivering an implantable prosthetic device in to the tricuspid valve TV if the bend radius of the delivery catheter is not tight enough to bend from the inferior vena cava IVC to the middle of tricuspid valve TV.

Figure 33:
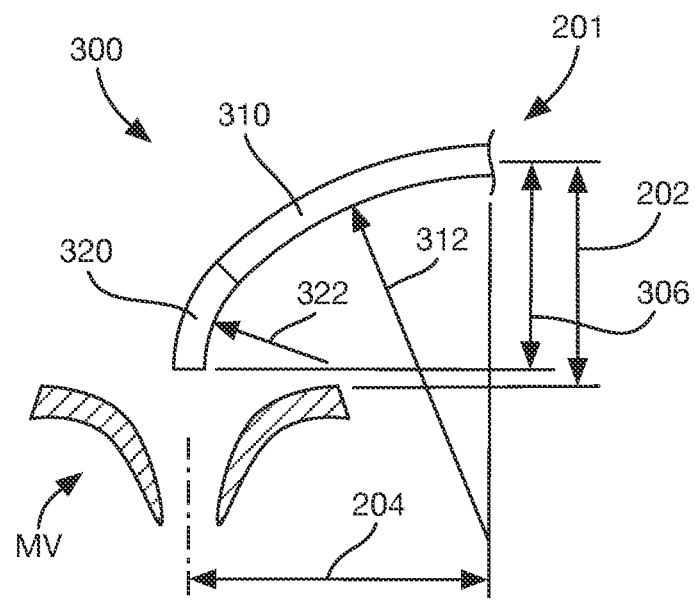
FIG. 33 is a schematic side view of an example distal end of a delivery catheter in a bent configuration according to one embodiment.

Referring now to FIG. 33, a schematic side view of an example distal end 300 of a delivery catheter (e.g., a multiple-curve/bend delivery catheter) is shown protruding through the septal puncture 201. The distal end 300 has a first bending or curved portion 310 and a second bending or curved portion 320. The first bending portion 310 is bent/curved at a first bending radius 312 and the second bending portion 320 is bent/curved at a second bending radius 322. The first bending radius 312 is greater than the second bending radius 322 so that the first bending portion 310 bends more gradually than the second bending portion 320. The tighter bend radius of the second bending portion 320 combined with the larger bending radius of the first bending portion 310 enables the distal end 300 to bend/curve a full 90 degrees with a bending height 306 that is less than the septal puncture height 202. The bending height 306 can be altered by altering the first and second bend radii 312, 322 of the first and second bending portions 310, 320, for example, by altering the stiffness of the first and second bending portions 310, 320. Various ways of altering the stiffness of the first and second bending portions 310, 320 are discussed in more detail below. The bending height 306 can also be altered by altering the relative length of the two bending portions 310, 320. For example, the first bending portion 310 can be about one-quarter, one-third, one-half, two-thirds, or three-quarters of the length of the distal end 300, with the second bending portion 320 making up the remainder of the length of the distal end 300.

Referring now to FIGS. 34-36, schematic side views of example distal ends of example delivery catheters are shown in a 90-degree bend/curve condition. FIG. 34 shows the distal end 200, described above, bent/curved to 90 degrees (or curved such that the tip is oriented in a direction 90 degrees from the direction of the catheter portion before the bend or at the septum crossing region) with a bend height 206 and a lateral bend distance 208. FIG. 35 shows the distal end 300, described above, bent/curved to 90 degrees to a bend height 306 and a lateral bend distance 308. The bend height 306 and bend distance 308 of the distal end 300 are both less than the bend height 206 and bend distance 208 of the distal end 200 because the distal end 300 includes first and second bending portions 310, 320 that have first and second bend radii 312, 322 as compared to the single bend radius 212 of the bending portion 210 of the distal end 200.

FIG. 36 shows an example distal end 400 that has an additional bending/curved portion so that the distal end 400 is formed from first, second, and third bending portions 410, 420, 430. The first, second, and third bending portions 410, 420, 430 have first, second, and third bending radii 412, 422, 432, respectively. The first and third bending portions 410, 430 have smaller bending radii 412, 432 than the second bending portion 420. Consequently, a bending height 406 of the distal end 400 is greater than the bending height 306 and less than the bending height 206. Though the bending height 406 is greater than the bending height 306, the distal end 400 has a smaller bending distance 408 than the bending distance 308 because of the addition of the first bending portion 410 with a smaller bending radius 412.

In some embodiments, distal ends, such as those described herein, can have any number of bending or curved portions with various lengths and bending radii to allow for customization of the bending height, bending distance, and shape of the distal end when bent to about a 90-degree angle or other angle as required by the desired application. The bending properties of an example distal end can be modified to target a particular bending height or bending radius that target a particular bending profile or path. For example, different bending profiles can be configured depending on whether the implantable prosthetic device is intended for delivery into the tricuspid valve TV or into the mitral valve MV via a trans-septal procedure.

As is described above, an example embodiment of a delivery catheter for delivering a device to a native valve of a patient's heart can have a centered main lumen and a control wire lumen. Referring now to FIGS. 37-43, an example flexible tube frame 500 of the distal end of a flexible delivery catheter in accordance with an example embodiment having first and second bending portions 510, 520 is shown. The flexible frame 500 extends from a proximal end 501 to a distal end 502 and can have an overall cylindrical shape that is open at both the proximal and distal ends 501, 502. The flexible frame 500 provides support and controlled flexibility to first and second polymer layers 530, 540 (FIGS. 42-43) at the distal end of a delivery catheter. As with the other example embodiments described herein, the flexible tube frame 500 and distal region of the delivery catheter are not limited to a cross-section with a circular shape (e.g., FIG. 40); that is, the cross-section can also be elliptical or ovoid in shape. In addition, the first and second polymer layers 530, 540 can be used with any of the frames described herein, such as frames having a single, uniform flexing section to form bending portions with different bending radii.

The proximal end 501 of the flexible tube frame 500 includes a plurality of rounded, oval shaped or substantially oval shaped windows or cut-outs 503 and a center cut-out or proximal slot 505 that is open to the proximal end 501 of the flexible tube frame 500. The proximal slot 505 can be aligned with a hypotube anchor when the delivery catheter is fully assembled. The plurality of cut-outs 503 are used to provide an opening for adhesive material or polymer material of the first and second polymer layers 530, 540 to flow through the flexible tube frame 500 to adhere to other materials, such as a layer underneath or interior to the cut-outs 503 thereby embedding and securing the flexible tube frame 500 in a desired location.

The distal end 502 of the flexible tube frame 500 includes a tooth-shaped attachment portion 504 protruding from the bottom side of the distal end 502 for attaching the flexible tube frame 500 to a distal pull ring 560 (FIGS. 42-43) or another pull ring such as the pull ring 2001 described above. The attachment portion 504 can be formed from a single protrusion or two protrusions that are joined together when the flexible tube frame 500 is formed from a flat sheet of material (see, for example, the flat sheet shown in FIG. 41).

Figure 40:
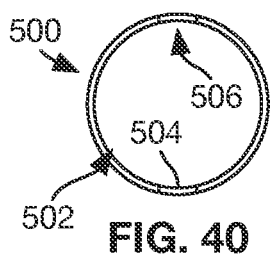
FIG. 40 shows an end view of the distal section of FIG. 37.

The distal end 502 can also include an optional semicircular shaped distal cut-out 506 positioned at the top side of the distal end 502 when the flexible tube frame 500 is formed in the tubular configuration. The distal cut-out 506 attaches to a control wire 570 (FIGS. 42-43) or another control wire such as the control wire 1135 described above. The distal end 502 of the flexible tube frame 500 is shown in FIG. 40 to show the circular cross-sectional shape of the flexible tube frame 500 and the relative positions of the attachment portion 504 and the cut-out 506.

Figure 37:
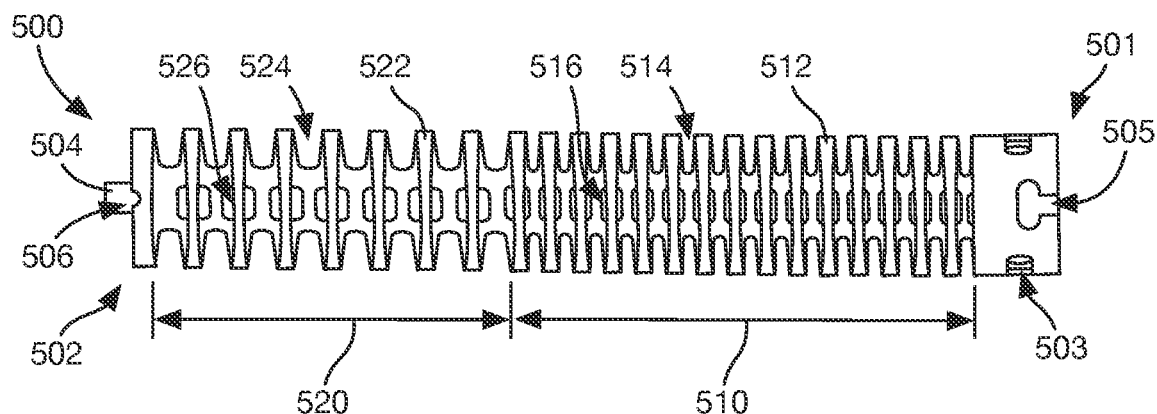
FIG. 37 shows a top view of an example distal section of (or usable in) a delivery catheter as part of a delivery device or system for implanting a valve repair or replacement device, according to an example embodiment.

Referring to FIG. 37, a top view of the flexible tube frame 500 is shown. The flexible tube frame 500 has first and second bending portions 510, 520. Each of the first and second bending portions 510, 520 is formed from a plurality of links 512, 522 that are defined by slots or grooves 514, 524. The links 512, 522 can also include cut-outs 516, 526 and slits 518, 528. Each of the plurality of links 512, 522 can have a circular shape, and is spaced apart from at least one other link by a slot or groove 514, 524 at the tops and sides of the links 512, 522 in a circular configuration.

Figure 38:
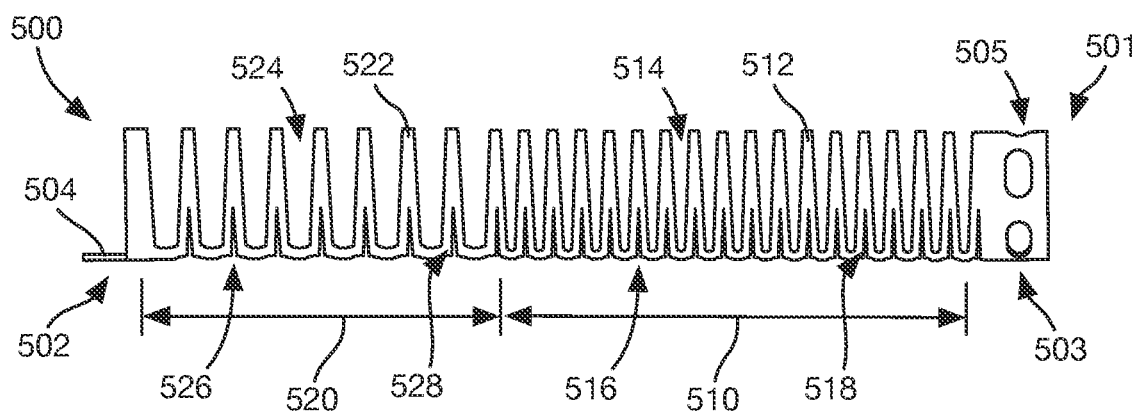
FIG. 38 shows a side view of the distal section of FIG. 37.
Figure 39:
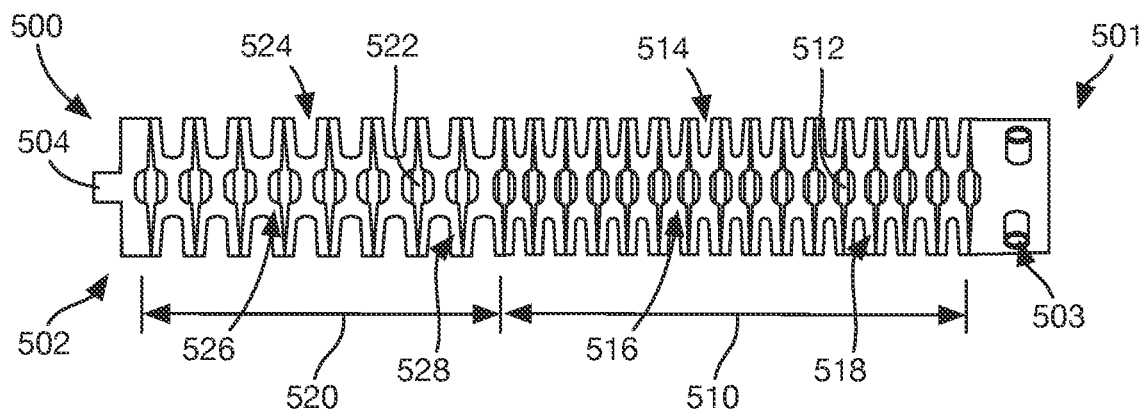
FIG. 39 shows a bottom view of the distal section of FIG. 37.

Referring now to FIG. 38, a side view of the flexible tube frame 500 is shown with cut-outs 516, 526 and slits 518, 528 positioned at and/or near the bottom of the flexible tube frame 500. The cut-outs 516, 526 can optionally have a rounded shape, such as a semi-circle or semi-oval. Each cut-out 516, 526 corresponds to one of the plurality of links 512, 522. The cut-outs 516, 526 are formed on either side of the flexible tube frame 500 when the flexible tube frame 500 is cut from a flat sheet of material (FIG. 41) so that when the flexible tube frame 500 is rolled into a tubular configuration, each pair of cut-outs 516, 526 aligns to form a circle, oval, or other rounded opening to form a row of openings along the bottom of the flexible tube frame 500, as can be seen in FIG. 39.

The slits 518, 528 are formed in the flexible tube frame 500 such that there are two slits 518, 528 cut into each of the plurality of links 512, 522. The slits 518, 528 extend partially upward from the bottom of the flexible tube frame 500 and into the particular link 512, 522. The slits 518, 528 operate similar to relief cuts in that the slits 518, 528 are closed or substantially closed when the flexible tube frame 500 is in a straight configuration and can open or expand when the frame links 512, 522 move toward one another as the flexible tube frame 500 is transitioned into a bent configuration.

Figure 41:
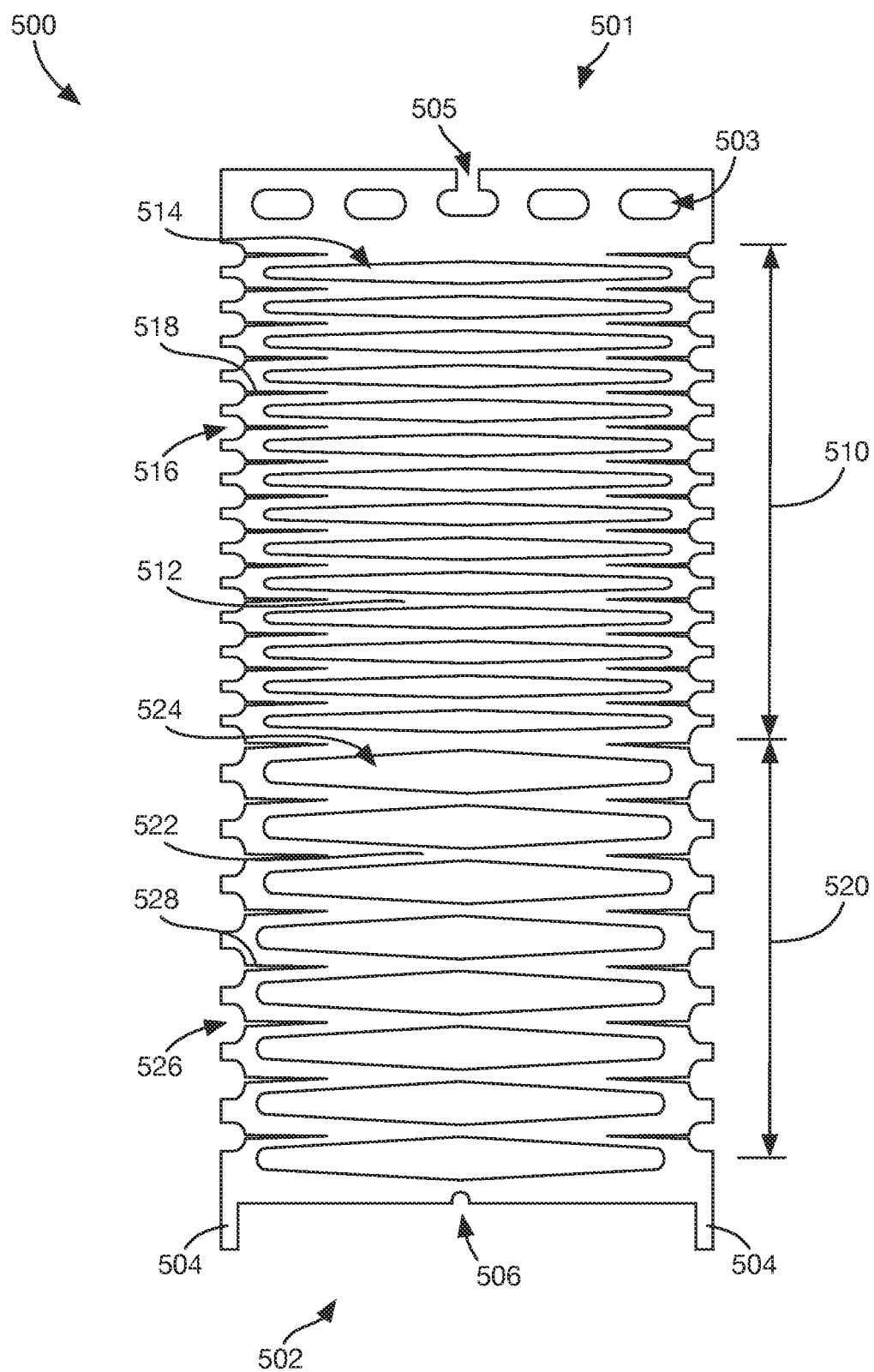
FIG. 41 shows a flat view of a laser cut sheet usable to form the example distal section of FIG. 37.

Referring now to FIG. 41, a plan view of the flexible tube frame 500 in a flat configuration is shown. The flexible tube frame 500 is rectangular or substantially rectangular in shape when in the flat configuration and can be rolled along a longitudinal axis to form a cylindrical or other cross-sectional tube shape. Optionally, the flat pattern shown in FIG. 41 can be used to instruct a laser cutter to cut through an already formed or pre-formed hypotube so that no rolling step is needed. The hypotube can have properties similar to or the same as the example embodiments described above. The links 512, 522 of the flexible tube frame 500 are formed by laser cutting various shapes in the flat sheet of material. In particular, the shape of the links 512, 522 is defined by the slots 514, 524, cut-outs 516, 526, and slits 518, 528. That is, the slots 514, 524 can be cut out of a central region to form the plurality of links 512, 522. The slots 514, 524 can have an elongated and/or tapered shape such that the center region of each slot 514, 524 is wider than the ends of the slots 514, 524 near the sides of the rectangular sheet. The edges of the flattened sheet of material along are shaped by the cut-outs 516, 526 that form a rounded oval-like shape when the sheet of material is rolled into the flexible tube frame 500. The slits 518, 528 extend from the cut-outs 516, 526 toward the center of the sheet. The cut-outs in the distal end 502 of the sheet form two attachment projections 504 that form the single attachment portion 504 when the sheet of material is rolled into a tube shape.

Figure 42:
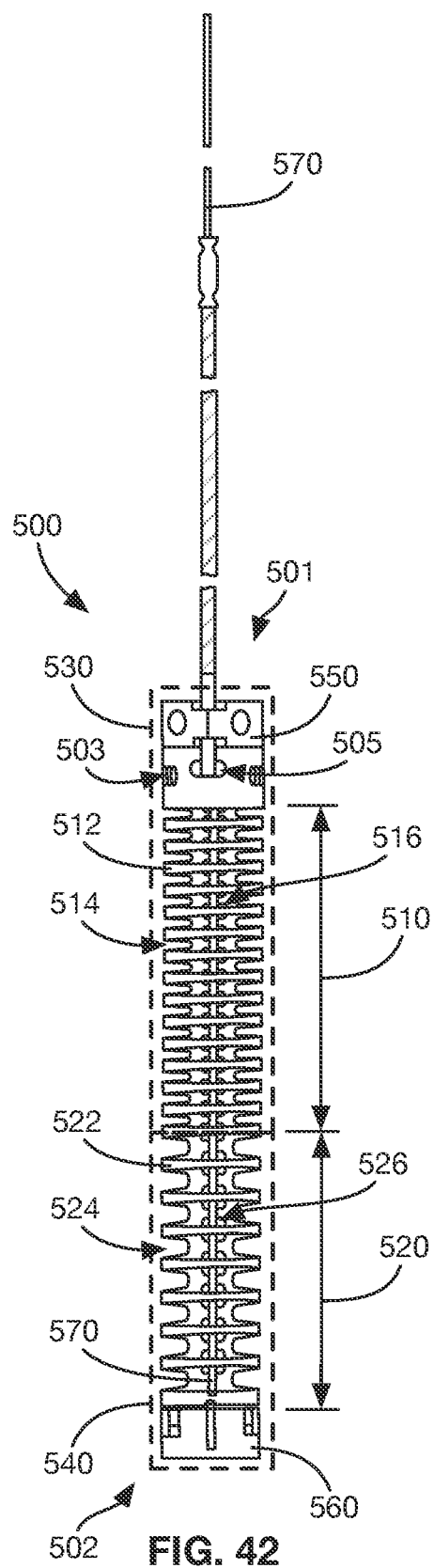
FIG. 42 shows a top view of the example distal section of FIG. 37 with a control wire running therethrough.
Figure 43:
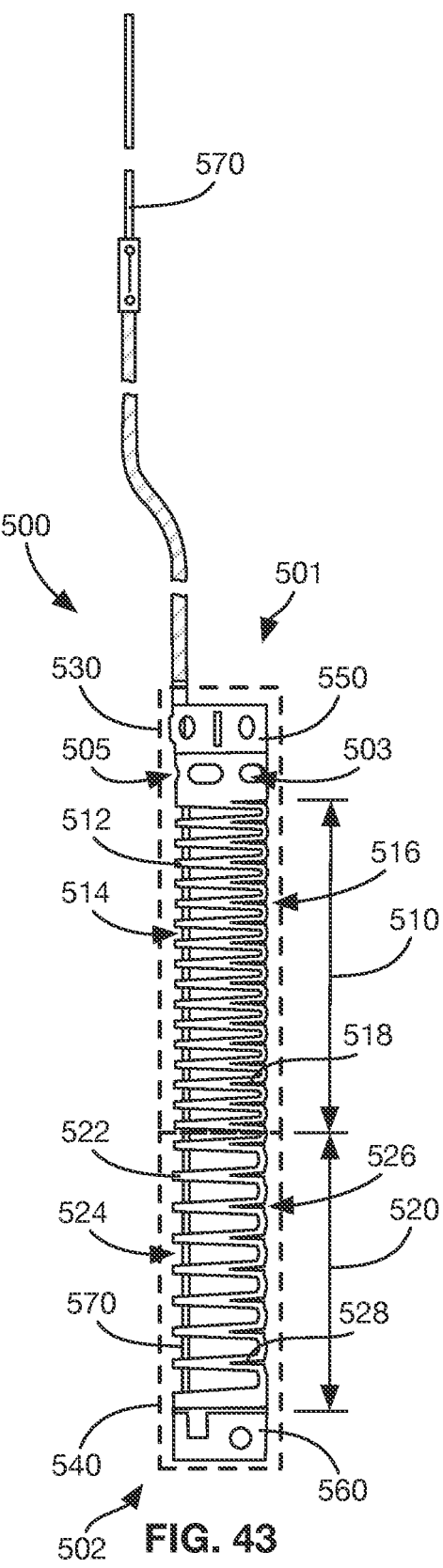
FIG. 43 shows a side view of the example distal section with a control wire of FIG. 42.

Referring now to FIGS. 42 and 43, the flexible tube frame 500 is shown assembled to other components of the distal end of the delivery catheter. The distal end assembly includes the flexible tube frame 500, an optional proximal stationary or fixed ring 550, the optional distal pull or moveable ring 560, and a control wire 570 and operates similar to the distal end assemblies described above. The control wire 570 extends through the proximal ring 550, through the flexible tube frame 500, and attaches to the distal ring 560. Similar to the flexible tube frame shown in FIG. 20C, applying tension to the control wire 570 causes the links 512, 522 to move toward each other and the slots 514, 524 to reduce in width, thereby bending the flexible tube frame 500 towards its top or an inside radius of the bend. Application of bending tension to the control wire 570 also causes the cut-outs 516, 526 and slits 518, 528 on the bottom or outside radius of the bend to expand. In this example embodiment, one control wire is used to control the curvature of the distal region of the delivery catheter, but the device is not so limited in other example embodiments, where the delivery catheter can have more than one control wire.

The links 512 of the first bending portion 510 are closer together than the links 522 of the second bending portion 520, as can be seen in FIGS. 37-39 and 41-43. Consequently, the slots 514 of the first bending portion 510 are narrower than the slots 524 of the second bending portion. The different spacing of the links 512, 522 in the first and second bending portions 510, 520 contributes to the different bending characteristics of the first and second bending portions 510, 520. That is, the more closely spaced links 512 of the first bending portion 510 stiffen the first bending portion 510 relative to the second bending portion 520 so that the first bending portion 510 will have a larger bending radius than the second bending portion 520. Optionally, the spacing of the links 512, 522—and thus, the width of the slots 514, 524—can be the same between the first and second bending portions 510, 520 and the width and/or thickness of the links 512, 522 can be varied to change the bending characteristics of the first and second bending portions 510, 520. That is, thicker and/or wider links 512, 522 can be used to stiffen the bending portion 510, 520, thereby increasing the bending radius when exposed to a bending force. Because of the relative difference in stiffness of the first and second bending portions 510, 520, applying a bending force to the flexible tube frame 500 via the control wire 570 to bend the flexible tube frame 500 to an approximately 90 degree bent condition causes the more flexible second bending portion 520 to bend before the stiffer first bending portion 510. In the illustrated example, a single control wire 570 controls bending of both the first bending portion 510 and the second bending portion 520.

Links with different widths and/or thicknesses can be combined with varied spacing between the links to further customize the bending characteristics, thereby modifying the resulting bending radius when the distal end is bent into a bent condition at around 90 degrees from the straight condition. The variation of the spacing, width, and/or thickness of the links can be between defined bending portions of the distal end—e.g., between first and second bending portions 510, 520—or can change from link to link to create elliptical and other forms of curved bends in the distal end. That is, example distal ends can be designed for arbitrary bending profiles or paths based on the requirements of a particular implantation procedure—such as implantation in the mitral valve or tricuspid valve—or for a particular patient whose heart may have smaller or larger features requiring a different bending profile to reach a target valve.

Referring again to FIGS. 42 and 43, the first and second bending portions 510, 520 include broken lines showing the locations of first and second outer polymer layers 530, 540 that can be made from a flexible material, such as a polymer. The first and second polymer layers 530, 540 can be the same or substantially the same as the polymer layer 2301 described above but can have two different durometers and/or are used over a frame 500 having a plurality of different bending portions (e.g. 510, 520) to provide different bending radii using a single pull wire 570. The polymer layers 530, 540 can have the same durometer or hardness or can have different durometers. Similar to the effect on bending that the size and spacing of the links 512, 522 described above, the bending characteristics of the first and second polymer layers 530, 540 depend on the stiffness or resistance to bending of the material used to form the first and second polymer layers. That is, using a stiffer material will require more force to bend, thereby forming a greater bending radius in the stiffer section. Similarly, a lower durometer material will be softer and easier to bend, thereby resulting in a reduced bending radius relative to the relatively stiffer portion. Thus, similar to the thickness and spacing of the links 512, 522, the material properties of the polymer layers 530, 540 can be modified to change the bending characteristics of the flexible tube frame 500. Various combinations of soft and hard polymer materials used in the first and second polymer layers 530, 540 and/or link dimensions can be used together to provide a large variety of bending radii for first and second bending portions 510, 520.

Referring now to FIGS. 44-50, an example flexible tube frame 600 of the distal end of a flexible delivery catheter in accordance with an example embodiment having first and second bending portions is shown. The flexible tube frame 600 extends from a proximal end 601 to a distal end 602 and can have an overall cylindrical shape that is open at both the proximal and distal ends 601, 602. The flexible tube frame 600 provides support and controlled flexibility to first, second, and third polymer layers 640, 650, 660 (FIGS. 49-50) at the distal end of a delivery catheter. As with the other example embodiments described herein, the flexible tube frame 600 and distal region of the delivery catheter are not limited to a cross-section with a circular shape (e.g., FIG. 47); that is, the cross-section can also be elliptical or ovoid in shape.

The proximal end 601 of the flexible tube frame 600 includes a plurality of rounded, oval or substantially oval shaped windows or cut-outs 603 and a center cut-out or proximal slot 605 that is open to the proximal end 601 of the flexible tube frame 600. The proximal slot 605 can be aligned with a hypotube anchor when the delivery catheter is fully assembled. The plurality of cut-outs 603 are used to provide an opening for adhesive material or polymer material to flow through the flexible tube frame 600 to adhere to other materials, such as a layer underneath or interior to the cut-outs 603 thereby embedding and securing the flexible tube frame 600 in a desired location.

The distal end 602 of the flexible tube frame 600 includes a tooth-shaped attachment portion 604 protruding from the bottom side of the distal end 602 for attaching the flexible tube frame 600 to a distal pull ring 660 (FIGS. 49-50) or another pull ring such as the pull ring 2001 described above. The attachment portion 604 can be formed from a single protrusion or two protrusions that are joined together when the flexible tube frame 600 is formed from a flat sheet of material (see, for example, the flat sheet shown in FIG. 48). The distal end 602 also includes a semi-circular shaped distal cut-out 606 positioned at the top side of the distal end 602 when the flexible tube frame 600 is formed in the tubular configuration. The distal cut-out 606 attaches to a control wire 670 (FIGS. 49-50) or another control wire such as the control wire 1135 described above. The distal end 602 of the flexible tube frame 600 is shown in FIG. 47 to show the circular cross-sectional shape of the flexible tube frame 600 and the relative positions of the attachment portion 604 and the cut-out 606.

Figures 44, 45, 46, 47:
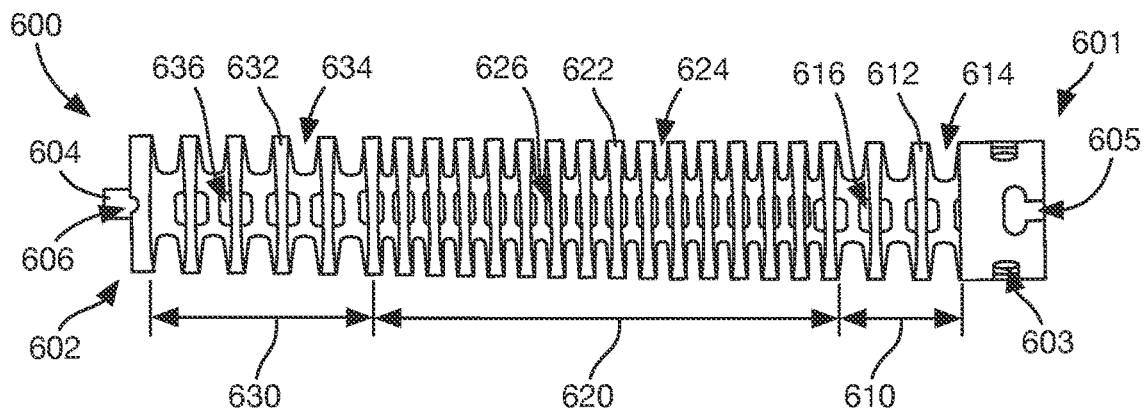
FIG. 44 shows a top view of an example distal section of (or usable in) a delivery catheter as part of a delivery device or system for implanting a valve repair or replacement device, according to an example embodiment.
FIG. 45 shows a side view of the example distal section of FIG. 44.
FIG. 46 shows a bottom view of the example distal section of FIG. 44.
FIG. 47 shows an end view of the example distal section of FIG. 44.

Referring to FIG. 44, a top view of the flexible tube frame 600 is shown. The flexible tube frame 600 has first, second, and third bending portions 610, 620, 630. Each of the first, second, and third bending portions 610, 620, 630 is formed from a plurality of links 612, 622, 632 that are defined by slots or grooves 614, 624, 634. The links 612, 622, 632 can also include cut-outs 616, 626, 636 and slits 618, 628, 638. Each of the plurality of links 612, 622, 632 can have a circular shape, and is spaced apart from at least one other link by a slot or groove 614, 624, 634 at the tops and sides of the links 612, 622, 632 in a circular configuration.

Referring now to FIG. 45, a side view of the flexible tube frame 600 is shown with cut-outs 616, 626, 636 and slits 618, 628, 638 positioned near the bottom of the flexible tube frame 600. The cut-outs 616, 626, 636 can have a rounded shape, such as a semi-circle or semi-oval. Each cut-out 616, 626, 636 corresponds to one of the plurality of links 612, 622, 632. The cut-outs 616, 626, 636 are formed on either side of the flexible tube frame 600 when the flexible tube frame 600 is cut from a flat sheet of material (FIG. 48) so that when the flexible tube frame 600 is rolled into a tubular configuration, each pair of cut-outs 616, 626, 636 aligns to form a circle, oval, or other rounded opening to form a row of openings along the bottom of the flexible tube frame 600, as can be seen in FIG. 46. The slits 618, 628, 638 are formed in the flexible tube frame 600 such that there are two slits 618, 628, 638 cut into each of the plurality of links 612, 622, 632. The slits 618, 628, 638 extend partially upward from the bottom of the flexible tube frame 600 and into the particular link 612, 622, 632. The slits 618, 628, 638 operate similar to relief cuts in that the slits 618, 628, 638 are closed or substantially closed when the flexible tube frame 600 is in a straight configuration and can open or expand when the frame links 612, 622, 632 move toward one another as the flexible tube frame 600 is transitioned into a bent configuration.

Figure 48:
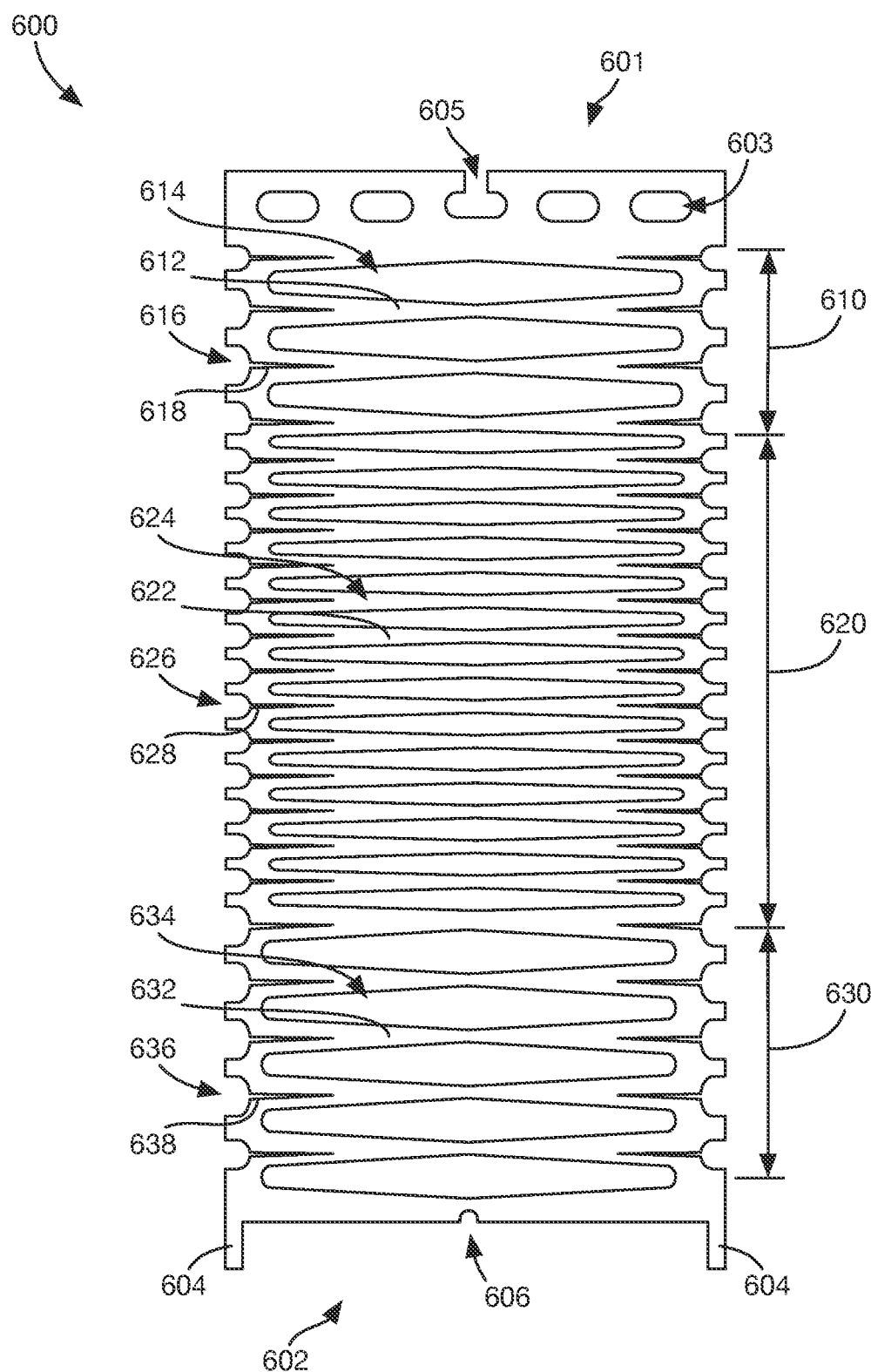
FIG. 48 shows a flat view of a laser cut sheet usable to make the distal section of FIG. 44.

Referring now to FIG. 48, a plan view of the flexible tube frame 600 in a flat configuration is shown. The flexible tube frame 600 is rectangular or substantially rectangular in shape when in the flat configuration and can be rolled along a longitudinal axis to form a cylindrical tube shape. Optionally, the flat pattern shown in FIG. 48 can be used to instruct a laser cutter to cut through an already formed hypotube so that no rolling step is needed. The hypotube can have properties similar to or the same as the example embodiments described above. The links 612, 622, 632 of the flexible tube frame 600 are formed by laser cutting various shapes in the flat sheet of material. In particular, the shape of the links 612, 622, 632 is defined by the slots 614, 624, 634, cut-outs 616, 626, 636, and slits 618, 628, 638. That is, the slots 614, 624, 634 can be cut out of a central region to form the plurality of links 612, 622, 632. The slots 614, 624, 634 can have an elongated and/or tapered shape such that the center region of each slot 614, 624, 634 is wider than the ends of the slots 614, 624, 634 near the sides of the rectangular sheet. The edges of the flattened sheet of material are shaped by the cut-outs 616, 626, 636 that form a rounded oval-like shape when the sheet of material is rolled into the flexible tube frame 600. The slits 618, 628, 638 extend from the cut-outs 616, 626, 636 toward the center of the sheet. The cut-outs in the distal end 602 of the sheet form two attachment projections 604 that form the single attachment portion 604 when the sheet of material is rolled into a tube shape.

Referring now to FIGS. 49 and 50, the flexible tube frame 600 is shown assembled to other components of the distal end of the delivery catheter. The distal end assembly includes the flexible tube frame 600, an optional proximal stationary or fixed ring 670, the optional distal pull or moveable ring 680, and a control wire 690 and operates similar to the distal end assemblies described above. The control wire 690 extends through the proximal ring 670, through the flexible tube frame 600, and attaches to the distal ring 680. Similar to the flexible tube frame shown in FIG. 20C, applying tension to the control wire 690 causes the links 612, 622, 632 to move toward each other and the slots 614, 624, 634 to reduce in width, thereby bending the flexible tube frame 600 towards its top or an inside radius of the bend. Application of bending tension to the control wire 690 also causes the cut-outs 616, 626, 636 and slits 618, 628, 638 on the bottom or outside radius of the bend to expand. In this example embodiment, one control wire is used to control the curvature of the distal region of the delivery catheter, but the device is not so limited in other example embodiments, where the delivery catheter can have more than one control wire.

The links 612, 632 of the first and third bending/curved portions 610, 630 are further apart than the links 622 of the second bending portion 620, as can be seen in FIGS. 44-46 and 49-50. Consequently, the slots 614, 634 of the first and third bending portions 610, 630 are wider than the slots 624 of the second bending portion. The different spacing of the links 612, 622, 632 in the first, second, and third bending portions 610, 620, 630 contributes to the different bending characteristics of the first, second, and third bending portions 610, 620, 630. That is, the more closely spaced links 622 of the second bending portion 620 stiffen the second bending portion 620 relative to the first and third bending portions 610, 630 so that the second bending portion 620 will have a larger bending radius than the first and third bending portions 610, 630. Optionally, the spacing of the links 612, 622, 632—and thus, the width of the slots 614, 624, 634—can be the same between the first, second, and third bending portions 610, 620, 630 and the width and/or thickness of the links 612, 622, 632 can be varied to change the bending characteristics of the first, second, and third bending/curved portions 610, 620, 630. That is, thicker or wider links 612, 622, 632 can be used to stiffen one or more of the bending portions 610, 620, 630, thereby increasing the bending radius when exposed to a bending force relative to one or more bending portions that are more flexible. Because of the relative difference in stiffness of the first, second, and third bending portions 610, 620, 630, applying a bending force to the flexible tube frame 600 via the control wire 690 to bend the flexible tube frame 600 to an approximately 90 degree bent condition causes the more flexible first and third bending portions 610, 630 to bend before the stiffer second bending portion 620. In the illustrated example, a single control wire 690 controls bending of the first bending portion 610 and the second bending portion 620, and the third bending portion.

Links with different widths and/or thicknesses can be combined with varied spacing between the links to further customize the bending characteristics, thereby modifying the resulting bending radius when the distal end is bent into a bent condition at around 90 degrees from the straight condition (or from an adjacent straightened portion). The variation of the spacing, width, and/or thickness of the links can be defined bending portions of the distal end—e.g., between first, second, and third bending portions 610, 620, 630—or can change from link to link to create elliptical and other forms of curved bends in the distal end. That is, example distal ends can be designed for arbitrary bending profiles or paths based on the requirements of a particular implantation procedure—such as implantation in the mitral valve or tricuspid valve—or for a particular patient whose heart may have smaller or larger features requiring a different bending profile to reach a target valve.

Referring again to FIGS. 49 and 50, the first, second, and third bending portions 610, 620, 630 include broken lines showing the locations of first, second, and third polymer layers 640, 650, 660 that can be made from a flexible material, such as a polymer. The polymer layers 640, 650, 660 can have the same durometer or hardness or can have different durometers. Similar to the effect on bending that the size and spacing of the links 612, 622, 632 described above, the bending characteristics of the first, second, and third polymer layers 640, 650, 660 depend on the stiffness or resistance to bending of the material used to form the first and second polymer layers. That is, using a stiffer material will be require more force to bend, thereby forming a greater bending radius in the stiffer section. Similarly, a lower durometer material will be softer and easier to bend, thereby resulting in a reduced bending radius relative to the stiffer portion. Thus, similar to the thickness and spacing of the links 612, 622, 632 the material properties of the polymer layers 640, 650, 660 can be modified to change the bending characteristics of the flexible tube frame 600. Various combinations of soft and hard polymer materials used in the first, second, and third polymer layers 640, 650, 660 and link dimensions can be used together to provide a large variety of bending radii for first, second, and third bending portions 610, 620, 630. In addition, the first, second, and third polymer layers 640, 650, 660 (or any number of different polymer layers) can be used with any of the frames described herein, such as frames having a single, uniform flexing section to form bending portions with different bending radii.

It should be noted that the devices and apparatuses described herein can be used with other surgical procedures and access points (e.g., transapical, open heart, etc.). It should also be noted that the devices described herein (e.g., the deployment tools) can also be used in combination with various other types of valve repair or replacement devices and/or prosthetic valves different from the examples described herein.

For purposes of this description, certain aspects, advantages, and novel features of the embodiments of this disclosure are described herein. The disclosed methods, apparatuses, and systems should not be construed as limiting in any way. Instead, the present disclosure is directed toward all novel and nonobvious features and aspects of the various disclosed embodiments, alone and in various combinations and sub-combinations with one another. The methods, apparatuses, and systems are not limited to any specific aspect or feature or combination thereof, nor do the disclosed embodiments require that any one or more specific advantages be present, or problems be solved.

Although the operations of some of the disclosed embodiments are described in a particular, sequential order for convenient presentation, it should be understood that this manner of description encompasses rearrangement, unless a particular ordering is required by specific language. For example, operations described sequentially can in some cases be rearranged or performed concurrently. Moreover, for the sake of simplicity, the attached figures may not show the various ways in which the disclosed methods can be used in conjunction with other methods. Additionally, the description sometimes uses terms like "provide" or "achieve" to describe the disclosed methods. These terms are high-level abstractions of the actual operations that are performed. The actual operations that correspond to these terms can vary depending on the particular implementation and are readily discernible by one of ordinary skill in the art. Still further, example or representative values and ranges may be included to assist in understanding the present application, however, such values and ranges are not to be construed in a limiting sense and are intended to be critical values or ranges only if so expressly stated.

In view of the many possible embodiments to which the principles of the disclosure can be applied, it should be recognized that the illustrated embodiments are only preferred examples of the invention and should not be taken as limiting the scope of the disclosure. Rather, the scope of the disclosure is defined by the following claims.

While various inventive aspects, concepts and features of the disclosures may be described and illustrated herein as embodied in combination in the example embodiments, these various aspects, concepts, and features may be used in many alternative embodiments, either individually or in various combinations and sub-combinations thereof. Unless expressly excluded herein all such combinations and sub-combinations are intended to be within the scope of the present application. Still further, while various alternative embodiments as to the various aspects, concepts, and features of the disclosures—such as alternative materials, structures, configurations, methods, devices, and components, alternatives as to form, fit, and function, and so on—may be described herein, such descriptions are not intended to be a complete or exhaustive list of available alternative embodiments, whether presently known or later developed. Those skilled in the art may readily adopt one or more of the inventive aspects, concepts, or features into additional embodiments and uses within the scope of the present application even if such embodiments are not expressly disclosed herein.

Moreover, while various aspects, features and concepts may be expressly identified herein as being inventive or forming part of a disclosure, such identification is not intended to be exclusive, but rather there may be inventive aspects, concepts, and features that are fully described herein without being expressly identified as such or as part of a specific disclosure, the disclosures instead being set forth in the appended claims. Descriptions of example methods or processes are not limited to inclusion of all steps as being required in all cases, nor is the order that the steps are presented to be construed as required or necessary unless expressly so stated. Further, the treatment techniques, methods, operations, steps, etc. described or suggested herein or in incorporated references can be performed on a living animal or on a non-living simulation, such as on a cadaver, cadaver heart, simulator (e.g. with the body parts, tissue, etc. being simulated), etc. The words used in the claims have their full ordinary meanings and are not limited in any way by the description of the embodiments in the specification.

What is claimed is:

1. A delivery catheter for delivering a device to a native valve of a patient's heart, comprising:
    a flexible tube having a main lumen and a single control wire lumen;
    a plurality of links disposed in a distal region of the flexible tube;
    wherein the plurality of links are configured such that the distal region has a first flexible portion having a first stiffness and a second flexible portion having a second stiffness that is different than the first stiffness,
    wherein each link is aligned with and connected to at least one adjacent link with a slot formed between each pair of adjacent links;
    wherein the links are tapered such that a top portion of each link is narrower than a bottom portion of each link when the links are viewed from a side;
    wherein each link includes an orifice at the bottom of the link;
    wherein each link includes at least one slit, wherein the slit begins at the orifice and extends upward along at least a portion of the link;
    wherein the slits extend less than halfway across the flexible tube when viewed from the side and the flexible tube frame is straight, and wherein the slits comprise a first end at the orifice, a second end distal from the first end, and wherein the slits taper from the first end to the second end when the flexible tube frame is straight;

wherein the links expand at the slits when the flexible tube is moved into a curved configuration; and a control wire in the control wire lumen that is connected to the plurality of links, wherein applying tension to the control wire causes the distal region of the flexible tube to bend.

2. The delivery catheter of claim 1, wherein each link is connected to at least one adjacent link only at the bottom portion of the links.

3. The delivery catheter of claim 1, wherein the top portions of the links are drawn closer together when tension is applied to the control wire to bend the distal region.

4. The delivery catheter of claim 3, wherein the plurality of links are in a straight configuration when tension is removed from the control wire.

5. The delivery catheter of claim 3, wherein a coil sleeve surrounds a portion of the control wire to inhibit buckling of a proximal region of the delivery catheter.

6. The delivery catheter of claim 1, wherein the flexible tube comprises a ring distal to the plurality of links, and the control wire is fixedly attached to the ring.

7. The delivery catheter of claim 1, wherein the links are cut from a single flat sheet of material that is rolled to form the links.

8. The delivery catheter of claim 1, wherein the flexible tube further comprises a polymer coating.

9. The delivery catheter of claim 1, wherein the flexible tube further comprises a polyether block amide coating.

10. The delivery catheter of claim 1, wherein the plurality of links are comprised of at least one of a shape memory material, stainless steel, or a polymer.

11. The delivery catheter of claim 1, further comprising:
a first ring in the distal region of the flexible tube; and
a second ring in the distal region of the flexible tube that is spaced apart from the first ring;
wherein the plurality of links is disposed in the distal region of the flexible tube between the first ring and the second ring.

12. A system comprising:
a valve repair device or a valve replacement device;
a delivery catheter configured to deploy the valve repair device or the valve replacement device at an implant site;
wherein the delivery catheter comprises:
a flexible tube having a main lumen and a single control wire lumen;
a plurality of links disposed in a distal region of the flexible tube;
wherein each link is aligned with and connected to at least one adjacent link with a slot formed between each pair of adjacent links;
wherein top portion of each link is narrower than a bottom portion of each link when the links are viewed from a side;
wherein each link includes an orifice at the bottom of the link;
wherein each link includes at least one slit, wherein the slit begins at the orifice and extends upward along at least a portion of the link;
wherein the slits extend less than halfway across the flexible tube when viewed from the side and the flexible tube frame is straight, and wherein the slits comprise a first end at the orifice, a second end distal from the first end, and wherein the slits taper from the first end to the second end when the flexible tube frame is straight;

wherein the links expand at the slits when the flexible tube is moved into a curved configuration; and a control wire in the control wire lumen that is connected to the plurality of links, wherein applying tension to the control wire causes the distal region of the flexible tube to bend.

13. The system of claim 12, wherein each link is connected to at least one adjacent link only at a bottom portion of the links.

14. The system of claim 12, wherein the top portions of the links are drawn closer together when tension is applied to the control wire to bend the distal region.

15. The system of claim 14, wherein the plurality of links are in a straight configuration when tension is removed from the control wire.

16. The system of claim 14, wherein a coil sleeve surrounds a portion of the control wire to inhibit buckling of a proximal region of the delivery catheter.

17. The system of claim 12, wherein the flexible tube comprises a ring distal to the plurality of links, and the control wire is fixedly attached to the ring.

18. The system of claim 12, wherein the links are cut from a single flat sheet of material that is rolled to form the links.

19. The system of claim 12, wherein the flexible tube further comprises a polyether block amide coating and the plurality of links are comprised of at least one of a shape memory material, stainless steel, or a polymer.

20. The system of claim 12, further comprising:
a first ring in the distal region of the flexible tube; and
a second ring in the distal region of the flexible tube that is spaced apart from the first ring;
wherein the plurality of links is disposed in the distal region of the flexible tube between the first ring and the second ring.

21. A delivery catheter for delivering a device to a native valve of a patient's heart, comprising:
a flexible tube having a main lumen and a single control wire lumen;
a plurality of links disposed in a distal region of the flexible tube;
wherein the plurality of links are configured such that the distal region has a first flexible portion having a first stiffness and a second flexible portion having a second stiffness that is different than the first stiffness;
wherein each link is aligned with and connected to at least one adjacent link with a slot formed between each pair of adjacent links;
wherein a top portion of each link is narrower than a bottom portion of each link when the links are viewed from a side;
wherein each link includes an orifice at the bottom of the link;
wherein each link includes at least one slit, wherein the slit begins at the orifice and extends upward along at least a portion of the link;
wherein the slits extend less than halfway across the flexible tube when viewed from the side and the flexible tube frame is straight, and wherein the slits comprise a first end at the orifice, a second end distal from the first end, and wherein the slits taper from the first end to the second end when the flexible tube frame is straight;
wherein the links expand at the slits when the flexible tube is moved into a curved configuration; and a control wire in the control wire lumen that is connected to the plurality of links, wherein applying tension to the control wire causes the distal region of the flexible tube to bend.

* * * * *